United States Patent
Kalluri et al.

(10) Patent No.: US 9,921,223 B2
(45) Date of Patent: Mar. 20, 2018

(54) ANALYSIS OF GENOMIC DNA, RNA, AND PROTEINS IN EXOSOMES FOR DIAGNOSIS AND THERANOSIS

(71) Applicant: Board of Regents, The University of Texas System, Austin, TX (US)

(72) Inventors: Raghu Kalluri, Houston, TX (US); Sónia Melo, Porto (PT)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/101,857

(22) PCT Filed: Dec. 4, 2014

(86) PCT No.: PCT/US2014/068630
§ 371 (c)(1),
(2) Date: Jun. 3, 2016

(87) PCT Pub. No.: WO2015/085096
PCT Pub. Date: Jun. 11, 2015

(65) Prior Publication Data
US 2017/0059572 A1    Mar. 2, 2017

Related U.S. Application Data

(60) Provisional application No. 61/911,863, filed on Dec. 4, 2013.

(51) Int. Cl.
| | | |
|---|---|---|
| *G01N 33/574* | (2006.01) | |
| *A61K 35/12* | (2015.01) | |
| *C12Q 1/68* | (2018.01) | |
| *A61K 9/50* | (2006.01) | |

(52) U.S. Cl.
CPC ....... *G01N 33/57488* (2013.01); *A61K 35/12* (2013.01); *C12Q 1/6886* (2013.01); *A61K 9/5068* (2013.01); *C12Q 2600/156* (2013.01); *C12Q 2600/158* (2013.01); *G01N 2333/705* (2013.01)

(58) Field of Classification Search
CPC ........ G01N 2333/705; G01N 33/57488; C12C 1/6886; A61K 9/5068
See application file for complete search history.

(56) References Cited

U.S. PATENT DOCUMENTS

| | | | |
|---|---|---|---|
| 2003/0064949 A1 | 4/2003 | Nielsen et al. | |
| 2004/0028692 A1 | 2/2004 | Zitvogel et al. | |
| 2010/0196426 A1* | 8/2010 | Skog | C12Q 1/6806 424/400 |
| 2012/0196285 A1* | 8/2012 | Okamoto | C12N 15/1006 435/6.11 |
| 2013/0156801 A1 | 6/2013 | Bond et al. | |

FOREIGN PATENT DOCUMENTS

WO    WO 2004/014954    2/2004

OTHER PUBLICATIONS

Adamczyk et al., "Characterization of soluble and exosomal forms of the EGFR released from pancreatic cancer cells," *Life Sciences*, 89:304-312, 2011.
Andre et al., "Malignant effusions and immunogenic tumour-derived exosomes," *Lancet*, 360:295-305, 2002.
Balaj et al., "Tumour microvesicles contain retrotransposon elements and amplified oncogene sequences," *Nature Communications*, 2:180, 2011.
Ballehaninna and Chamberlain, "Biomarkers for pancreatic cancer: promising new markers and options beyond CA 19-9," *Tumour Biology*, 34:3279-3292, 2013.
Baran et al., "Circulating tumour-derived microvesicles in plasma of gastric cancer patients," *Cancer Immunology, Immunotherapy*, 59:841-850, 2010.
Biankin et al., "Pancreatic cancer genomes reveal aberrations in axon guidance pathway genes," *Nature*, 491:399-405, 2012.
Chen et al. ,"BEAMing and Droplet Digital PCR Analysis of Mutant IDH1 mRNA in Glioma Patient Serum and Cerebrospinal Fluid Extracellular Vesicles," *Molecular Therapy. Nucleic Acids*, 2:e109, 2013.
Choi et al., "The protein interaction network of extracellular vesicles derived from human colorectal cancer cells," *Journal of Proteome Research*, 11:1144-1151, 2012.
Ciravolo et al. ,"Potential role of HER2-overexpressing exosomes in countering trastuzumab-based therapy," *Journal of Cellular Physiology*, 227:658-667, 2012.
Crowley et al., "Liquid biopsy: monitoring cancer-genetics in the blood," *Nature Reviews, Clinical Oncology*, 10:472-484, 2013.
Del Villano et al.,"Radioimmunometric assay for a monoclonal antibody-defined tumor marker, CA 19-9," *Clinical Chemistry*, 29:549-552, 1983.
Demoiry Beckler et al., "Proteomic analysis of exosomes from mutant KRAS colon cancer cells identifies intercellular transfer of mutant KRAS," *Molecular & Cellular Proteomics: MCP*, 12:343-355, 2013.
Escudier et al. ,"Vaccination of metastatic melanoma patients with autologous dendritic cell (DC) derived-exosomes: results of the first phase 1 clinical trial," *J. Transl. Med.*, 3(10):1-13, 2005.
Grange et al., "Microvesicles released from human renal cancer stem cells stimulate angiogenesis and formation of lung premetastatic niche," *Cancer Research*, 71:5346-5356, 2011.

(Continued)

*Primary Examiner* — Kevin K Hill
(74) *Attorney, Agent, or Firm* — Parker Highlander PLLC

(57) ABSTRACT

The present invention provides that exosomes from human body fluid samples contain double stranded genomic DNA that spans all chromosomes and may be used to determine the mutation status of genes of interest in diseases, such as cancer. Furthermore, the present invention provides the use of exosomes to produce therapeutic proteins and for their use in therapy as well as the detection of cancer cell-derived exosomes to diagnose cancer and monitor therapeutic response.

12 Claims, 55 Drawing Sheets

(56) References Cited

OTHER PUBLICATIONS

Guescini et al., "C2C12 myoblasts release micro-vesicles containing mtDNA and proteins involved in signal transduction," *Experimental Cell Research*, 316:1977-1984, 2010.
Jazieh et al. ,"The clinical utility of biomarkers in the management of pancreatic adenocarcinoma," *Seminars in Radiation Oncology*, 24:67-76, 2014.
Ji et al. ,"Proteome profiling of exosomes derived from human primary and metastatic colorectal cancer cells reveal differential expression of key metastatic factors and signal transduction components," *Proteomics*, 13:1672-1686, 2013.
Kahlert and Kalluri, "Exosomes in tumor microenvironment influence cancer progression and metastasis," *J. Mol. Med. (Berl.)*, 91:431-437, 2013.
Kahlert et al., "Identification of double-stranded genomic DNA spanning all chromosomes with mutated KRAS and p53 DNA in the serum exosomes of patients with pancreatic cancer," *The Journal of Biological Chemistry*, 289:3869-3875, 2014.
Kleeff et al., "The cell-surface heparan sulfate proteoglycan glypican-1 regulates growth factor action in pancreatic carcinoma cells and is overexpressed in human pancreatic cancer," *The Journal of Clinical Investigation*, 102:1662-1673, 1998.
Kosaka et al., "Trash or Treasure: extracellular microRNAs and cell-to-cell communication," *Frontiers in Genetics*, 4:173, 2013.
Lau et al.,"Role of Pancreatic Cancer-derived Exosomes in Salivary Biomarker Development," *The Journal of Biological Chemistry*, 288:26888-26897, 2013.
Matsuda et al., "Glypican-1 is overexpressed in human breast cancer and modulates the mitogenic effects of multiple heparin-binding growth factors in breast cancer cells," *Cancer Research*, 61:5562-5569, 2001.
Mears et al., "Proteomic analysis of melanoma-derived exosomes by two-dimensional polyacrylamide gel electrophoresis and mass spectrometry," *Proteomics*, 4:4019-4031, 2004.
Moore et al., "Genetic profile of 22 pancreatic carcinoma cell lines. Analysis of K-ras, p53, p16 and DPC4/Smad4," *Virchows Arch.*, 439:798-802, 2001.
Morris et al., "KRAS, Hedgehog, Wnt and the twisted developmental biology of pancreatic ductal adenocarcinoma," *Nature Reviews, Cancer*, 10:683-695, 2010.
Mouliere and Thierry, "The importance of examining the proportion of circulating DNA originating from tumor, microenvironment and normal cells in colorectal cancer patients," *Expert Opinion on Biological Therapy*, 12(Suppl. 1):S209-215, 2012.
Murtaza et al., "Non-invasive analysis of acquired resistance to cancer therapy by sequencing of plasma DNA," *Nature*, 497:108-112, 2013.
Nolte-'t Hoen et al., "Deep sequencing of RNA from immune cell-derived vesicles uncovers the selective incorporation of small non-coding RNA biotypes with potential regulatory functions," *Nucleic Acids Research*, 40:9272-9285, 2012.
PCT International Preliminary Report on Patentability issued in International Application No. PCT/US2014/068630, dated Jun. 7, 2016.
PCT International Search Report and Written Opinion issued in International Application No. PCT/US2014/068630, dated Feb. 23, 2015.
Peinado et al., "Melanoma exosomes educate bone marrow progenitor cells toward a pro-metastatic phenotype through MET," *Nature Medicine*, 18:883-891, 2012.
Pisitkun et al., "Identification and proteomic profiling of exosomes in human urine," *Proceedings of the National Academy of Sciences USA*, 101:13368-13373, 2004.
Raposo and Stoorvogel, "Extracellular vesicles: exosomes, microvesicles, and friends," *The Journal of Cell Biology*, 200:373-383, 2013.
Runz et al., "Malignant ascites-derived exosomes of ovarian carcinoma patients contain CD24 and EpCAM," *Gynecologic Oncology*, 107:563-571, 2007.
Silva et al., "Analysis of exosome release and its prognostic value in human colorectal cancer," *Genes, Chromosomes & Cancer*, 51:409-418, 2012.
Skog et al., "Glioblastoma microvesicles transport RNA and proteins that promote tumour growth and provide diagnostic biomarkers," *Nature Cell Biology*, 10:1470-1476, 2008.
Su et al., "Glypican-1 is frequently overexpressed in human gliomas and enhances FGF-2 signaling in glioma. cells," *The American Journal of Pathology*, 168:2014-2026, 2006.
Taylor and Gercel-Taylor, "Exosomes/microvesicles: mediators of cancer-associated immunosuppressive microenvironments," *Seminars in Immunopathology*, 33:441-454, 2011.
Taylor and Gercel-Taylor, "MicroRNA signatures of tumor-derived exosomes as diagnostic biomarkers of ovarian cancer," *Gynecologic Oncology*, 110:13-21, 2008.
Theiry et al., "Isolation and characterization of exosomes from cell culture supernatants and biological fluids," *Current Protocols in Cell Biology*, Ed., Juan S. Bonifacino et al., Chapter 3, Unit 3.22, 2006.
Thery et al., "Membrane vesicles as conveyors of immune responses," *Nature Reviews, Immunology*, 9:581-593, 2009.
Valadi et al., "Exosome-mediated transfer of mRNAs and microRNAs is a novel mechanism of genetic exchange between cells," *Nature Cell Biology*, 9:654-659, 2007.
Whipple et al., "KrasG12D-driven genetic mouse model of pancreatic cancer requires glypican-1 for efficient proliferation and angiogenesis," *Oncogene*, 31:2535-2544, 2012.
Yong, "Cancer biomarkers: Written in blood," *Nature*, 511:524-526, 2014.
Zeelenberg et al., "Targeting tumor antigens to secreted membrane vesicles in vivo induces efficient antitumor immune responses," *Cancer Research*, 68:1228-1235, 2008.
Lau et al., Supplemental material for "Role of pancreatic cancer-derived exosomes in salivary biomarker development," *Journal of Biological Chemistry*, 288(37):26888-26897, located at http://www.jbc.org/content/suppl/2013/08/01/M113.452458.DC1, 2013.
Li et al., "Claudin-containing exosomes in the peripheral circulation of women with ovarian cancer," *BMC Cancer*, 9(1):244, 2009.
Logozzi et al., "High levels of exosomes expressing CD63 and caveolin-1 in plasma of melanoma patients," *PLoS ONE*, 4(4):e5219, pp. 1-10, 2009.
Partial Supplementary European Search Report issued in European Application No. 14867768.5, dated Jul. 17, 2017.
Properzi et al., "Exosomes: the future of biomarkers in medicine," *Biomarkers in Medicine*, 7(5):769-778, 2013.
Cai et al., "Extracellular vesicle-mediated transfer of donor genomic DNA to recipient cells is a novel mechanism for genetic influence between cells," *J. Mol. Cell Biol.*, 5(4):227-238, 2013.
Extended European Search Report issued in corresponding European Patent Application No. 14867768.5, dated Oct. 19, 2017.
Guescini et al., "Astrocytes and Glioblastoma cells release exosomes carrying mtDNA," *J. Neural Transm.*, 117(1):1435-1463, 2009.
Ronquist et al., "Human prostasomes contain chromosomal DNA," *Prostate*, 69(7):737-746, 2009.
Ronquist et al., "Prostasomes are heterogeneous regarding size and apperance but affiliated to one DNA-containing exosome family," *Prostate*, 72(16):1736-1745, 2012.
Ronquist et al., "Protasomal DNA characterization and transfer into human sperm," *Mol. Reprod. Dev.*, 78(7):467-476, 2011.

* cited by examiner

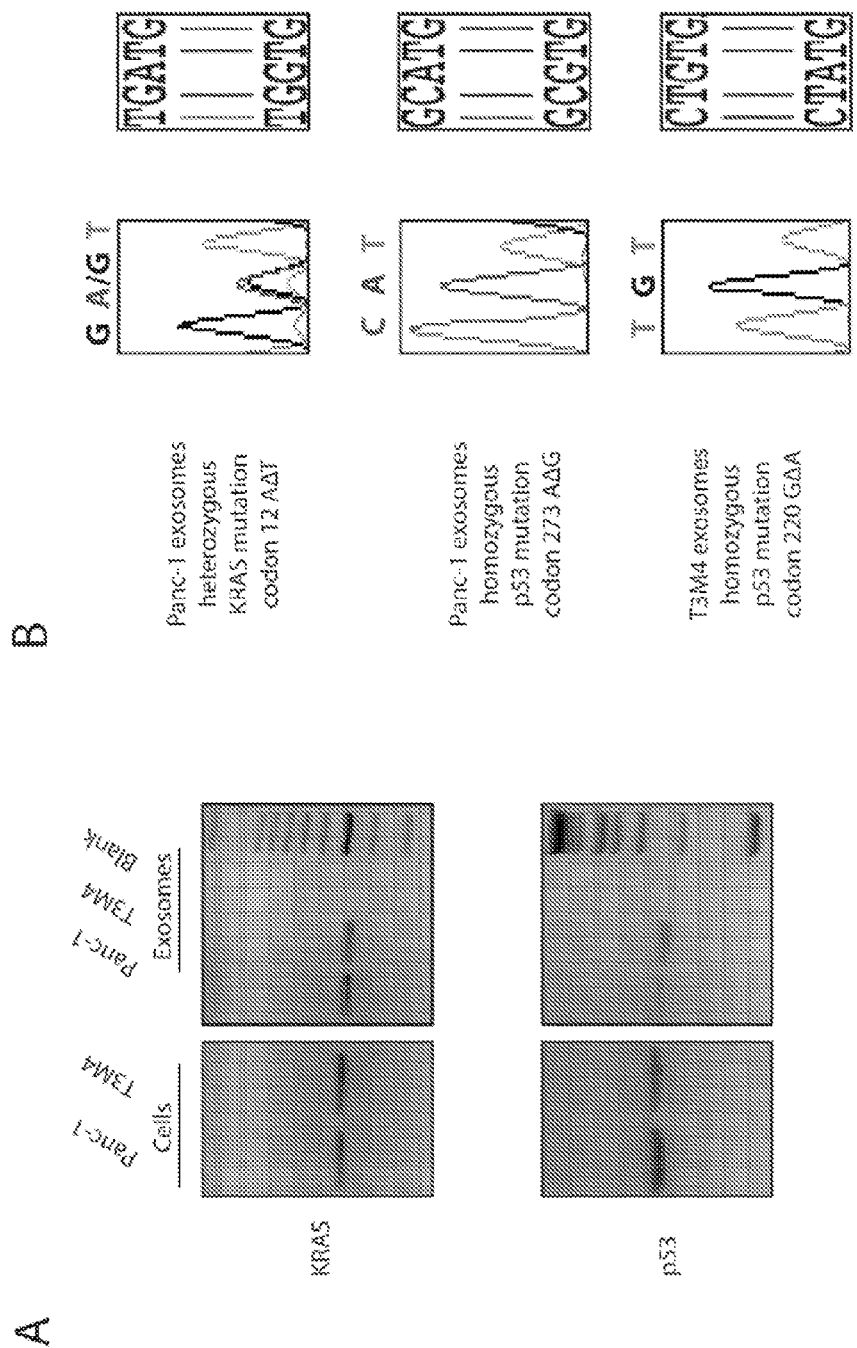
FIGS. 2A-B

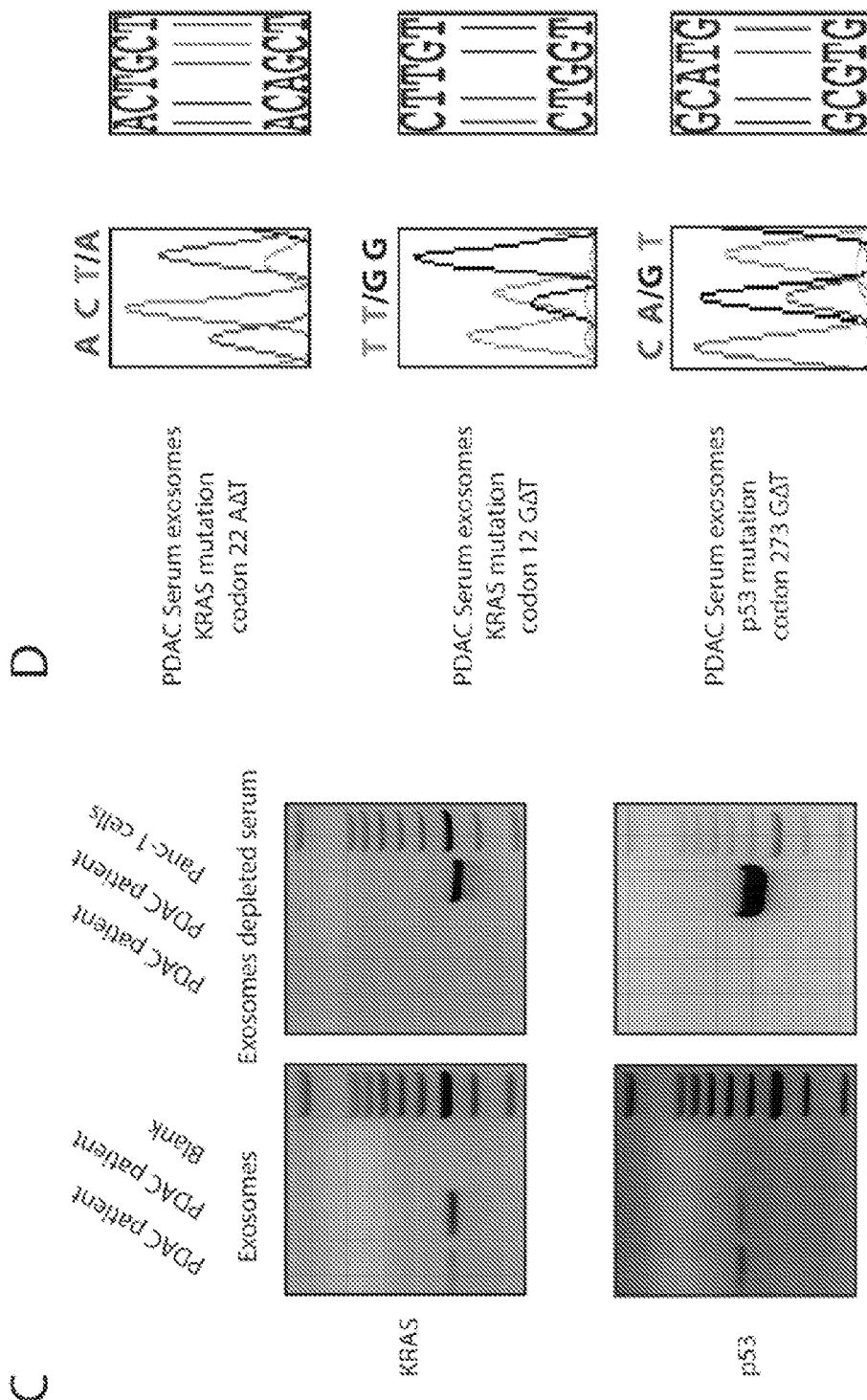
FIGS. 2C-D

FIGS. 11A-B

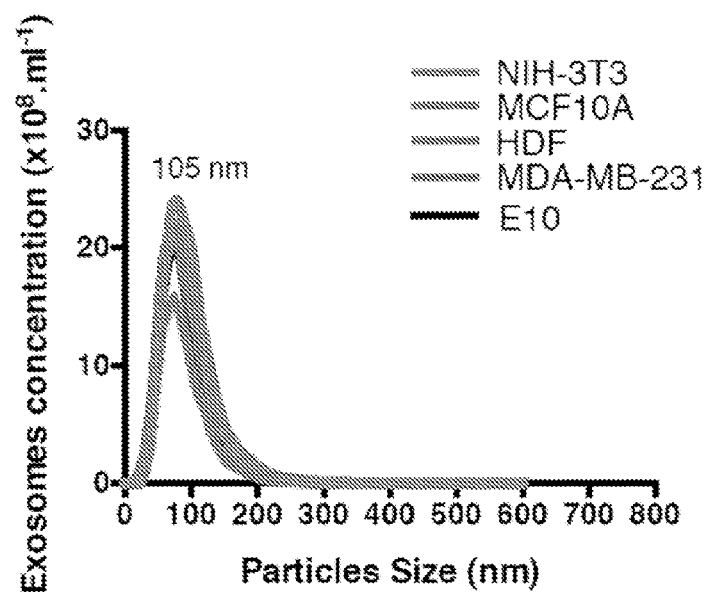
FIG. 14A
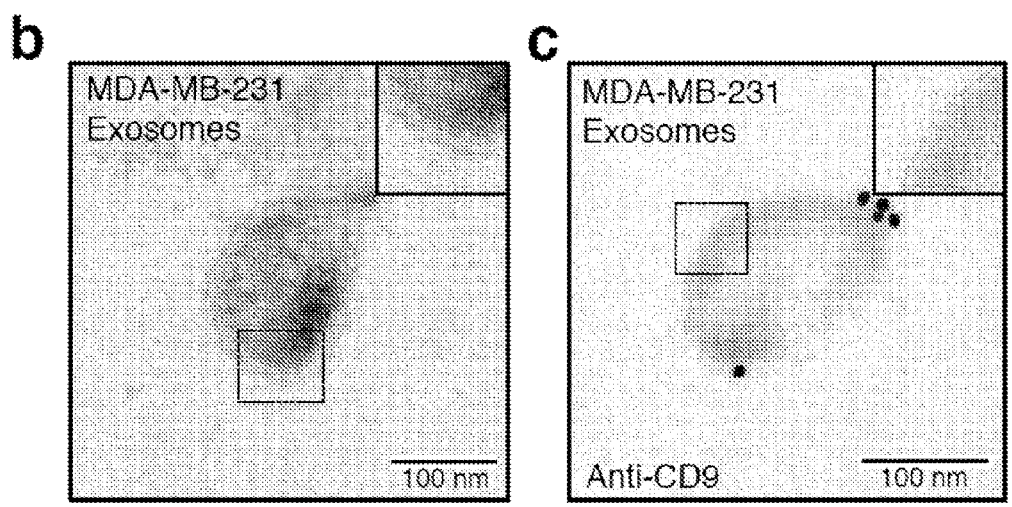
FIGS. 14B-C

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
aaggcctgct gaaaatgact g                                                 21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
tcacaatacc aagaaaccca t                                                 21

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 3
tcctaggttg gctctgac                                                     18

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
```

```
cctgcttgct tacctcgct                                            19

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
ttcctcttcc tacagtactc c                                         21

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
cctgcttgct tacctcgct                                            19

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
aaggcctgct gaaaatgact g                                         21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
agaatggtcc tgcaccagta a                                         21

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
tcttcctaca gtactcccct                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gcttgcttac ctcgcttagt                                           20

<210> SEQ ID NO 11
<211> LENGTH: 18
<212> TYPE: DNA
<213> ORGANISM: Artificial Sequence
```

```
<220> FEATURE:
<223> OTHER INFORMATION: Synthetic oligonucleotide

<400> SEQUENCE: 11
taggttggct ctgactgt                                              18

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
gcttgcttac ctcgcttagt                                            20

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
acttgtggta gttggagcag a                                          21

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
acttgtggta gttggagcag t                                          21

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
acttgtggta gttggagctg g                                          21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
ttggatcata ttcgtccaca a                                          21
```

ANALYSIS OF GENOMIC DNA, RNA, AND PROTEINS IN EXOSOMES FOR DIAGNOSIS AND THERANOSIS

This application is a national phase application under 35 U.S.C. § 371 of International Application No. PCT/US2014/068630, filed Dec. 4, 2014, which claims the benefit of U.S. Provisional Patent Application No. 61/911,863, filed Dec. 4, 2013, which is incorporated herein by reference in its entirety.

BACKGROUND OF THE INVENTION

1. Field of the Invention

The present invention relates generally to the fields of genetics, protein biochemistry, and oncology. More particularly, it concerns the use of exosomal genomic DNA and proteins in genetic analysis and treatment.

2. Description of Related Art

Pancreaticoduodenectomy (Whipple procedure) can be curative for PDAC patients if tumors are detected early with clear surgical margins. Due to the late diagnosis of pancreatic cancer, only around 15% of patients present with surgically resectable tumors (Conlon et al., 1996). Studies comparing stage of disease with outcome following surgery suggest that death rates for PDAC would be reduced if the disease were diagnosed at an earlier stage (Bilimoria et al., 2007).

In addition to direct cell-to-cell contact via soluble factors, such as cytokines and chemokines, there is emerging evidence that exosomes play a pivotal role in intercellular communication (Kahlert and Kalluri, 2013). Exosomes are small, membrane-bound vesicles with a size of 40-150 nm (Pan et al., 1985; Trams et al., 1981). They are secreted by many different cell types, such as cancer cells, mesenchymal cells, thrombocytes (Kahlert and Kalluri, 2013; Heijnen et al., 1999; Raposo et al., 1996), immune cells (Thery et al., 2009), platelets (Janowska-Wieczorek et al., 2005), and endothelial cells (Hergenreider et al., 2012). The first step in exosomes biogenesis involves the inward budding from the limiting membrane of late endosomes (Trajkovic et al., 2008). During this process, exosomes are packed with RNA molecules and proteins from the parental cell (Trams et al., 1981; Trajkovic et al., 2008). After the release into the extracellular space, tumor-derived exosomes can transfer proteins and RNAs with oncogenic activity to recipient cells (Kacharzewska et al., 2012; Grange et al., 2011; Peinado et al., 2012). Because exosomes are very stable under different conditions, they can protect their biological cargo against degradation and denaturation in the extracellular environment (Taylor and Gercel-Taylor, 2008). Genomic DNA in circulation is mainly contained in exosomes (Kahlert et al., 2014). Exosomes from astrocytes and glioblastoma cells carry mitochondrial DNA (Guescini et al., 2010). Furthermore, it has been shown that exosomes from glioblastoma cell lines contain small amounts of single-stranded DNA as well as high levels of transposable elements (Balaj et al., 2011).

Exosomes are found in all body fluids of cancer patients, such as serum, saliva, cerebrospinal fluid, bone marrow aspirates, eye exudate/tears, and ascites (Peinado et al., 2012; Lau et al., 2013; Choi et al., 2011). As such, exosomes are promising diagnostic and predictive biomarkers in cancer. However, genetic profiling studies on circulating DNA from cancer patients are confounded by the fact that the isolated DNA represents all cells of the body, thus making mutation and genetic defects challenging (Murtaza et al., 2013; Yong, 2014; Kirk, 2013; Corwley et al., 2013).

Several exosomes markers have been proposed and include members of the tetraspanin family (CD9, CD63, CD81), members of the endosomal sorting complexes required for transport (ESCRT; TSG101, Alix), and heat shock proteins (Hsp60, Hsp70, Hsp90) (Taylor and Gercel-Taylor, 2011). Epithelial tumor cells secrete exosomes carrying the epithelial cell adhesion molecule (EpCAM) (Taylor and Gercel-Taylor, 2008; Silva et al., 2012; Runz et al., 2007). Melanoma-derived exosomes contain the tumor-associated antigen Mart-1 and tyrosinase-related protein-2 (TYRP2) (Peinado et al., 2012; Mears et al., 2004; Andre et al., 2002). Exosomes from gastric cancer, breast cancer, and pancreatic cancer carry members of the human epidermal growth factor receptor (HER) family (Adamczyk et al., 2011; Baran et al., 2010; Ciravolo et al., 2012). However, none of these markers are specific to cancer-derived exosomes and specific isolation of exosomes from the serum of cancer patients remains a challenge due to the lack of specific markers that can be used to identify and distinguish cancer exosomes from exosomes produced by other cells. A marker for cancer-derived exosomes will significantly increase the sensitivity of detection for low frequency mutations in circulation. Thus, a procedure to specifically detect and isolate cancer cell-derived exosomes in circulation is needed.

SUMMARY OF THE INVENTION

Therefore, the present invention provides that exosomes from human serum samples contain double-stranded genomic DNA that spans all chromosomes and may be used to determine the mutation status of, for example, KRAS and p53. In addition, the present invention provides methods to identify and isolate cancer cell-derived exosomes, such as, for example, based on the exosomes surface marker Glypican-1 (GPC1). Furthermore, the present invention provides that exosomes may be used to produce and deliver therapeutic proteins or nucleic acids (e.g., interfering RNA) to diseased cells.

In one embodiment, the present invention provides a method of isolating genomic double-stranded DNA from a subject comprising (a) obtaining a sample from a patient; (b) isolating an exosomes fraction of the sample; and (c) isolating genomic double-stranded DNA from the exosomes fraction. In some aspects, step (b) may comprise isolating exosomes comprising glypican 1 (GPC1).

In some aspects, the method may comprise performing sequence analysis of the DNA, for example determining a mutation status of a gene (e.g., KRAS or p53). In some aspects, the mutation status may be a cancer biomarker. In some aspects, the presence of the cancer biomarker may be used to diagnose the patient as having cancer. In some aspects, the method may comprise reporting the mutation status of the gene and/or the diagnosis of the patient. In some aspects, reporting may comprise preparing a written or electronic report. In some aspects, reporting may comprise providing the report to the patient, a doctor, a hospital or an insurance company.

In some aspects, the sample may be lymph, saliva, urine, serum, or cerebrospinal fluid. In some aspects, the sample may be essentially free of cells.

In some aspects, the subject may have cancer, such as breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer. In some aspects, the cancer may be pancreatic ductal adenocarcinoma. In some aspects, the subject may have previously been treated for a cancer. In some aspects, the subject may have previously had a tumor surgically removed.

In one embodiment, the present invention provides a method of identifying a cancer biomarker in a subject comprising (a) isolating genomic DNA in accordance with the embodiments of the invention; (b) performing sequence analysis of the genomic DNA; (c) determining the mutation status of at least one gene, thereby identifying a cancer biomarker. In some aspects, step (c) may comprise determining the mutation status of at least two genes.

In some aspects, the presence of the cancer biomarker may diagnose the patient has having cancer. The cancer may be any type of cancer, such as a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer. In one aspect, the cancer may be pancreatic ductal adenocarcinoma. In some aspects, the subject may have previously been treated for a cancer. In some aspects, the subject may have previously had a tumor surgically removed.

In some aspects, the method may comprise reporting the mutation status of the gene and/or the diagnosis of the patient. In some aspects, reporting may comprise preparing a written or electronic report. In some aspects, reporting may comprise providing the report to the patient, a doctor, a hospital or an insurance company.

In one embodiment, the present invention provides a method of treating a cancer in a subject comprising, identifying a subject as having a cancer biomarker in accordance with the embodiments of the invention and administering an anti-cancer therapy to the subject. In some aspects, the anti-cancer therapy may be a chemotherapy, a radiation therapy, a hormonal therapy, a targeted therapy, an immunotherapy or a surgical therapy. In one aspect, the subject may be a human.

In one embodiment, the present invention provides a method of treating a disease in a patient in need thereof comprising (a) obtaining exosomes from a sample; (b) transfecting the exosomes with a nucleic acid encoding a therapeutic protein; and (c) providing the transfected exosomes to a patient, thereby treating the disease in the patient. In some aspects, the exosomes may be autologous to the patient. In some aspects, the disease may be cancer.

In one embodiment, the present invention provides a method of administering a therapeutic protein to a patient in need thereof comprising (a) obtaining exosomes from a sample; (b) transfecting the exosomes with a nucleic acid encoding a therapeutic protein; (c) incubating the exosomes under conditions to allow for expression of the therapeutic protein within the exosomes; and (d) providing the incubated exosomes to a patient, thereby administering a therapeutic protein to the patient. In some aspects, the exosomes may be autologous to the patient.

In one embodiment, the present invention provides a method of treating a disease in a subject comprising, identifying a subject as having a cancer biomarker in accordance with the present embodiments and administering a therapeutic protein to the subject in accordance with the present embodiments. In one aspect, the cancer biomarker may be a p53 mutation and the therapeutic protein may be wild-type p53. In another aspect, the cancer biomarker may be a KRAS mutation and the therapeutic protein may be wild-type KRAS.

In one embodiment, the present invention provides a method of producing a recombinant protein comprising (a) obtaining exosomes from a sample; (b) transfecting the exosomes with a nucleic acid encoding a recombinant protein; and (c) incubating the exosomes under conditions to allow for expression of the recombinant protein, thereby producing the recombinant protein.

In some aspects, the method may comprise purifying the recombinant protein. In certain aspects, the method may comprise administering the purified, recombinant protein to a patient in need thereof. In some aspects, the method may comprise administering the incubated exosomes to a patient in need thereof. In some aspects, the exosomes may be autologous to the patient. In one aspect, the patient may have been diagnosed with cancer.

In some aspects of the embodiment, a sample may be a tissue culture media sample. In other aspects of the embodiments, a sample may be a body fluid sample (e.g., lymph, saliva, urine, cerebrospinal fluid, bone marrow aspirates, eye exudate/tears, or serum). In certain aspects, the body fluid sample, and thus the exosomes obtained therefrom, may be obtained from the patient undergoing the method of treatment.

In some aspects of the embodiments, the nucleic acid may be an mRNA. In some aspects of the embodiments, the nucleic acid may be a plasmid.

In one embodiment, the present invention provides a purified recombinant protein produced according to a method of the embodiments.

In one embodiment, the present invention provides a method of isolating cancer cell-derived exosomes comprising (a) obtaining a body fluid sample from a cancer patient; (b) isolating an exosomes fraction of the body fluid sample; and (c) isolating exosomes comprising glypican 1 from the exosomes fraction, thereby isolating cancer cell-derived exosomes. In some aspects, the method may comprise isolating genomic double-stranded DNA, RNA, or proteins from the cancer cell-derived exosomes. In some aspects, the method may comprise detecting the presence of a particular DNA sequence, RNA sequence, or protein in the cancer cell-derived exosomes. In some aspects, detecting a particular DNA sequence may comprise detecting a particular mutation or defect in a DNA sequence. In some aspects, detecting a particular DDA sequence may comprise detecting a particular epigenetic state of the DNA sequence. In some aspects, detecting a particular RNA sequence may comprise detecting a particular mutation or defect in a RNA sequence. In some aspects, detecting a protein may comprise detecting a defective protein, such as, for example, a mutated protein, an addition mutation protein, a deletion mutation protein, a modified protein (e.g., a protein with an altered state of post-translational modification), or a truncated protein. In some aspects, detecting a protein may comprise detecting an epigenetic change.

In certain aspects, the isolating of step (b) or (c) may comprise immunomagnetic capture, adhesion-based sorting, magnetic-activated sorting, or fluorescence-activated sorting (FACS). In some aspects, the method may comprise quantifying the number of cancer cell-derived exosomes in the patient. In some aspects, the method may comprise genotyping the cancer cell-derived exosomes.

In certain aspects, the body fluid sample may be lymph, saliva, urine, or serum. In certain aspects, the cancer may be a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer.

In one embodiment, the present invention provides a method of diagnosing cancer in a patient comprising (a) obtaining a body fluid sample from a patient; (b) isolating an exosomes fraction of the body fluid sample; and (c) assaying for the presence of glypican 1 in the exosomes fraction, wherein if glypican 1 is present, then the patient is diagnosed as having cancer. In some aspects, the method may comprise quantifying the number of glypican 1-containing exosomes in the patient. Quantifying the number of glypican 1-containing exosomes in the patient may comprise, for example, immunoaffinity capture, cytometric analysis, or ELISA.

In some aspects, the method may be defined as a method of monitoring response to therapy in a cancer patient, wherein if the number of glypican 1-containing exosomes decreases over time, then the patient is said to have had a positive response to therapy. In some aspects, the patient may not have been previously diagnosed with cancer and the method may be a method of early cancer detection. In some aspects, the patient may be in remission and the method may be a method of detecting relapse. In one aspect, the method may comprise administering an anti-cancer therapy to the patient.

In certain aspects, the body fluid sample may be lymph, saliva, urine, cerebrospinal fluid, bone marrow aspirates, eye exudate/tears, or serum. In certain aspects, the cancer may be a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer.

In some aspects, the method may comprise reporting the diagnosis of the patient. In some aspects, reporting may comprise preparing a written or electronic report. In some aspects, reporting may comprise providing the report to the patient, a doctor, a hospital or an insurance company.

In some embodiment, the present invention may provide a kit for use in isolating exosomes from a sample, isolating genomic DNA from exosomes, isolating cancer cell-derived exosomes, quantifying the number of cancer cell-derived exosomes in a sample and/or patient, expressing a recombinant protein in exosomes, treating a patient with a recombinant protein expressed in exosomes, and/or treating a patient with exosomes expressing a recombinant protein.

In one embodiment, a composition is provided comprising exosomes transfected with a nucleic acid encoding a therapeutic protein for use in the treatment of a disease in a patient. In some aspects, the disease may be a cancer. In some aspects, the exosomes may be autologous to the patient. In some aspects, the exosomes may have been incubated under conditions to allow for expression of the therapeutic protein within the exosomes. In some aspects, the patient may have been identified as having a cancer biomarker according to the present embodiments. In some aspects, the cancer biomarker may be a p53 mutation and the therapeutic protein may be wild-type p53.

In one embodiment, the use of exosomes transfected with a nucleic acid encoding a therapeutic protein in the manufacture of a medicament for the treatment of a disease is provided. In some aspects, the disease may be a cancer.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. The presence and concentration of exosomes from human pancreatic cancer cell lines and human serum samples from patients with pancreatic cancer were determined using a NanoSight® LM10 (FIG. 1A) and electron microscopy (FIG. 1B). FIG. 1C. Exosomes were characterized by the exosomes-specific expression of TSG 101 by western blotting. FIG. 1D. To exclude RNA contamination after exosomes lysis and DNA extraction, the DNA eluate from two cell lines (Panc-1 and T3M4) and the DNA eluate from corresponding exosomes was treated with DNAse I and RNAse A. Subsequently, the eluate was run on a 2% agarose gel. FIG. 1E. The presence of double-stranded DNA from Panc-1 exosomes and human serum exosomes from patients with and without pancreatic cancer was confirmed by a double-stranded DNA detection kit (representative figure for exosomal DNA from Panc-1, one healthy donor, and one patient with pancreatic cancer). FIG. 1F. Exosomes were characterized by the exosomes-specific expression of TSG 101 and CD63 by western blotting.

FIGS. 2A-E. Exosomes contain mutated KRAS and p53 DNA. FIG. 2A. A 466 bp fragment of KRAS spanning exon 2 and intron 2 and a 1564 bp fragment of p53 spanning 4 exons and 3 introns were amplified by PCR. FIG. 2B. Sanger sequencing of genomic DNA from Panc-1 cells and corresponding exosomes revealed the same heterozygous mutation of KRAS on codon 12 (GGT to GAT) and the similar homozygous mutation of p53 on codon 273 (CGT to CAT). T3M4 cells and corresponding exosomes displayed the same homozygous mutation of p53 on codon 220 (TAT to TGT). FIG. 2C. PCR amplification provided evidence for long fragments of DNA in circulating exosomes from two patients with pancreatic cancer. A 466 bp fragment of KRAS DNA and 609 bp fragment of p53 DNA spanning exons 7 and 8 and intron 7 were retrieved. When serum samples depleted of exosomes were subjected to PCR, no KRAS or p53 amplicon was detected. FIG. 2D. Sanger sequencing of serum exosome-derived DNA detected DNA with a KRAS mutation in codon 22. In a second patient, Sanger sequencing revealed a KRAS mutation in codon 12 and a p53 mutation in codon 273. FIG. 2E. PCR amplification provided evidence for long fragments of DNA in circulating exosomes from two healthy donors and two patients with pancreatic cancer.

FIG. 4A. Particle tracking analysis using NanoSight® technology. Left image shows a snapshot of a movie of exosomes. Right graph shows the integrated analysis of the size distribution of exosomes and their concentration. FIG. 4B. Electron microscopy showing images of exosomes collected from culture media. FIG. 4C. Immunogold staining of exosomes collected from culture media using anti-CD9 antibody, an exosomes marker. FIG. 4D. Flow cytometry analysis of exosomes collected from culture media using anti-CD9 antibody. FIG. 4E Immunoblot analysis using CD9 and CD63 exosomes markers to show the presence of exosomes in the media collected from several different cell lines.

FIG. 5A. Northern blot of tRNAs of exosomes derived from different cell lines. FIG. 5B. HeatMap of mass spectrometry analysis showing the presence of amino acids in exosomes extracted from different cell lines. FIG. 5C. Quantitative RT-PCR of 18S and 28S rRNAs in exosomes derived from different cell lines. Each sample in the legend, from top to bottom, represents each bar on the graph in order from left to right. FIG. 5D Immunoblot analysis of eukaryotic translation initiation factor 3A, 4A1 and 1A in protein extracts of different exosomes. CD9 was used as an exosomes marker to show the presence of exosomes. FIG. 5E Immunoprecipitation of eukaryotic translation initiation factor 4A1 followed by immunoblot of eukaryotic translation initiation factor 4A1 and 3A showing interaction between these two proteins in exosomes.

FIG. 6A. In vitro translation assay using protein extracts from exosomes and cells as a positive control and a GFP vector. Protein lysate from the in vitro translation assay kit was used as a second positive control. GADPH was used as a loading control. FIG. 6B Immunogold staining of exosomes electroporated with GFP vector using a GFP antibody. Upper panels show negative controls and lower panels show GFP staining in exosomes. FIG. 6C. Autoradiography of exosomes cultured with [$^{35}$S] methionine. Cycloheximide and cells were used as negative and positive controls, respectively.

FIG. 8A. Graphical representation of mass spectrometry results on glypican 1 in exosomes from culture media of E10, NIH-3T3, HDF, MCF10A and MDA-MB231 cells. FIG. 8B. Glypican 1 western of exosomes extracted from non-tumorigenic breast epithelial cells (MCF10A) and breast cancer cells (MCF7 and MDA-MB231). FIG. 8C. Flow cytometry analysis of exosomes derived from non-tumorigenic breast epithelial cells (MCF10A) and breast cancer cells (MDA-MB231).

FIG. 9A. Immunogold transmission electron micrographs of GPC1 in non-tumorigenic cell line-derived exosomes (HMLE) (left panel) and in pancreatic cancer-derived exosomes (T3M4) (right panel). Gold particles are depicted as black dots. Upper right images show a digital zoomed inset. FIG. 9B. Schematic representation of the FACs analysis of GPC1 on the surface of exosomes. FIG. 9C. Transmission electron micrographs (TEM) of exosomes coupled to aldehyde/sulphate beads (left panel) Immunogold labeling of GPC1 in T3M4 and HMLE exosomes coupled to aldehyde/sulphate beads (two bottom panels). Gold particles are depicted as black dots. Negative control was performed using secondary antibody only (top right). FIG. 9D. Graph representing the percent of GPC1$^+$ exosomes from cancer cells (gray) and from non-tumorigenic cells (black). FIG. 9E. Representative histograms of FACS analysis of GPC1$^+$ exosomes coupled to aldehyde/sulphate beads from HMLE, HMEL, MDA-MB-231, T3M4, PANC-1, and MIA PaCa2 isolated by ultracentrifugation.

FIG. 10A. Schematic diagram of the longitudinal blood collection from nude mice with orthotopically injected MDA-MB-231 cells. Blood samples were obtained prior to tumor cell injection and when the tumor volume reached 300, 550, 1000, and 1350 mm$^3$. FIG. 10B. Representative scatter plots for FACS analysis of GPC1$^+$ crExos from nude mice with MDA-MB-231 tumors of the indicated volumes. FIG. 10C. Correlation between tumor volume and percentage (%) of GPC1$^+$ crExos in nude mice with orthotopically injected MDA-MB-231 cells (Pearson correlation test, Correlation coefficient r=0.98, P=0.004). FIG. 10D. NanoSight® coupled with a 488 laser of exosomes derived from MDA-MB-231 CD63-GFP cells. Black line represents the tracking analysis without a 488 laser and the gray line represents the analysis with a 488 laser. FIG. 10E. NanoSight® of crExos from MDA-MB-231-CD63-GFP-injected mice. Black line represents the tracking analysis without a 488 laser and the gray line represents the tracking analysis with a 488 laser. FIG. 10F. Co-localization study for the overlapping expression of CD63-GFP and GPC1 in crExos. FACS analysis assessed exosomes derived from MDA-MB-231 cells as a negative control (left upper panel), exosomes derived from MDA-MB-231 CD63-GFP cells as a positive control (middle upper panel), and exosomes derived from mice injected with MDA-MB-231 CD63-GFP cells and analyzed using an Alexa 594 conjugated secondary antibody only as a negative control (right upper panel). FACS analysis shows that only the fraction of CD63-GFP$^+$ exosomes, derived from mice orthotopically injected with MDA-MB-231 CD63-GFP, were positive for GPC1 (three bottom graphs).

FIGS. 11A-I. GPC1+ crExos are a non-invasive biomarker for pancreatic cancer. FIG. 11A. TEM of crExos from a patient with pancreatic cancer. Upper right image shows a digitally zoomed inset. FIG. 11B. TEM image of crExos immunogold labeled for CD9. Gold particles are depicted as black dots. Upper right image shows a digitally zoomed inset. FIG. 11C. Scatter plots representative of FACS analysis of GPC1+ crExos in healthy donors (n=100), breast cancer patients (n=32), and patients with pancreatic ductal adenocarcinoma (PDAC; n=190) (analysis of variance (ANOVA), **P<0.0001). FIG. 11D. Bar graph representative of the KRAS status of 47 patients with pancreatic cancer. FIG. 11E. TEM of crExos from three patients with pancreatic cancer. Prior to immunogold labeling of GPC1, exosomes were separated using FACS into GPC1+ (left column) and GPC1− (right column) populations. Gold particles are depicted as black dots. FIG. 11F. Scatter plots representative of KRAS G12D, KRAS wild-type mRNA, and 18S rRNA expression (left panel) or KRAS G12V, KRAS wild-type mRNA, and 18s rRNA expression (right panel) in exosomes that have been separated by FACS into GPC1+ (+; gray) and GPC1− (−; black) populations. FIG. 11G. Scatter plots representative for FACS analysis of GPC1+ crExos in healthy donors (n=100), patients with a benign pancreatic disease (BPD; n=26), patients with a pancreatic cancer precursor lesion (PCPL; n=7) and patients with PDAC (n=190; analysis of variance (ANOVA), P<0.01, ****P<0.0001). FIG. 11H. Scatter plots representative of ELISA assay of serum CA 19-9 in the same cohort of patients with pancreatic cancer as in FIG. 11E (ANOVA, *P<0.05, ****P<0.0001). FIG. 11I. Receiver Operating Characteristic (ROC) curve analysis for GPC1+ crExos (gray line), CA 19-9 (dashed gray line), exosomes concentration (black line), and exosomes size (dashed black line) in patients with pancreatic cancer (n=190) vs. control (healthy donors (n=100) and patients with a benign pancreatic disease (n=26), total n=126). Abbreviations: Area under the curve (AUC), confidence interval (CI), nanometer (nm).

FIG. 12A. Schematic diagram to illustrate the blood collection of patients in the longitudinal cohort. Blood samples were obtained prior to surgery (pre-op) and post-operative at day 7 after surgery. FIG. 12B. Scatter plots representative for FACS analysis of GPC1+ crExos after resection in patients of the longitudinal cohort with BPD (n=4), PCPL (n=4), or PDAC (n=29) (paired two-tailed Student's t-test, P<0.01, **P<10001). FIG. 12C. Kaplan-Meier curves (log-rank test) displaying overall survival of patients with a drop of GPC1+ crExos≥the median decrease (top line) and a drop of GPC1+ crExos<the median decrease (bottom line) after resection (P=0.016). FIG. 12D. Kaplan-Meier curves (log-rank test) displaying disease-specific survival of patients with a drop of GPC1+ crExos-≥the median decrease (top line) and a drop of GPC1+ crExos<the median decrease (bottom line) after resection (P=0.007). FIG. 12E Kaplan-Meier curves (log-rank test) displaying overall survival of patients with a drop of CA 19-9≥the median decrease (top line) and a drop of CA 19-9<the median decrease (bottom line) between day 0 and day 7 (P=0.120). FIG. 12F. Kaplan-Meier curves (log-rank test) displaying disease-specific survival of patients with a drop of CA 19-9≥the median decrease (top line) and a drop of CA 19-9<the median decrease (bottom line) between day 0 and day 7 (P=0.180).

FIG. 13A. Schematic diagram to illustrate the blood collection from Ptfla$^{cre/+}$; LSL-Kras$^{G12D/+}$; Tgfbr2$^{flox/flox}$ (PKT) mice and control mice in the longitudinal cohort. Blood samples were obtained at the age of 4, 5, 6, 7, and 8 weeks prior to euthanasia. FIG. 13B. Scatter plots representative for FACS analysis of GPC1+ crExos in PKT mice (E) and control mice (C) measured at 4, 5, 6, 7, and 8 weeks of age (analysis of variance (ANOVA), ****P<0.0001). FIG. 13C. Correlation between tumor volume and GPC1+ crExos in PKT mice (Pearson correlation test, Correlation coefficient r=0.67, P=0.0005). FIG. 13D. Receiver Operating Characteristic (ROC) curve analysis for GPC1+ crExos (gray line), exosomes concentration (black line), and exosomes size (dashed line) in PKT mice at 4 weeks of age (n=7) vs. control (control littermate (n=6) and mice with induced acute pancreatitis (n=4; total n=10). FIG. 13E. Schematic diagram to illustrate the blood collection from PKT mice and control mice in the cross sectional study. Blood samples were obtained at the age of 16 days or at 20 days prior to euthanasia. FIG. 13F. Scatter plots representative for FACS analysis of GPC1+ exosomes in PKT mice and control mice of the cross-sectional study. Mice were sacrificed between the age of 16-20 days (paired two-tailed Student's t-test, P<0.0001). FIG. 13G. Scatter plots representative for quantity of PanIN lesions diagnosed in PKT mice and control between the age of 16-20 days (left panel).

FIGS. 14A-H. Exosomes isolation. FIG. 14A. NanoSight® analysis shows the exosomes size distribution and concentration of NIH/3T3, MCF 10A, HDF, MDA-MB-231 and E10 cells with a modal size of 105 nanometers (nm). FIG. 14B. Transmission electron micrograph (TEM) of MDA-MB-231-derived exosomes. Upper right image shows a digitally zoomed inset. FIG. 14C Immunogold and TEM of MDA-MB-231-derived exosomes of CD9. Gold particles are depicted as black dots. Upper right image shows a digitally zoomed inset. FIG. 14D Immunoblot of flotillin1 and CD81 in exosomal proteins extracted from E10, NIH/3T3, MDA-MB-231, MCF 10A and HDF cells. FIG. 14E. RT-qPCR measurement of GPC1 mRNA in HMEL, HDF, HMLE, MCF7, MDA-MB-231, T3M4, PANC-1, MIA PaCa2. Results are shown as mean±standard deviation (two-tailed Student's t-test, P<0.05). FIG. 14F. Immunoblot of GPC1 in HMEL, HDF, HMLE, MCF7, MDA-MB-231, T3M4, PANC-1 and MIA PaCa2 cell lines (upper panel). β-actin was used as a loading control (lower panel). FIG. 14G. Immunoblot of GPC1 to show protein expression in exosomes derived from three non-tumorigenic cell lines (HDF, HMEL, HMLE) and five tumorigenic cell lines (MCF7, MDA-MB-231, T3M4, PANC-1, MIA PaCa2) (upper panel). Immunoblot of flotillin1 as loading control (lower panel). FIG. 14H Immunoblot of flotillin1 in different layers of a sucrose gradient to which MDA-MB-231 and T3M4-derived exosomes were subjected.

FIG. 15A. Immunoblot of flotillin1 of proteins extracted from different layers of a sucrose gradient to which patient serum-derived exosomes were subjected. FIG. 15B. NanoSight® analysis shows the concentration of circulating exosomes (number of exosomes/1 mL serum) derived from healthy donors (n=100), from breast cancer patients (n=32), and from patients with PDAC (n=190) (analysis of variance (ANOVA), *P<0.05, **P<0.0001). FIG. 15C. NanoSight® analysis shows the size of circulating exosomes derived from healthy donors (n=100), from breast cancer patients (n=32), and from patients with PDAC (n=190) (analysis of variance (ANOVA), *P<0.001).

FIG. 16A. Receiver Operating Characteristic (ROC) curve analysis for GPC1+ crExos (gray line), CA 19-9 (gray dashed line), exosomes concentration (black line), and exosomes size (black dashed line) in patients with carcinoma in situ (CIS) or stage I pancreatic cancer (n=5) vs. control (healthy donors (n=100) and patients with a benign pancreatic disease (n=26, total n=126)). FIG. 16B. ROC curve analysis for GPC1$^+$ crExos (gray line), CA 19-9 (gray dashed line), exosomes concentration (black line), and exosomes size (black dashed line) in patients with stage IIa pancreatic cancer (n=18) vs. control (healthy donors (n=100) and patients with a benign pancreatic disease (n=26), total n=126). FIG. 16C. ROC curve analysis for GPC1$^+$ crExos (gray line), CA 19-9 (gray dashed line), exosomes concentration (black line), and exosomes size (black dashed line) in patients with stage IIb pancreatic cancer (n=117) vs. control (healthy donors (n=100) and patients with a benign pancreatic disease (n=26, total n=126)). FIG. 16D. ROC curve analysis for GPC1$^+$ crExos (gray line), CA 19-9 (gray dashed line), exosomes concentration (black line), and exosomes size (black dashed line) in patients with stage III pancreatic cancer (n=11) vs. control (healthy donors (n=100) and patients with a benign pancreas disease (n=26, total n=126)). FIG. 16E. ROC curve analysis for GPC1$^+$ crExos (gray line), CA 19-9 (gray dashed line), exosomes concentration (black line), and exosomes size (black dashed line) in patients with stage IV pancreas cancer (n=41) vs. control (healthy donors (n=100) and patients with a benign pancreatic disease (n=26, total n=126)). (Abbreviations: Area under the curve (AUC), confidence interval (CI), nanometer (nm)).

FIG. 17A. Scatter plots representative for FACS analysis of GPC1$^+$ crExos in patients with pancreatic cancer (ANOVA, *P<0.05). FIG. 17B. Scatter plots representative for ELISA assay of serum CA 19-9 (U/mL) at the preoperative day and postoperative day 7 in patients of the longitudinal cohort with benign pancreas disease (BPD) (n=4), pancreatic cancer precursor lesion (PCPL) (n=4), and pancreatic ductal adenocarcinoma (PDAC) (n=29) (paired two-tailed Student's t test, **P<0.01).

FIG. 18A. Scatter plots representative for NanoSight® analysis of exosomes size in PKT mice (E) and control mice (C) measured at 4, 5, 6, 7, and 8 weeks of age (analysis of variance (ANOVA), *P<0.05). FIG. 18B. Scatter plots representative for NanoSight® analysis of exosomes concentration in PKT mice (E) and control mice (C) measured at 4, 5, 6, 7, and 8 weeks of age (ANOVA, *P<0.05). (Abbreviations: Control (C), Experimental (E)). FIG. 18C. Graph showing tumor volume measured by MRI and % GPC1$^+$ crExos in individual PKT mice iver time (circles with dashed lines: tumor volume; squares with solid lines: % GPC1$^+$ crExos). FIG. 18D. Scatter plots representative for FACS analysis of GPC1$^+$ crExos in control mice (n=3) and mice with Cerulin-induced acute pancreatitis (n=4) (two-tailed Student's t-test, ns=P>0.05).

Figure 1A:
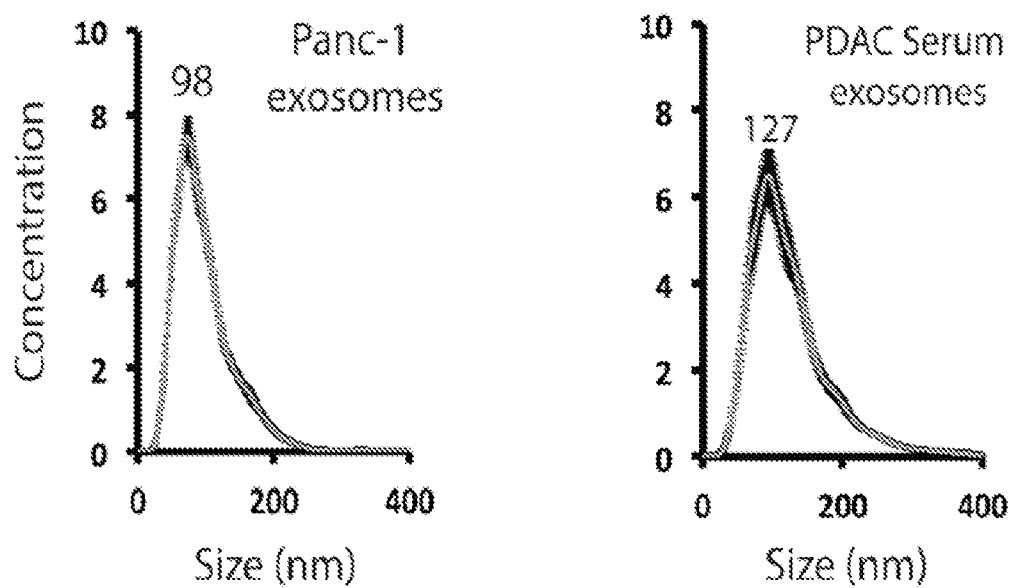
FIGS. 1A-F. Exosomes contain long fragments of double-stranded genomic DNA.

DESCRIPTION OF ILLUSTRATIVE
EMBODIMENTS

Exosomes are small vesicles (40-150 nm) of endocytic origin that are released by many different cell types. Exosomes in the tumor microenvironment may play a key role in facilitating cell-cell communication. Exosomes are reported to predominantly contain RNA and proteins. As taught herein, exosomes from pancreatic cancer cells and serum of patients with pancreatic ductal adenocarcinoma contain genomic DNA.

Herein, exosomes were found to contain long fragments of double-stranded genomic DNA, which contradicts the current opinion that circulating DNA is highly fragmented with an estimated length of only 60-100 bp (Mouliere and Thierry, 2012). Mutations in KRAS and p53 may be detected using genomic DNA from exosomes derived from pancreatic cancer cell lines and serum of patients with pancreatic cancer. In addition, serum exosomes from patients with pancreatic cancer contain genomic DNA spanning all chromosomes and exosomes-derived DNA carry mutations identical to their parental cancer cells or tumors. These results indicate that serum-derived exosomes may be used to determine genomic DNA mutations to predict prognosis of cancer patients and improve treatment via a personalized medicine approach whereby the detection of specific mutations may be used to tailor treatment. As an example, KRAS mutations and EGFR amplifications are predictive of resistance to cetuximab, a drug proven to be efficient in some cases of metastatic colorectal cancer (Lievre et al., 2006). In addition, cancer patients with a KRAS mutation in their tumor do worse on EGFR-targeted therapy using erlotinib.

Also, exosomes were found to have the ability to perform mRNA transcription and protein translation. When exosomes were transfected with a plasmid encoding p53, the exosomes were able to express p53 protein and deliver the protein to p53-deficient target cells, thereby increasing p21 expression. These results indicate that exosomes may be used to express and/or deliver therapeutic proteins to diseased cells.

Using ultra performance liquid chromatography followed by mass spectrometry (UPLC-MS) on exosomes derived from normal and cancer cells, a cell surface proteoglycan, glypican-1, was found to be specifically enriched on the surface of cancer cell-derived exosomes. Circulating GPC1$^+$ exosomes (GPC1$^+$ crExos) were monitored and isolated using flow cytometry (FACS) from the serum of cancer patients and mice with cancer. GPC1$^+$ crExos were detected in the serum of patients with pancreatic cancer with absolute specificity and sensitivity, distinguishing healthy subjects and patients with a benign pancreatic disease from patients with early and late stage pancreatic cancer. Levels of GPC1$^+$ crExos paralleled tumor burden in comparative analyses of serum from patients pre- and post-surgical tumor resection. GPC1$^+$ crExos from patients and a genetically engineered mouse model (GEMM) with spontaneous pancreas tumors driven by pancreas specific KRAS$^{G12D}$ specifically contained RNA with KRAS$^{G12D}$ mutations. GPC1$^+$ crExos served as a reliable biomarker for the detection of early PanIN lesions despite a negative signal by MRI. GPC1$^+$ crExos can be used to specifically detect cancer exosomes in circulation and are a non-invasive diagnostic and screening tool to detect early stages of pancreatic cancer that could aid in the prospect of curative surgical therapy. Furthermore, isolation of glypican 1-positive exosomes provides a means to isolate cancer cell-derived genomic DNA, RNA, and/or proteins.

I. Exosomes

The terms "microvesicle" and "exosomes," as used herein, refer to a membranous particle having a diameter (or largest dimension where the particles is not spheroid) of between about 10 nm to about 5000 nm, more typically between 30 nm and 1000 nm, and most typically between about 50 nm and 750 nm, wherein at least part of the membrane of the exosomes is directly obtained from a cell. Most commonly, exosomes will have a size (average diameter) that is up to 5% of the size of the donor cell. Therefore, especially contemplated exosomes include those that are shed from a cell.

Exosomes may be detected in or isolated from any suitable sample type, such as, for example, body fluids. As used herein, the term "sample" refers to any sample suitable for the methods provided by the present invention. The sample may be any sample that includes exosomes suitable for detection or isolation. Sources of samples include blood, bone marrow, pleural fluid, peritoneal fluid, cerebrospinal fluid, urine, saliva, amniotic fluid, malignant ascites, broncho-alveolar lavage fluid, synovial fluid, breast milk, sweat, tears, joint fluid, and bronchial washes. In one aspect, the sample is a blood sample, including, for example, whole blood or any fraction or component thereof. A blood sample suitable for use with the present invention may be extracted from any source known that includes blood cells or components thereof, such as venous, arterial, peripheral, tissue, cord, and the like. For example, a sample may be obtained and processed using well-known and routine clinical methods (e.g., procedures for drawing and processing whole blood). In one aspect, an exemplary sample may be peripheral blood drawn from a subject with cancer.

Exosomes may also be isolated from tissue samples, such as surgical samples, biopsy samples, tissues, feces, and cultured cells. When isolating exosomes from tissue sources it may be necessary to homogenize the tissue in order to obtain a single cell suspension followed by lysis of the cells to release the exosomes. When isolating exosomes from tissue samples it is important to select homogenization and lysis procedures that do not result in disruption of the exosomes. Exosomes contemplated herein are preferably isolated from body fluid in a physiologically acceptable solution, for example, buffered saline, growth medium, various aqueous medium, etc.

Exosomes may be isolated from freshly collected samples or from samples that have been stored frozen or refrigerated. Although not necessary, higher purity exosomes may be obtained if fluid samples are clarified before precipitation with a volume-excluding polymer, to remove any debris from the sample. Methods of clarification include centrifugation, ultracentrifugation, filtration, or ultrafiltration. Most typically, exosomes can be isolated by numerous methods well-known in the art. One preferred method is differential centrifugation from body fluids or cell culture supernatants. Exemplary methods for isolation of exosomes are described in (Losche et al., 2004; Mesri and Altieri, 1998; Morel et al., 2004). Alternatively, exosomes may also be isolated via flow cytometry as described in (Combes et al., 1997).

One accepted protocol for isolation of exosomes includes ultracentrifugation, often in combination with sucrose density gradients or sucrose cushions to float the relatively low-density exosomes. Isolation of exosomes by sequential differential centrifugations is complicated by the possibility of overlapping size distributions with other microvesicles or macromolecular complexes. Furthermore, centrifugation may provide insufficient means to separate vesicles based on their sizes. However, sequential centrifugations, when combined with sucrose gradient ultracentrifugation, can provide high enrichment of exosomes.

Isolation of exosomes based on size, using alternatives to the ultracentrifugation routes, is another option. Successful purification of exosomes using ultrafiltration procedures that are less time consuming than ultracentrifugation, and do not require use of special equipment have been reported. Similarly, a commercial kit is available (EXOMIR™, Bioo Scientific) which allows removal of cells, platelets, and cellular debris on one microfilter and capturing of vesicles bigger than 30 nm on a second microfilter using positive pressure to drive the fluid. For this process, the exosomes are not recovered, their RNA content is directly extracted from the material caught on the second microfilter, which can then be used for PCR analysis. HPLC-based protocols could potentially allow one to obtain highly pure exosomes, though these processes require dedicated equipment and are difficult to scale up. A significant problem is that both blood and cell culture media contain large numbers of nanoparticles (some non-vesicular) in the same size range as exosomes. For example, some miRNAs may be contained within extracellular protein complexes rather than exosomes; however, treatment with protease (e.g., proteinase K) can be performed to eliminate any possible contamination with "extraexosomal" protein.

In another embodiment, cancer cell-derived exosomes may be captured by techniques commonly used to enrich a sample for exosomes, such as those involving immunospecific interactions (e.g., immunomagnetic capture) Immunomagnetic capture, also known as immunomagnetic cell separation, typically involves attaching antibodies directed to proteins found on a particular cell type to small paramagnetic beads. When the antibody-coated beads are mixed with a sample, such as blood, they attach to and surround the particular cell. The sample is then placed in a strong magnetic field, causing the beads to pellet to one side. After removing the blood, captured cells are retained with the beads. Many variations of this general method are well-known in the art and suitable for use to isolate exosomes. In one example, the exosomes may be attached to magnetic beads (e.g., aldehyde/sulphate beads) and then an antibody is added to the mixture to recognize an epitope on the surface of the exosomes that are attached to the beads.

As used herein, analysis includes any method that allows direct or indirect visualization of exosomes and may be in vivo or ex vivo. For example, analysis may include, but not limited to, ex vivo microscopic or cytometric detection and visualization of exosomes bound to a solid substrate, flow cytometry, fluorescent imaging, and the like. In an exemplary aspect, cancer cell-derived exosomes are detected using antibodies directed to glypican 1 and subsequently bound to a solid substrate and visualized using microscopic or cytometric detection.

II. Diagnosis, Prognosis, and Treatment of Diseases

Detection, isolation, and characterization of cancer cell-derived exosomes, using the methods of the invention, is useful in assessing cancer prognosis and in monitoring therapeutic efficacy for early detection of treatment failure that may lead to disease relapse. In addition, cancer cell-derived exosomes analysis according to the invention enables the detection of early relapse in presymptomatic patients who have completed a course of therapy. This is possible because the presence of cancer cell-derived may be associated and/or correlated with tumor progression and spread, poor response to therapy, relapse of disease, and/or decreased survival over a period of time. Thus, enumeration and characterization of cancer cell-derived exosomes provides methods to stratify patients for baseline characteristics that predict initial risk and subsequent risk based upon response to therapy.

Accordingly, in another embodiment, the invention provides a method for diagnosing or prognosing cancer in a subject. Cancer cell-derived exosomes isolated according to the methods disclosed herein may be analyzed to diagnose or prognose cancer in the subject. As such, the methods of the present invention may be used, for example, to evaluate cancer patients and those at risk for cancer. In any of the methods of diagnosis or prognosis described herein, either the presence or the absence of one or more indicators of cancer, such as a genomic mutation or cancer-specific exosomes surface marker, or of any other disorder, may be used to generate a diagnosis or prognosis.

In one aspect, a blood sample is drawn from the patient and cancer cell-derived exosomes are detected and/or isolated as described herein. For example, the exosomes may be labeled with one or more antibodies that bind to glypican 1, and the antibodies may have a covalently bound fluorescent label. Analysis may then be performed to determine the number and characterization of cancer cell-derived exosomes in the sample, and from this measurement, the number of cancer cell-derived exosomes present in the initial blood sample may be determined. The number of cancer cell-derived exosomes may be determined by cytometric or microscopic techniques to visually quantify and characterize the exosomes. Cancer cell-derived exosomes may be detected and quantifies by other methods known in the art (e.g., ELISA).

In various aspects, analysis of a subject's cancer cell-derived exosomes number and characterization may be made over a particular time course in various intervals to assess a subject's progression and pathology. For example, analysis may be performed at regular intervals such as one day, two days, three days, one week, two weeks, one month, two months, three months, six months, or one year, in order to track the level and characterization of cancer cell-derived exosomes as a function of time. In the case of existing cancer patients, this provides a useful indication of the progression of the disease and assists medical practitioners in making appropriate therapeutic choices based on the increase, decrease, or lack of change in cancer cell-derived exosomes. Any increase, be it 2-fold, 5-fold, 10-fold or higher, in cancer cell-derived exosomes over time decreases the patient's prognosis and is an early indicator that the patient should change therapy. Similarly, any increase, be it 2-fold, 5-fold, 10-fold or higher, indicates that a patient should undergo further testing such as imaging to further assess prognosis and response to therapy. Any decrease, be it 2-fold, 5-fold, 10-fold or higher, in cancer cell-derived exosomes over time shows disease stabilization and a patient's response to therapy, and is an indicator to not change therapy. For those at risk of cancer, a sudden increase in the number of cancer cell-derived exosomes detected may provide an early warning that the patient has developed a tumor thus providing an early diagnosis. In one embodiment, the detection of cancer cell-derived exosomes increases with the staging of the cancer.

In any of the methods provided herein, additional analysis may also be performed to characterize cancer cell-derived exosomes to provide additional clinical assessment. For example, in addition to image analysis and bulk number measurements, PCR techniques may be employed, such as multiplexing with primers specific for particular cancer markers to obtain information such as the type of tumor from which the cancer cell-derived exosomes originated, metastatic state, and degree of malignancy. Additionally, DNA or RNA analysis, proteome analysis, or metabolome analysis may be performed as a means of assessing additional information regarding characterization of the patient's cancer.

For example, the additional analysis may provide data sufficient to make determinations of responsiveness of a subject to a particular therapeutic regime, or for determining the effectiveness of a candidate agent in the treatment of cancer. Accordingly, the present invention provides a method of determining responsiveness of a subject to a particular therapeutic regime or determining the effectiveness of a candidate agent in the treatment of cancer by detecting/isolating cancer cell-derived exosomes of the subject as described herein and analyzing said cancer cell-derived exosomes. For example, once a drug treatment is administered to a patient, it is possible to determine the efficacy of the drug treatment using the methods of the invention. For example, a sample taken from the patient before the drug treatment, as well as one or more samples taken from the patient concurrently with or subsequent to the drug treatment, may be processed using the methods of the invention. By comparing the results of the analysis of each processed sample, one may determine the efficacy of the drug treatment or the responsiveness of the patient to the agent. In this manner, early identification may be made of failed compounds or early validation may be made of promising compounds.

Certain aspects of the present invention can be used to prevent or treat a disease or disorder based on the presence of genetic mutations found in genomic DNA isolated from exosomes. Other aspects of the present invention provide for treating a patient with exosomes that express a recombinant protein or with a recombinant protein isolated from exosomes. Other aspects of the present invention provide for diagnosing a disease based on the presence of cancer cell-derived exosomes in a patient sample.

The term "subject" as used herein refers to any individual or patient to which the subject methods are performed. Generally the subject is human, although as will be appreciated by those in the art, the subject may be an animal. Thus other animals, including mammals, such as rodents (including mice, rats, hamsters, and guinea pigs), cats, dogs, rabbits, farm animals (including cows, horses, goats, sheep, pigs, etc.), and primates (including monkeys, chimpanzees, orangutans, and gorillas) are included within the definition of subject.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of chemotherapy, immunotherapy, or radiotherapy, performance of surgery, or any combination thereof.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

The term "cancer," as used herein, may be used to describe a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The terms "contacted" and "exposed," when applied to a cell, are used herein to describe the process by which a therapeutic agent are delivered to a target cell or are placed in direct juxtaposition with the target cell. To achieve cell killing, for example, one or more agents are delivered to a cell in an amount effective to kill the cell or prevent it from dividing.

An effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Treatment outcomes can be predicted and monitored and/or patients benefiting from such treatments can be identified or selected via the methods described herein.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, the patient's clinical history and response to the agent, and the discretion of the attending physician. The agent is suitably administered to the patient at one time or over a series of treatments.

Therapeutic and prophylactic methods and compositions can be provided in a combined amount effective to achieve the desired effect. A tissue, tumor, or cell can be contacted with one or more compositions or pharmacological formulation(s) comprising one or more of the agents, or by contacting the tissue, tumor, and/or cell with two or more distinct compositions or formulations. Also, it is contemplated that such a combination therapy can be used in conjunction with chemotherapy, radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

A first anti-cancer treatment (e.g., exosomes that express a recombinant protein or with a recombinant protein isolated from exosomes) may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a first anti-cancer therapy is "A" and a second anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid;

capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

III. Pharmaceutical Compositions

It is contemplated that exosomes that express a recombinant protein or a recombinant protein isolated from exosomes can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present invention be limited by the particular nature of the therapeutic preparation. For example, such compositions can be provided in formulations together with physiologically tolerable liquid, gel, solid carriers, diluents, or excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particular requirements of individual subjects.

Where clinical applications are contemplated, it may be necessary to prepare pharmaceutical compositions comprising recombinant proteins and/or exosomes in a form appropriate for the intended application. Generally, pharmaceutical compositions may comprise an effective amount of one or more recombinant proteins and/or exosomes or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition comprising a recombinant protein and/or exosomes as disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

Further in accordance with certain aspects of the present invention, the composition suitable for administration may be provided in a pharmaceutically acceptable carrier with or without an inert diluent. As used herein, "pharmaceutically acceptable carrier" includes any and all aqueous solvents (e.g., water, alcoholic/aqueous solutions, ethanol, saline solutions, parenteral vehicles, such as sodium chloride, Ringer's dextrose, etc.), non-aqueous solvents (e.g., fats, oils, polyol (for example, glycerol, propylene glycol, and liquid polyethylene glycol, and the like), vegetable oil, and injectable organic esters, such as ethyloleate), lipids, liposomes, dispersion media, coatings (e.g., lecithin), surfactants, antioxidants, preservatives (e.g., antibacterial or antifungal agents, anti-oxidants, chelating agents, inert gases, parabens (e.g., methylparabens, propylparabens), chlorobutanol, phenol, sorbic acid, thimerosal or combinations thereof), isotonic agents (e.g., sugars and sodium chloride), absorption delaying agents (e.g., aluminum monostearate and gelatin), salts, drugs, drug stabilizers, gels, resins, fillers, binders, excipients, disintegration agents, lubricants, sweetening agents, flavoring agents, dyes, fluid and nutrient replenishers, such like materials and combinations thereof, as would be known to one of ordinary skill in the art. The carrier should be assimilable and includes liquid, semi-solid, i.e., pastes, or solid carriers. In addition, if desired, the compositions may contain minor amounts of auxiliary substances, such as wetting or emulsifying agents, stabilizing agents, or pH buffering agents. The pH and exact concentration of the various components in a pharmaceutical composition are adjusted according to well-known parameters. The proper fluidity can be maintained, for example, by the use of a coating, such as lecithin, by the maintenance of the required particle size in the case of dispersion, and by the use of surfactants.

A pharmaceutically acceptable carrier is particularly formulated for administration to a human, although in certain embodiments it may be desirable to use a pharmaceutically acceptable carrier that is formulated for administration to a non-human animal but that would not be acceptable (e.g., due to governmental regulations) for administration to a human. Except insofar as any conventional carrier is incompatible with the active ingredient (e.g., detrimental to the recipient or to the therapeutic effectiveness of a composition contained therein), its use in the therapeutic or pharmaceutical compositions is contemplated. In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The therapeutics may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid and the like. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine and the like. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition comprising one or more lipids and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the therapeutic agent may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present invention administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

IV. Nucleic Acids and Vectors

In certain aspects of the invention, nucleic acid sequences encoding a therapeutic protein or a fusion protein containing a therapeutic protein may be disclosed. Depending on which expression system is used, nucleic acid sequences can be selected based on conventional methods. For example, the respective genes or variants thereof may be codon optimized for expression in a certain system. Various vectors may be also used to express the protein of interest. Exemplary vectors include, but are not limited, plasmid vectors, viral vectors, transposon, or liposome-based vectors.

V. Recombinant Proteins

Some embodiments concern recombinant proteins and polypeptides. Particular embodiments concern a recombinant protein or polypeptide that exhibits at least one therapeutic activity. In further aspects, the protein or polypeptide may be modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide. It is specifically contemplated that embodiments concerning a "modified protein" may be implemented with respect to a "modified polypeptide," and vice versa.

Recombinant proteins may possess deletions and/or substitutions of amino acids; thus, a protein with a deletion, a protein with a substitution, and a protein with a deletion and a substitution are modified proteins. In some embodiments, these proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A recombinant protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Certain embodiments of the present invention concern fusion proteins. These molecules may have a therapeutic protein linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the therapeutic protein may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

VI. Protein Purification

Protein purification techniques are well known to those of skill in the art. These techniques involve, at one level, the homogenization and crude fractionation of the cells, tissue, or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulphate, PEG, antibodies and the like, or by heat denaturation, followed by centrifugation; chromatography steps, such as ion exchange, gel filtration, reverse phase, hydroxyapatite, and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified. For example, a His tag or an affinity epitope may be comprised in a recombinant protein to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.).

The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

VII. Kits and Diagnostics

In various aspects of the invention, a kit is envisioned containing the necessary components to purify exosomes from a body fluid and isolate genomic DNA therefrom. The kit may further contain oligonucleotides for use in amplifying a target DNA sequence and/or sequence a target segment of DNA. In other aspects, a kit is envisioned containing the necessary components to isolate exosomes and transfect them with a nucleic acid encoding a therapeutic protein. In yet other aspects, a kit is envisioned containing the necessary components to isolate exosomes and determine the presence of a cancer cell-derived exosome-specific marker within the isolated exosomes.

The kit may comprise one or more sealed vials containing any of such components. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill. The instruction information may be in a computer readable media containing machine-readable instructions that, when executed using a computer, cause the display of a real or virtual procedure of purifying exosomes from a sample and isolating genomic DNA therefrom, expressing a recombinant protein therein, or identifying a cancer cell-derived marker thereon.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Patient Samples and Tissue Collection. The Ethics Committee of the University of Heidelberg approved serum collection from patients. The study was conducted according to the Reporting Recommendations for Tumor Marker Prognostic Studies (REMARK) criteria. Serum samples and tissue samples from patients with pancreatic cancer, serum samples only from patients with a benign pancreatic disease and from healthy donors, who had no evidence of acute or chronic disease and had no surgery within the past 12 months, were received from the department of General, Visceral and Transplantation Surgery from the University of Heidelberg. The pancreatic cohort included 190 patients with an adenocarcinoma of the pancreas (PDAC), 18 patients with pancreatitis, 8 patients with a benign serous cystadenoma, five patients with an intraductal papillary mucinous neoplasm (IPMN), and two patients with a pancreatic intraepithelial neoplasia (PaNIN) Ib. Patients were subjected to surgery between 2006 and 2012 at the Department of General, Visceral, and Transplantation Surgery, University of Heidelberg. Clinical information included age, gender, AJCC tumor stage, tumor size (pT), presence and number of lymph node mestastases (pN), tumor grade (G), and treatment with (neo-)/adjuvant chemotherapy.

Serum samples from 32 patients with breast cancer were collected at the MD Anderson Cancer Center, Houston, Tex. Clinical information included age, gender, AJCC tumor stage, tumor size (pT), presence and number of lymph node mestastases (pN), tumor grade, and treatment with (neo-)/adjuvant chemotherapy.

A written informed consent for the serum sampling and tumor sampling was obtained preoperatively from all patients and from each healthy donor prior to collection with disclosure of planned analyses regarding potential prognostic markers. No neoadjuvant radiotherapy or chemotherapy was provided prior to surgical resection of tumors in the patients. On the day of surgery, 10 mL serum separator tubes were used to collect blood samples through a central venous catheter immediately before surgical incision. To prevent dilution with blocking saline, the first 5-7 mL of the drawn blood were discarded. The blood samples were then centrifuged at 2.500×g for 10 min to extract the serum, and the serum was stored at −80° C. until analysis. Likewise, blood samples were collected on day 7 after surgery in 29 patients with an adenocarcinoma of the pancreas (PDAC), 4 patients with chronic pancreatitis, and 4 patients with an intraductal papillary mucinous neoplasm (IPMN).

Animal Studies.

Nude mice (nu/nu) (purchased from Jackson Laboratory) underwent breast pad injections with 0.5 million MDA-MB-231 cells or MDA-MB-231-CD63GFP cells in 20 µL of PBS injected per breast pad. Buprenorphine was administered subcutaneously (0.1 mg/kg in 0.1 mL saline) once prior to the surgery and every 8-12 h post-operatively for 24 h. Blood was collected retro-orbitally and exosomes were isolated prior to injection and at tumor volumes of 250, 500, 1000, and 1500 mm$^3$. Mice were euthanized when the tumor size reached 1500 mm$^3$ or when severe disease symptoms were present.

The disease progression and genotyping for the Ptflacre/+; LSLKrasG12D/+; Tgfbr2flox/flox (PKT) mice was previously described (Ijichi et al., 2006; Ozdemir et al., 2014). In the longitudinal cohort, retro-orbital blood collection was performed at 4, 5, 6, 7, and 8 weeks of age. Mice were euthanized at an age of 8 weeks or when severe disease symptoms were present. In 4 control littermate without pancreatic cancer, acute pancreatitis was induced by i.p. injections of Cerulean (50 µg/kg body weight once an hour for 5 h (overall: 5 injections). Mice were sacrificed 24 h after injection. All mice were housed under standard housing conditions at the MD Anderson Cancer Center (MDACC) animal facilities, and all animal procedures were reviewed and approved by the MDACC institutional animal care and use committees.

Cell Lines.

The following human cells lines were used: HMLE (American Type Culture Collection (ATCC), Manassas, Va.), BJ (ATCC), HDF (ATCC), HMEL (ATCC), MCF-7 (ATCC), MDA-MB231 (ATCC), PANC-1 (ATCC), SW480 (ATCC), HCT 116 (ATCC), MIA PaCa-2 (ATCC), and T3M4 cells (Cell Bank, RIKEN BioResource Centre, Japan). The following murine cells lines were used: NIH/3T3 (ATCC), E10 (ATCC), NMuMG (ATCC), 4T1 (ATCC), and B16-F10 cells (ATCC). HDF and BJ cells were cultured in DMEM supplemented with 20% (v/v) fetal bovine serum (FBS), 100 U/mL penicillin and 100 µg/mL streptomycin. HMLE and MCF 10A cells were grown in DMEM/F12 supplemented with 5% (v/v) horse serum, 100 U/mL penicillin, 100 µg/mL streptomycin, 20 ng/mL EGF, 0.5 mg/mL hydrocortisone, 100 ng/mL cholera toxin, and 10 µg/mL insulin. HMEL, MCF7, MDA-MB-231, HCT 116, SW480, 4T1, NIH/3T3, E10, U-87, and B16 F10 cells were maintained in DMEM supplemented with 10% (v/v) FBS, 100 U/mL penicillin and 100 µg/mL streptomycin. PANC-1, MIA PaCa-2, and T3M4 cells were cultured in RPMI-1640 (Sigma, St. Louis, Mo.) supplemented with 10% (v/v) FBS, 100 U/mL penicillin, amphotericin B, and 100 µg/mL streptomycin. NMUMG cells were grown in DMEM supplemented with 10% (v/v) FBS, 100 U/mL penicillin, 100 µg/mL streptomycin, and 10 µg/mL insulin. All cell lines were kept in a humidified atmosphere at 5% $CO_2$ and 37° C. Transfections were performed using Lipofectamine® 2000 reagent (Invitrogen) for siRNA. GPC1 siRNA (Cat. Nos. SI00032445, SI00032459, SI00032466, SI03071033) and scramble siRNA were purchased from Qiagen (Hilden, Germany).

Exosomes Isolation from Cells. Exosomes were obtained from supernatant of cells as previously described with some modifications (Kahlert et al., 2014). Briefly, cells were grown in T225 cm$^2$ flasks until they reached a confluency of 80%-90%. Next, the media was collected and centrifuged at 800×g for 5 minutes, followed by a centrifugation step of 2000×g for 10 minutes to discard cellular detritus. Then, the media was filtered using a 0.2 µm pore filter (Syringe filter, Cat. No. 6786-1302, GE Healthcare, GB). Afterwards, the collected media was ultracentrifuged at 100,000×g for 2 h at 4° C. The exosomes pellet was washed with 35 mL 1×PBS, followed by a second step of ultracentrifugation at 100,000×g for 2 h at 4° C. Afterwards, the supernatant was discarded. Exosomes used for RNA extraction were resuspended in 500 µL of TRIzol®; exosomes used for protein extraction were resuspended in 250 µL of lysis buffer (8 M urea/2.5% SDS, 5 µg/mL leupeptin, 1 µg/mL pepstatin, and 1 mM phenylmethylsulphonyl fluoride (PMSF)). Exosomes used for flow cytometry analysis (FACS), transmission electron microscopy (TEM), and immunogold staining were resuspended in 100 µL 1×PBS. Ten microliters of this sample were diluted at 1:100 in 1×PBS and analyzed using a NanoSight® LM10 (NanoSight Ltd., Minton Park, Amesbury, GB).

Exosomes Isolation from Human Serum Samples. As previously described, 250 µL of cell-free serum samples were thawed on ice (Kahlert et al., 2014). Serum was diluted in 11 mL 1×PBS and filtered through a 0.2 µm pore filter. Afterward, the samples were ultracentrifuged at 150,000×g overnight at 4° C. Next, the exosomes pellet was washed in 11 mL 1×PBS followed by a second step of ultracentrifugation at 150,000×g at 4° C. for 2 h. Afterwards, the supernatant was discarded. Exosomes used for RNA extraction were resuspended in 500 µL of TRIzol®; exosomes used for protein extraction were resuspended in 250 µL of lysis buffer (8 M Urea/2.5% SDS, 5 µg/mL leupeptin, 1 µg/mL pepstatin, and 1 mM PMSF). Exosomes used for FACS, TEM, and immunogold staining were resuspended in 100 µL 1×PBS. Ten microliters of this sample were diluted at 1:100 in 1×PBS and analyzed using a NanoSight® LM10 (NanoSight Ltd., Minton Park, Amesbury, GB).

Flow Cytometry Analysis of Exosomes. Exosomes were attached to 4 µm aldehyde/sulfate latex beads (Invitrogen, Carlsbad, Calif., USA) by mixing ~30 µg exosomes in a 100 µL volume of beads for 1 h at room temperature. This suspension was diluted to 1 mL with 1×PBS, and the reaction was stopped using 100 mM glycine and 2% BSA in 1×PBS. Exosomes-bound beads were washed in 1×PBS/2% BSA, blocked with 2% BSA, and stained for FACS with anti-glypican-1 (GPC1; PIPA528055, Thermo-Scientific). Secondary antibodies Alexa-488 or Alexa-594 (Life Technologies, NY, USA) were used.

Cancer Antigen CA19-9 Human ELISA. Serum cancer antigen CA 19-9 in patients with pancreatic cancer, pancreatic cancer precursor lesion, a benign pancreatic disease, and healthy donors were assessed using the Cancer Antigen CA19-9 Human ELISA Kit (Abcam, ab108642) according to the manufacturer's protocol.

DNA Extraction from Cells. Cells were grown in T225 cm² flasks for 2-3 days until they reached a confluence of 60%-70%. Next, cells were cultured in serum-free media for 48 h. The media was collected and centrifuged at 1000 rpm for 5 min, followed by a centrifugation step of 3000 rpm for 10 min to discard cellular detritus. Afterwards, the media was filtered using a 0.22 µm pore filter (Thermo Fisher Scientific, Waltham, Mass., USA). A total of 225 mL of conditioned media was collected and ultracentrifuged at 4° C. for 2 h. The supernatant was discarded and an additional 225 mL of conditioned, filtered media was ultracentrifuged at 4° C. for 2 h. The exosomes pellets of each ultracentrifugation step were pooled and incubated with 10 µL DNase I (1 U/µL, Cat. No. M6101, Promega, USA) at 37° C. for 30 min. Subsequently, 50 µL of DNase Stop Solution (Cat. No. M199A, Promega, USA) were added and the samples were heated at 65° C. in a water bath for 5 min. Next, the pooled exosomes pellet was washed in PBS and a second step of ultracentrifugation was performed at 150,000×g at 4° C. for 2 h. After aspiration of the supernatant, the pellet was suspended in 200 µL PBS. Five microliters of this sample were obtained and diluted at 1:100 and stored at −20° C. for further analysis using a NanoSight® LM10. The DNA of the remaining exosomes pellet was extracted using a commercial DNA extraction kit (DNeasy® Blood & Tissue Kit, Cat. No. 69506, Qiagen, Germany) according to the manufacturer's instructions. Finally, the DNA was eluted in 50 µL AE buffer and stored at −20° C. until processing. Double-stranded DNA was analyzed using an Agilent DNA 7500 Reagent Kit (Cat. No. 5067-1507, Agilent Technologies, USA).

DNA Extraction from Human Serum Samples. After serum samples were thawed, 500 µL of serum (5 mL of serum in case of Bioanalyzer analysis) were diluted in 11 mL 1×PBS, filtered through a 0.22 µm pore syringe filter (Cat. No. 6786-1302, GE Healthcare, GB) and ultracentrifuged at 150,000×g at 4° C. overnight. Afterwards, the exosome-depleted serum was collected and stored at −80° C. until further processing, whereas the exosomes pellet was incubated with 1 µL DNase I (1 U/µL, Cat. No. M6101, Promega, USA) at 37° C. for 30 min. Subsequently, 5 µL of DNase Stop Solution (Cat. No. M199A, Promega, USA) were added and the samples were heated at 65° C. in a water bath for 5 min. Next, the exosomes pellet was washed in 11 mL 1×PBS and a second step of ultracentrifugation was performed at 150,000×g at 4° C. for 2 h. After aspiration of the supernatant, the pellet was suspended in 200 µL PBS. Five microliters of this sample were diluted 1:100 and stored at −20° C. for further analysis using a NanoSight® LM10. The DNA of the remaining exosomes pellet was extracted using a commercial DNA extraction kit (DNeasy® Blood & Tissue Kit, Cat. No. 69506, Qiagen, Germany) according to the manufacturer's instructions. Finally, the DNA was eluted in 50 µL AE buffer and stored at −20° C. until processing.

DNA Extraction from Human Primary Pancreatic Cancer. Immediately after resection, pancreatic tumor samples were snap-frozen in liquid nitrogen and stored at −80° C. until further processing. A 10 µm reference section of each sample was cut and stained with hematoxylin and eosin by standard methods to evaluate the proportion of tumor tissue and adjacent tumor stroma. Samples with a tumor stroma proportion >30% were included into this study. DNA isolation was performed using a commercial DNA extraction kit (DNeasy® Blood & Tissue Kit, Cat. No. 69506, Qiagen, Germany) according to the manufacturer's protocol. The amount of DNA from tumor samples was quantified using a Nanodrop® 1000 spectrophotometer (Thermo Fisher Scientific, Wilmington, Del., USA).

RNA Extraction from Cells and Exosomes. RNA of cells and exosomes was isolated using a TRIzol® Plus RNA purification kit (Life Technologies, Cat. No. 12183555) according to manufacture's protocol. RNA was quantified using a Nanodrop® ND-1000 (Thermo Fischer Scientific).

Western Blot Analysis and Antibodies. To monitor exosomal expression of TSG 101 and other proteins, exosomes were harvested in 8 M Urea/2.5% SDS buffer containing 5 µg/mL leupeptin, 1 µg/mL pepstatin, and 1 mM PMSF, and cells were lysed in RIPA buffer containing 5 µg/mL leupeptin, 1 µg/mL pepstatin, and 1 mM PMSF. Samples were loaded according to Bradford quantification and analyzed using acrylamide gels. Wet electrophoretic transfer was used to transfer the proteins in the gel onto PVDF membranes (Immobilon-P). The protein blot was blocked for 1 h at room temperature with 5% non-fat dry milk in 1×PBS and 0.05% Tween® 20 and incubated overnight at 4° C. with the following primary antibodies: 1:300 anti-TSG101 (anti-ab83; Abcam), 1:300 anti-GPC1 (PIPA528055; Thermo-Scientific); 1:300 anti-β-Actin (A3854; Sigma-Aldrich); 1:300 anti-CD81 (sc-166029; Santa-Cruz); 1:300 anti-Flot-tilin1 (sc-25506; Santa-Cruz). Secondary antibodies were incubated for 1 h at room temperature. Washes after antibody incubations were performed on an orbital shaker, four times at 10 min intervals, with 1×PBS and 0.05% Tween® 20. Blots were developed with chemiluminescent reagents from Pierce.

Polymerase Chain Reaction (PCR). The amount of DNA from cells and cell media-derived exosomes was quantified using a Nanodrop® 1000 spectrophotometer (Thermo Fisher Scientific, Wilmington, Del., USA). The amount of DNA from human serum-derived exosomes was quantified using PicoGreen® (Quant-iT™ PicoGreen® dsDNA Assay Kit, Cat. No. P11496, Life Technologies, USA). PCR was performed in a 25 µL reaction tube containing 10 µL template DNA, 1 µM of each primer, 2.5 mM of each dNTP, 2.5 10×PCR buffer, 25 mM Mg solution, 0.5 µL H$_2$O, and 2.5 µL Taq polymerase. Amplification was carried out in a T100 ThermoCycler (Bio-Rad) under the following conditions: 94° C. for 1 min, 2 cycles of 94° C. for 10 s, 67° C. for 30 s, 70° C. for 30 s; 2 cycles of 94° C. for 10 s, 64° C. for 30 s, 70° C. for 30 s; 2 cycles of 94° C. for 10 s, 61° C. for 30 s, 70° C. for 30 s; 35 cycles of 94° C. for 10 s, 59° C. for 30 s, 70° C. for 30 s; and a final hold at 4° C. KRAS analysis was performed using the following primers: forward 5'-AAGGCCTGCTGAAAATGACTG-3' (SEQ ID NO: 1), reverse 5'-TCACAATACCAAGAAACCCAT-3' (SEQ ID NO: 2). P53 analysis was performed using the following primers: p53 Exon 7-8p (609 bp): forward 5'-TCCTAGGTTGGCTCTGAC-3' (SEQ ID NO: 3), reverse 5'-CCTGCTTGCTTACCTCGCT-3' (SEQ ID NO: 4); p53 Exon 5-8 (1564 bp): forward 5'-TTCCTCTTCCTACAGTACTCC-3' (SEQ ID NO: 5), reverse 5'-CCTGCTTGCT-TACCTCGCT-3' (SEQ ID NO: 6). PCR products were purified using the QIAquick® PCR purification kit (Qiagen, Hilden, Germany). Subsequently, sequencing reactions were performed using BigDye® terminator kit (v3.1, Life Technologies, USA) according to the manufacturer's instructions. For sequencing, the following primers were used: KRAS forward 5'-AAGGCCTGCTGAAAATGACTG-3' (SEQ ID NO: 7) and reverse 5'-AGAATGGTCCTGCAC-CAGTAA-3' (SEQ ID NO: 8); p53 Exon 5-8 forward 5'-TCTTCCTACAGTACTCCCCT-3' (SEQ ID NO: 9) and reverse 5'-GCTTGCTTACCTCGCTTAGT-3' (SEQ ID NO: 10); p53 Exon 7-8 forward 5'-TAGGTTGGCTCTGACTGT-3' (SEQ ID NO: 11) and reverse 5'-GCTTGCTTAC-CTCGCTTAGT-3' (SEQ ID NO: 12). Sequencing products were separated on an ABI 3730 automated sequencer (Life Technologies, USA). KRAS mutation status was evaluated using Finch TV (Geospiza, Inc., Seattle, Wash., USA).

Quantitative Real-Time PCR (qRT-PCR). qRT-PCR was performed with DNase-treated RNA using the SuperScript® III Platinum® One-Step Quantitative RT-PCR System (Cat. No. 11732-088, Invitrogen, Life Technologies, Grand island, NY, USA) according to the manufacturer's recommendation on an 7300 Sequence Detector System (Applied Biosystems). Primers for KRAS G12D mRNA and KRAS G12V mRNA (both Sigma-Aldrich Corp., St. Louis, Mo., USA) were designed as reported previously (Rachagani et al., 2011). Briefly, the altered base of KRAS G12D and KRASG12V mutation was kept at the 3' end of the forward primer. An additional base mutation was included two positions before the KRAS mutation in order to increase the specificity of the amplification of the mutant KRAS allele. Forward primer sequences for KRAS G12D mRNA: F-5'-ACTTGTGGTAGTTGGAGCAGA-3' (SEQ ID NO: 13). Forward primer sequences for KRAS G12V mRNA: F-5'-ACTTGTGGTAGTTGGAGCAGT-3' (SEQ ID NO: 14). Forward primer sequences for KRAS wild-type mRNA: F-5'-ACTTGTGGTAGTTGGAGCTGG-3' (SEQ ID NO: 15). Reverse primer for all KRAS: R-5'-TTGGATCATAT-TCGTCCACAA-3' (SEQ ID NO: 16). GPC1 mRNA primer pairs (Cat. No. PPH06045A) and 18s mRNA primer pairs (Cat. No. QF00530467) were purchased from Qiagen (Hilden, Germany). The threshold cycle (Rothstein et al., 2001) (Ct) (i.e., the fractional cycle number at which the amount of amplified target reached a fixed threshold) was determined and expression was measured using the $2^{-\Delta Ct}$ formula, as previously reported (Livak and Schmittgen, 2001).

Electron Microscopy. Samples were placed on 400 mesh formvar-coated copper grids treated with poly-L-lysine for 1 h. Excess samples were blotted with filter paper, then negatively stained with Millipore-filtered aqueous 1% uranyl acetate for 1 min. Stain was blotted dry from the grids with filter paper and samples were allowed to dry. Samples were then examined in a JEM 1010 transmission electron microscope (JEOL, USA, Inc., Peabody, MA) at an accelerating voltage of 80 Kv. Digital images were obtained using the AMT Imaging System (Advanced Microscopy Techniques Corp., Danvers, Mass.).

Immunogold Labeling. Fixed specimens at an optimal concentration were placed onto a 400 mesh carbon/formvar-coated grid and allowed to absorb to the formvar for a minimum of 1 min. For immunogold staining, the grids were placed into a blocking buffer for a block/permeablization step for 1 h. Without rinsing, the grids were immediately placed into the primary antibody at the appropriate dilution overnight at 4° C. (1:300 anti-CD9 (ab92726, Abcam) and anti-GPC1 (PIPA528055, Thermo-Scientific)). As controls, some grids were not exposed to the primary antibody. The next day all of the grids were rinsed with PBS and then floated on drops of the appropriate secondary antibody attached with 10 nm gold particles (AURION, Hatfield, Pa.) for 2 h at room temperature. Grids were rinsed with PBS and were placed in 2.5% glutaraldehyde in 0.1 M phosphate buffer for 15 min. After rinsing in PBS and distilled water, the grids were allowed to dry and stained for contrast using uranyl acetate. The samples were viewed with a Tecnai™ BioTwin transmission electron microscope (FEI, Hillsboro, Oreg.) and images were taken with an AMT CCD Camera (Advanced Microscopy Techniques Corp.).

Sucrose Gradients. To further characterize exosomes, sucrose density gradients were performed. Briefly, exosomes were resuspended in 2 mL of HEPES/sucrose stock solution (2.5 M sucrose, 20 mM HEPES/NaOH solution, pH 7.4). The exosomes suspension was overlaid with a linear sucrose gradient (2.0-0.25 M sucrose, 20 mM HEPES/NaOH, pH 7.4) in a SW41 tube (Beckman). The gradients were ultracentrifuged for 16 h at 210,000×g at 4° C. Then, gradient fractions of 1 mL were collected from top to bottom. Densities were evaluated using a refractometer. Next, the exosomes pellets were washed in 1×PBS followed by a second step of ultracentrifugation at 150,000×g at 4° C. for 2 h. Exosomes pellets were resuspended in Laemmli buffer and/or PBS for further immunoblotting and FACS analysis.

Whole Genome Shotgun Sequencing. Whole genome sequencing was performed using the ThruPLEX®-FD library prep technology (Cat. No. R40048, Rubicon Genomics, Ann Arbor, Mich.) in combination with the Illumina® HiSeq2000 sequencing platform, paired-end 2×51 bp, to a coverage depth of 4× in exosomes and matched tumor samples. To assess copy number profile and gain additional insights into structural rearrangements, an algorithm called BIC-seq was utilized (Xi et al., 2011).

MRI Imaging. MRI studies were conducted using a 7 T small animal MR system. The BioSpec® USR 70/30 (Bruker Biospin MRI, Billerica, Mass.) is based on an actively-shielded 7 T magnet with a 30-cm bore and cryo-refrigeration. The system is equipped with 6 cm inner-diameter gradients that deliver a maximum gradient field of 950 mT/m. A 3.5 cm inner-diameter linear birdcage coil transmits and receives the MR signal. For image acquisition, T2 weighted, respiratory gated, multi-slice imaging was performed with respiration held to under 25 breaths/min to minimize motion artifacts in the abdomen. For mice where fat signal masked the T2 weighted image, the fat-suppression pulse module was utilized. Acquisition parameters were minimally modified from Schmid et al. (2013). The RARE-T2 weighted pulse sequence was modified to include an effective Te of 56 ms with a total TR of 2265 ms. Between 18 and 20 coronal slices were acquired per mouse with a slice thickness of 0.75 mm and slice spacing of 1 mm. In plane, pixel sizes of 0.156 mm×0.156 mm with a matrix size of 256×192 (40 mm×30 mm FOV) was chosen to minimize in plane partial volume effects, maintain a FOV sufficient to cover the abdomen, while also providing sufficient throughput for the experiment. To measure tumor burden, the region of suspected lesions were drawn blinded on each slice after image intensities were normalized. The volume was calculated by addition of delineated regions of interest in $mm^2 \times 1$ mm slice distance.

Statistical Analysis. The GraphPad Prism version 6.0 (GraphPad Software, La Jolla, Calif., USA) and MedCalc statistical software version 13.0 (MedCalc Software bvba, Acacialaan 22, Ostend, Belgium) were used for all calculations. Student's t-tests were applied to calculate expression differences of the qPCR results. Analysis of variance (ANOVA) tests were performed to calculate differences of multiple serum factors in murine and human serum samples. Tuckey-Kramer tests were applied for pairwise comparisons of subgroups when the ANOVA test was positive. A paired two-tailed Student's t-test was applied to calculate differences of $GPC1^+$ population and CA 19-9 in the longitudinal cohort between preoperative blood samples and postoperative specimens. Receiver operating characteristic (ROC) curves were used to determine and compare the sensitivity, specificity, positive and negative predictive value, and area under the curves (AUC) of serum factors using the Delong method (DeLong et al., 1988). The cut-off value was determined using the Youden-Index. Univariate analysis by the log-rank test was conducted to visualize (Kaplan-Meier curves) and to assess disease-specific survival (time from diagnosis to cancer-related death or last follow-up) in the longitudinal cohort of patients with pancreatic cancer. A multivariate analysis using the Cox proportional hazards regression model was performed to evaluate the effect of a decrease of $GPC1^+$ population in addition to age (continuous variable), AJCC tumor stage, and tumor grade (G) and CA 19-9 (U/mL). Correlation analysis between murine tumor burden and $GPC1^+$ exosomes was performed using the Spearman correlation test. Figures were prepared by using GraphPad Prism (GraphPad Software, La Jolla, Calif., USA) and MedCalc statistical software version 13.0 (MedCalc Software bvba, Acacialaan 22, Ostend, Belgium). All presented P values are two-sided and a P value<0.05 was considered to be statistically significant.

EXAMPLE 1

Exosomes Contain >10 kb Fragments of Double-Stranded Genomic DNA

Figure 1B:
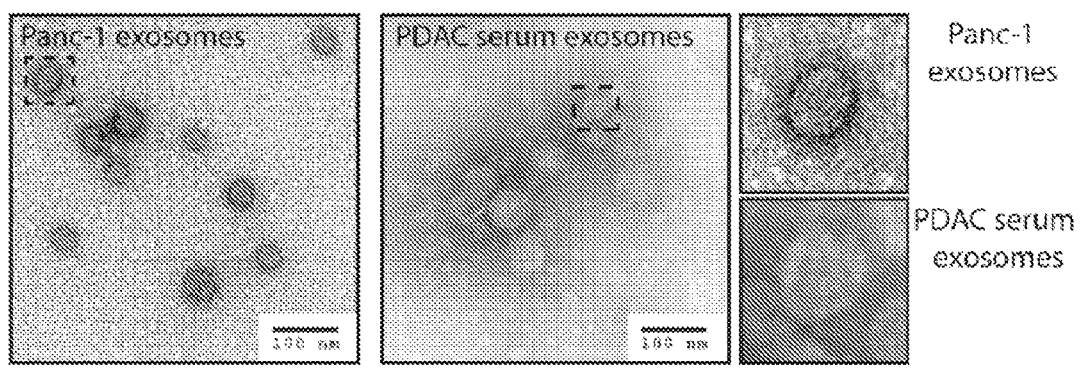
Figure 1C:
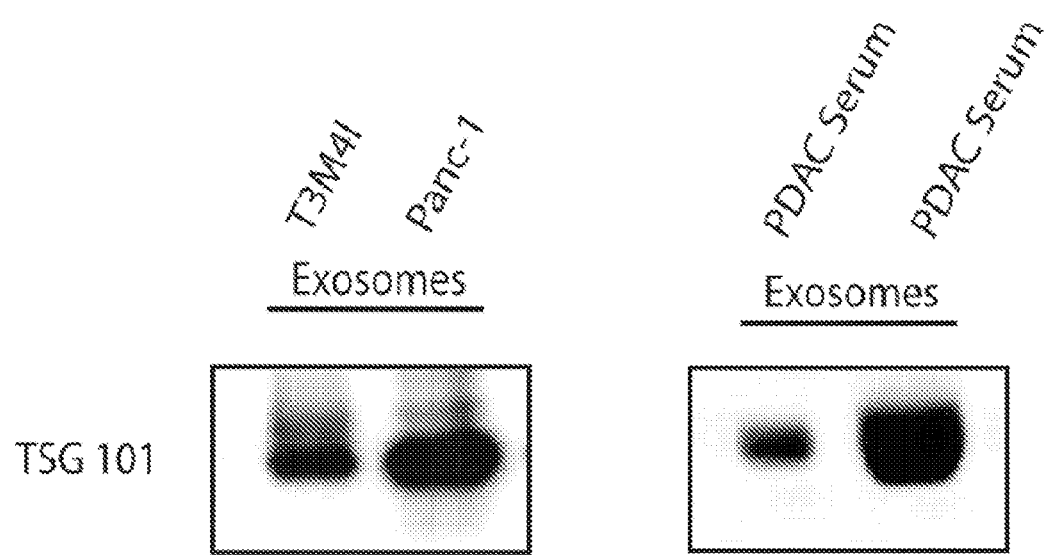
Figure 1D:
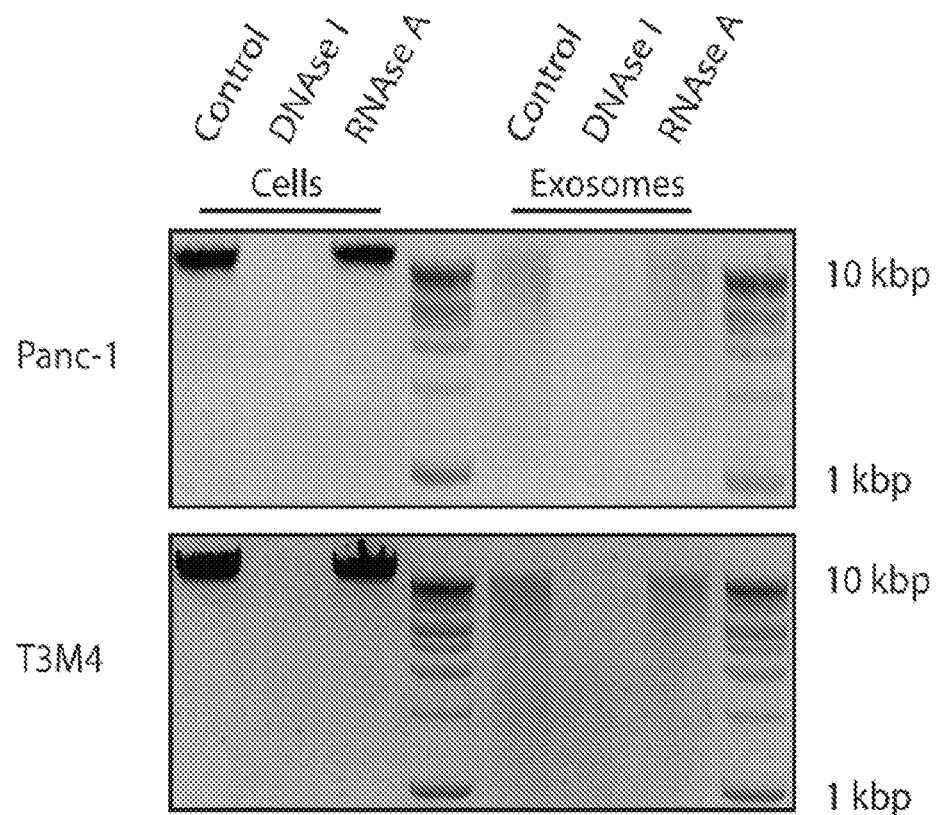
Figure 1E:
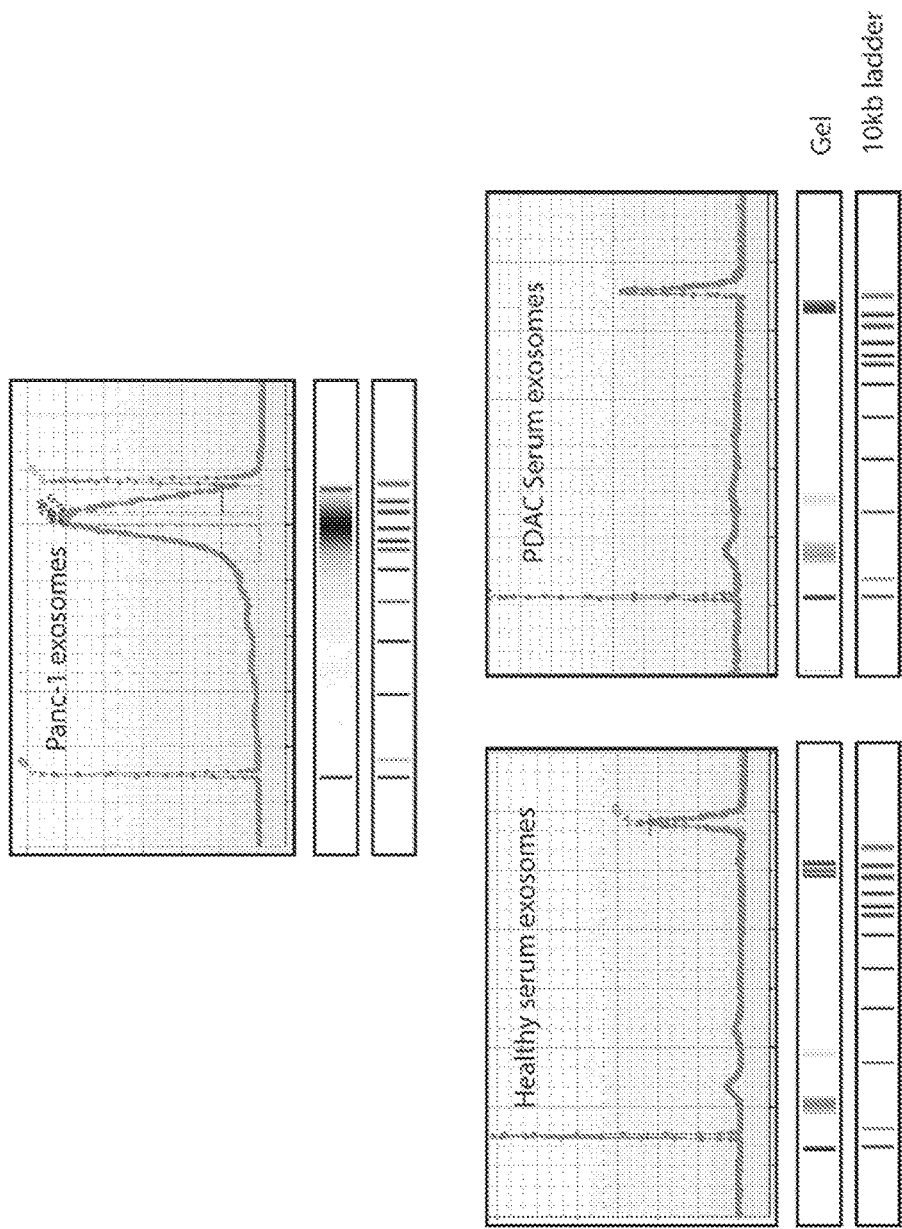
Figure 1F:
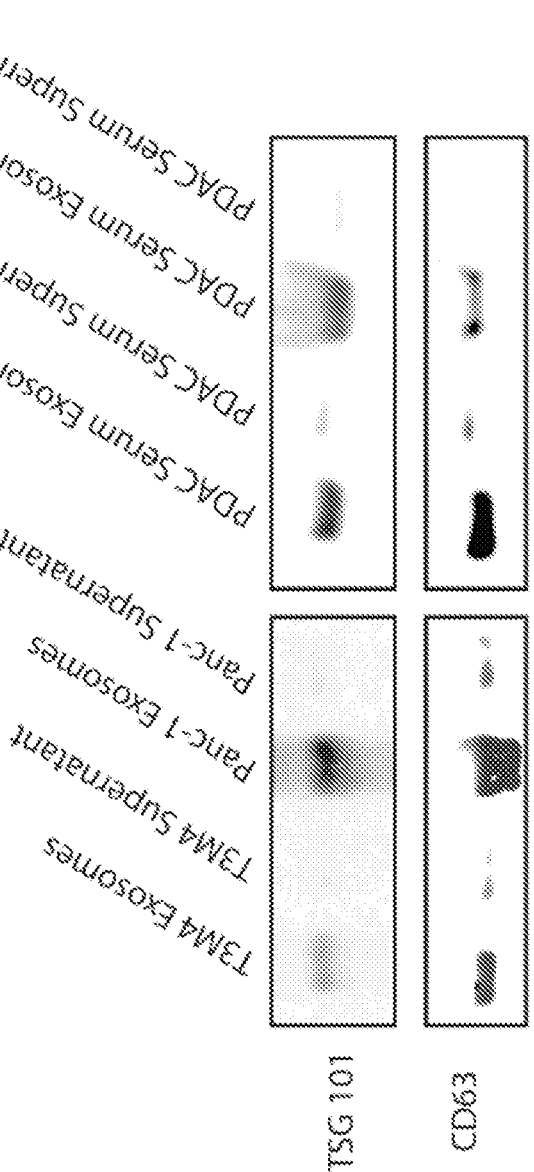

Cellular exosomes were isolated from two human pancreatic cancer cell lines (Panc-1 and T3M4) and serum of patients with pancreatic cancer (Luga et al., 2012; Thery et al., 2006). To reduce external DNA contamination, exosomes were treated extensively with DNase I prior to DNA extraction, as described previously (Balaj et al., 2011). The presence of exosomes and their concentration from both cancer cell lines and serum samples was confirmed using a NanoSight® LM10 (FIG. 1A). Moreover, exosomes were identified as a homogenous population by electron microscopy (FIG. 1B) and by the expression of the exosomes markers, TSG 101 and CD63 (FIGS. 1C and F). Additionally, after extraction of exosomal DNA from cancer cell lines, the eluate was subjected to RNase A to exclude RNA. Subsequently, the pre-treated eluate was analyzed on a 2% agarose gel (FIG. 1D). This revealed the presence of long fragments of DNA in exosomes without RNA. By using a double-stranded DNA detection kit, it was shown that exosomes from pancreatic cancer cells and from serum samples contain genomic double-stranded DNA (FIG. 1E).

EXAMPLE 2

Exosomes Contain Mutated KRAS and p53 DNA

Figure 2E:
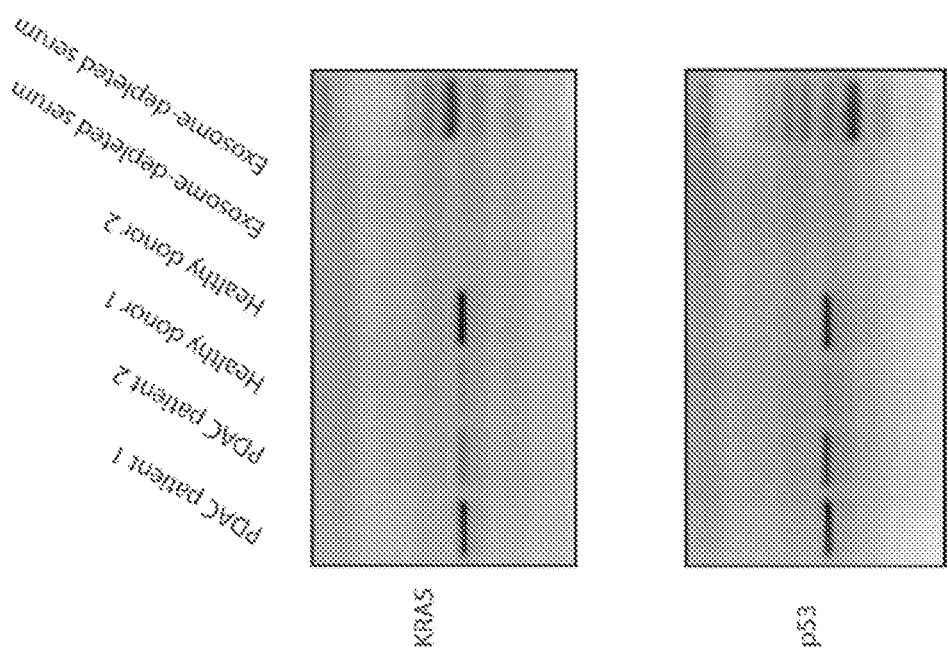

KRAS and p53 are the most frequently mutated genes in pancreatic ductal adenocarcinoma (Biankin et al., 2012). A 466 bp fragment of KRAS encoding exon 2 and a portion of intron 2 and a 1564 bp fragment of p53 spanning from exon 5 to exon 8, including introns 5, 6, and 7 were amplified from both cell lines and DNA isolated from exosomes derived from the cell lines (FIG. 2A). KRAS and p53 mutations in Panc-1 and T3M4 have been described previously (Moore et al., 2001). Panc-1 displays a heterozygous KRAS mutation in codon 12 (glycine to aspartate) and a homozygous p53 mutation in codon 273 (arginine to histidine) (Moore et al., 2001). T3M4 cells contain wild-type KRAS but display a homozygous p53 mutation in codon 220 (tyrosine to cysteine) (Moore et al., 2001). By Sanger sequencing of the PCR amplified DNA, the identical KRAS and p53 mutations were detected in the DNA isolated from exosomes derived from Panc-1 cells and the identical p53 mutation were detected in the DNA isolated from exosomes derived from T3M4 cells (FIG. 2B). Mutation in the KRAS DNA was not detected in T3M4 cells or the exosomes isolated therefrom.

Based on the observations using cell lines, it was hypothesized that circulating serum exosomes from patients with pancreatic cancer might also contain KRAS and p53 DNA. A 466 bp fragment of KRAS encoding exon 2 and a portion of intron 2 was amplified. Subsequently, a 609 bp DNA fragment of p53 overlapping exons 7 and 8 and intron 7 was isolated in all human samples (FIGS. 2C and E). PCR for KRAS and p53 was also performed using serum samples depleted of exosomes to evaluate the presence of DNA therein. However, no KRAS or p53 PCR products were amplified in the exosomes-depleted serum (FIGS. 2C and E). The PCR amplicons from the DNA isolated from exosomes were subjected to Sanger sequencing. Sanger sequencing detected DNA with a KRAS mutation in serum samples of patients with pancreatic cancer (FIG. 2D). One KRAS mutation was located in codon 12 and was characterized by a base change of GGT to TGT. The second KRAS mutation was found in codon 22 with a base change from CAG to CTG. Additionally, in one patient with pancreatic cancer, a p53 mutation was detected in codon 273 with a base change from CGT to CAT (FIG. 2D).

EXAMPLE 3

Figure 3A:
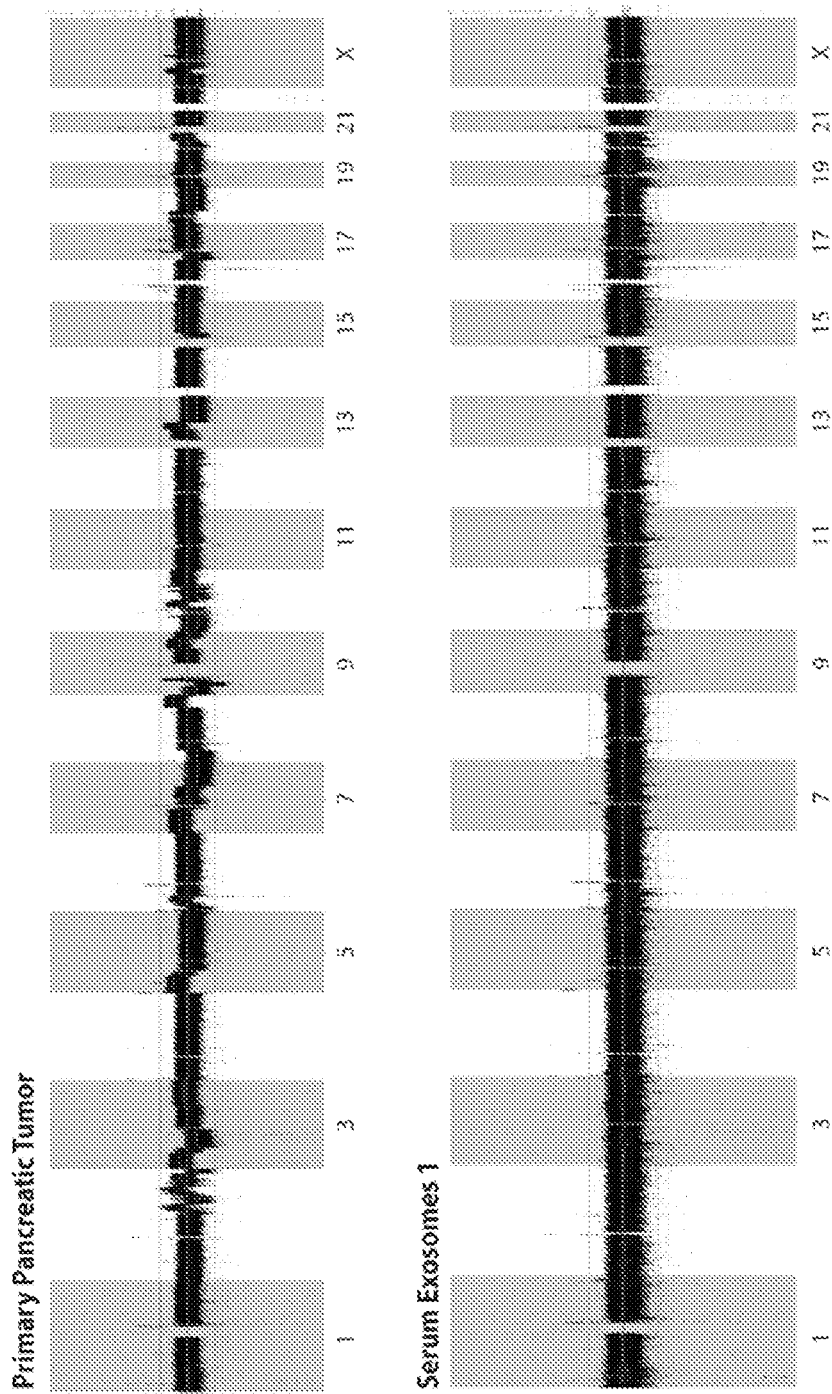
FIGS. 3A-B. Serum-derived exosomes contain genomic DNA spanning all chromosomes. Whole genome sequencing was conducted on serum-derived, exosomal DNA and corresponding primary tumor from two patients. BIC-seq control-free $log_2$ copy-number profile across all human chromosomes, bin size 1000 bp; RAW profile—black, segmented—center, gray line. Profiles demonstrate somatic chromosomal gains (up) and losses (down), as well as normal polymorphism. In the second case (FIG. 3B), a lack of structural chromosomal rearrangement expected for PDAC is explained due to possible low number of cancer cells in the sample. Sequencing revealed that circulating exosomes contain genomic DNA spanning all chromosomes.
Figure 3B:
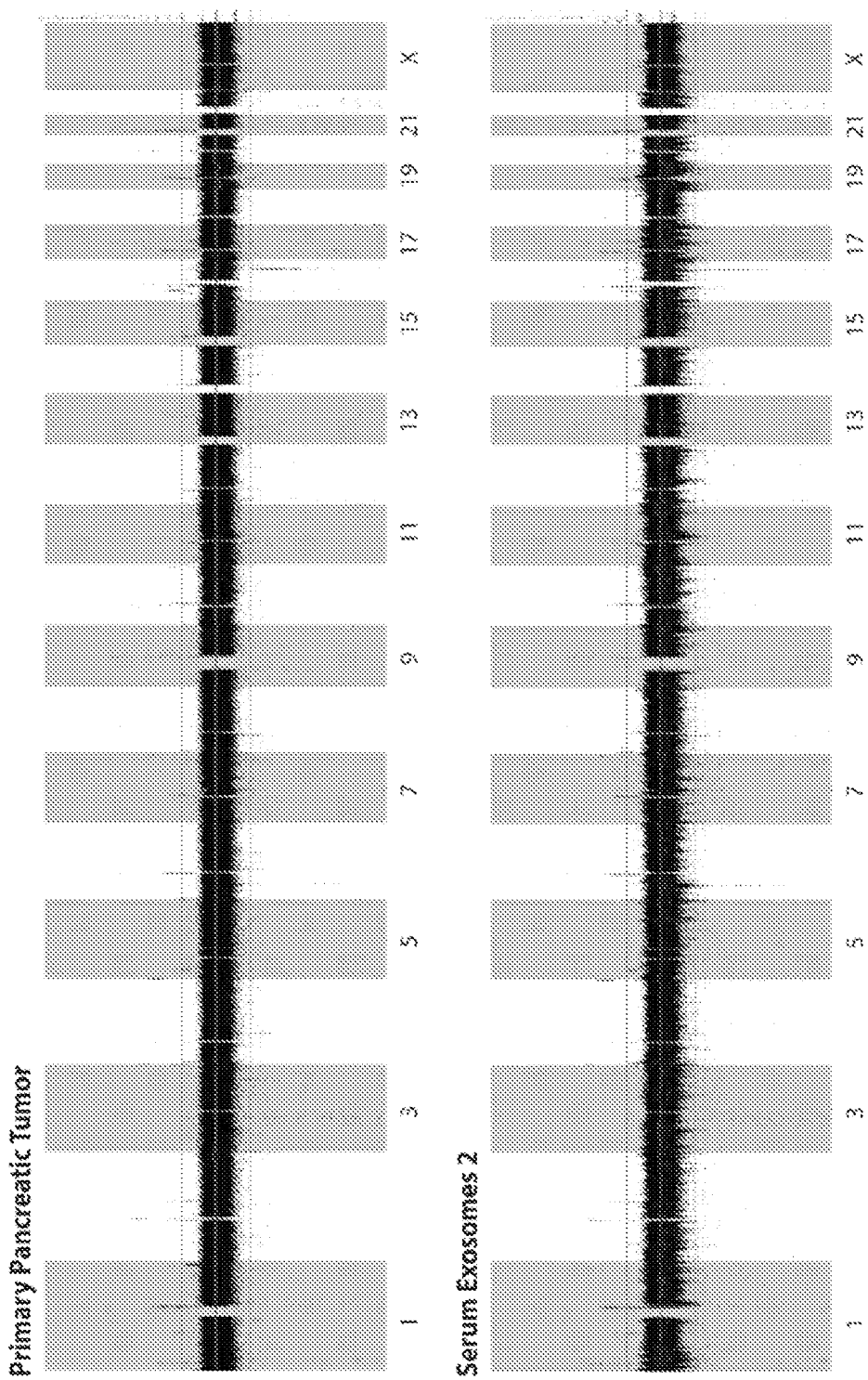

Circulating Exosomes from the Peripheral Blood of PDAC Patients Contain Double-Stranded Genomic DNA Spanning all Chromosomes Two pancreatic cancer samples were investigated using paired serum exosomal DNA and matched tumor sample. A 4× whole genome sequence coverage was achieved with an inferred library insert size of ~160 bp. The percent of reads mapped to the human genome was around 96%. The properly paired percentage read ~92% between tumor genomic DNA and exosomal genomic DNA. Sequence complexity as a number of unique reads was over $9\times10^8$ in all samples. A bulk of serum-derived exosomes contain DNA spanning uniformly all chromosomes resembling nuclear genomic DNA (FIGS. 3A and 3B).

EXAMPLE 4

Mammalian Exosomes Produce Proteins

After the initial discovery of exosomes as byproducts of reticulocyte differentiation (Raposo and Stoorvogel, 2013; Harding et al., 1984), exosomes were widely considered as mostly inert forms of cellular elimination of obsolete proteins. However, it soon became clear that exosomes are secreted by almost all mammalian cells and could indeed be found in most body fluids (El-Andaloussi et al., 2013). Exosomes are now known to have multiple functions in cell-cell communication, being involved in processes as diverse as antigen presentation (Raposo et al., 1996; Zeelenberg et al., 2008), spread of pathogens, such as HIV and malaria (Wiley and Gummuluru, 2006; Regev-Rudzki et al., 2013), the onset of fibrosis (Borges et al., 2013), and perhaps most notably, cancer progression and metastasis (Kahlert and Kalluri, 2013; Skog et al., 2008; Luga et al., 2013; Peinado et al., 2012). Due to their involvement in such a wide array of pathologies, a deeper understanding of exosomes biology and content became imperative. As a result, and particularly in the context of cancer, several studies have demonstrated that exosomes nucleic acid or protein profiles can correlate with disease progression (Skog et al., 2008; Silva et al., 2012; Taylor and Gercel-Taylor 2008; Ji et al., 2013). One such recent profile involving proteomic clustering of exosomes from colorectal cancer cells identified several constituents of protein biogenesis (Choi et al., 2012). This confirms a previous mass spectroscopy study that identified constituents of the protein translation machinery in exosomes, such as eukaryotic initiation factors, ADP ribosylation factors, and ribosomal proteins (Valadi et al., 2007; Pisitkun et al., 2004). Allied to the observation that mRNAs and their corresponding proteins can be found packaged inside the same exosomes, this raised the tantalizing possibility that exosomes could have the capability to translate nucleic acids into proteins, independently from their donor cells.

Figure 4A:
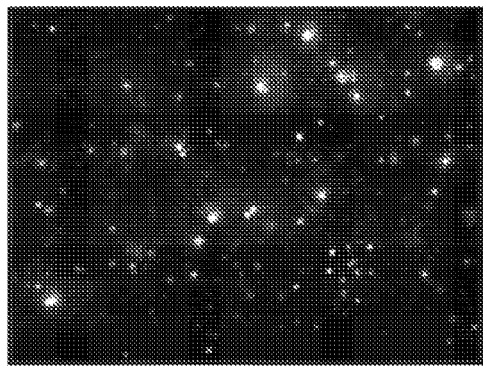
FIGS. 4A-E.
Figure 4A:
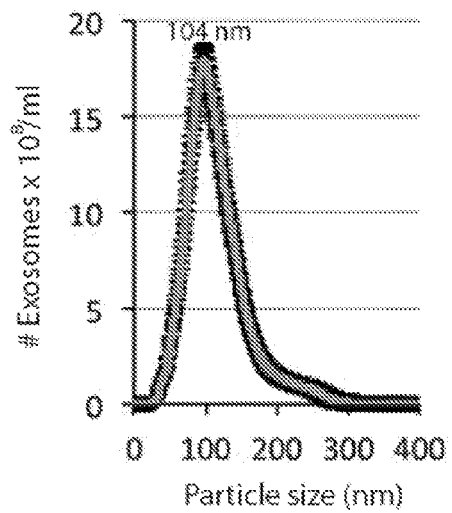
Figure 4B:
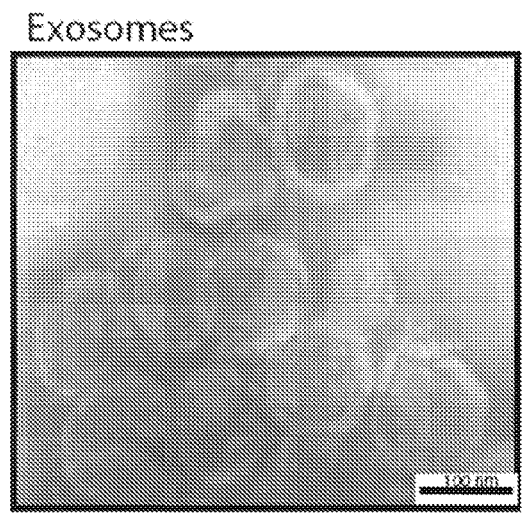
Figure 4C:
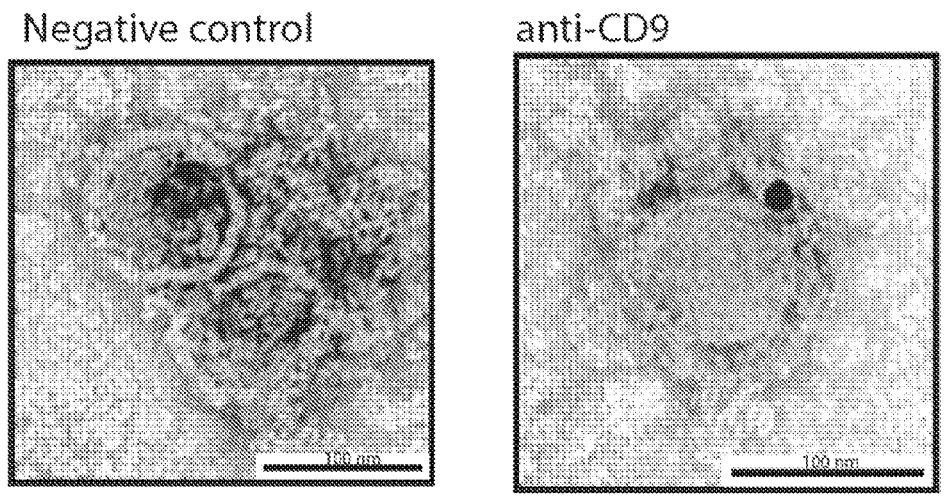
Figure 4D:
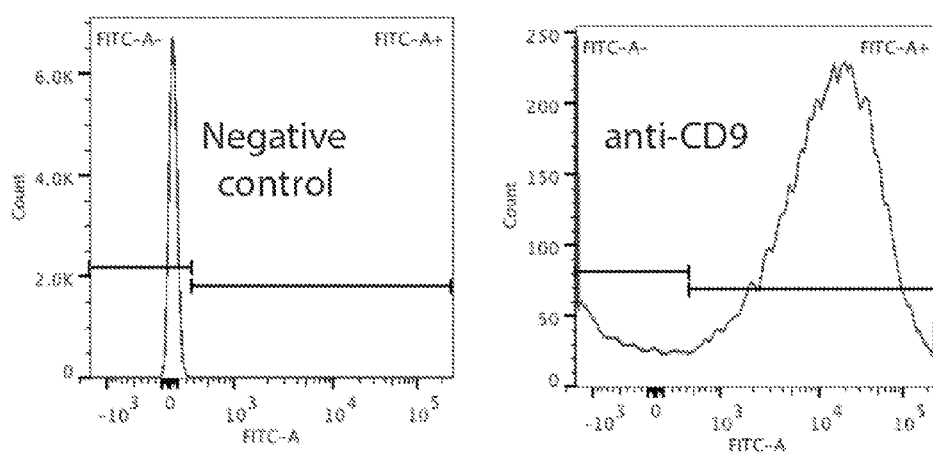
Figure 4E:
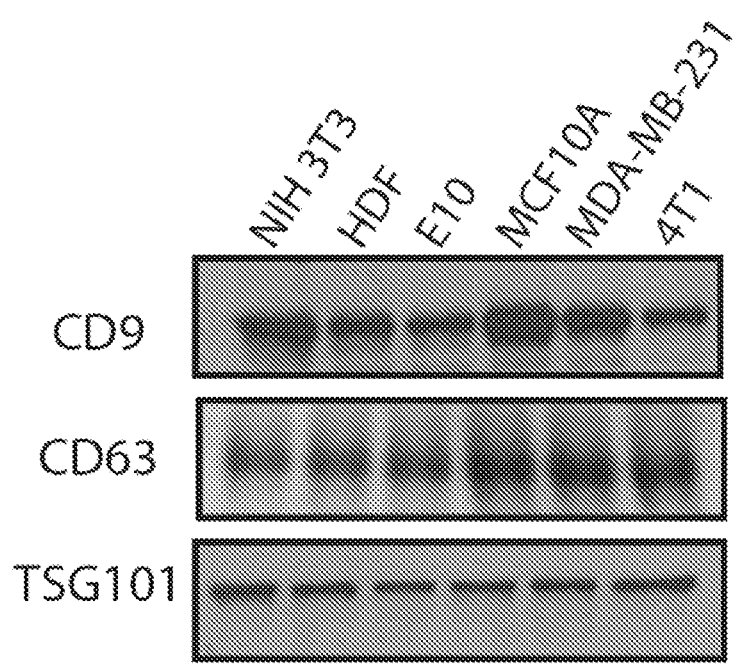

Exosomes were isolated from different murine and human cell lines (normal and immortalized fibroblasts, HDF and NIH 3T3; lung epithelial cells, E10; non-tumorigenic human epithelial breast, MCF10A; triple negative human metastatic breast carcinoma, MDA-MB-231; and mouse metastatic mammary carcinoma, 4T1) using established ultracentrifugation techniques (Borges et al., 2013; Thery et al., 2006). NanoSight® (Soo et al., 2012) nanoparticle tracking analysis revealed particles with a size distribution peaking at 104±1.5 nm in diameter (FIG. 4A). The exosomes extracts were further analyzed by transmission electron microscopy (TEM), which revealed structures with a lipid bilayer and size between 50-150 nm (FIG. 4B). In addition immunogold labeling using CD9 antibody revealed expression of the tetraspanin at the exosomes surface (FIG. 4C). To confirm exosomes identity, flow cytometry analysis showing expression of exosomes tetraspanin surface marker CD9 was also performed (FIG. 4D). Expression of the CD9, CD63, and TSG101 markers was also confirmed by immunoblot analysis of exosomes protein extracts (FIG. 4E).

Figure 5A:
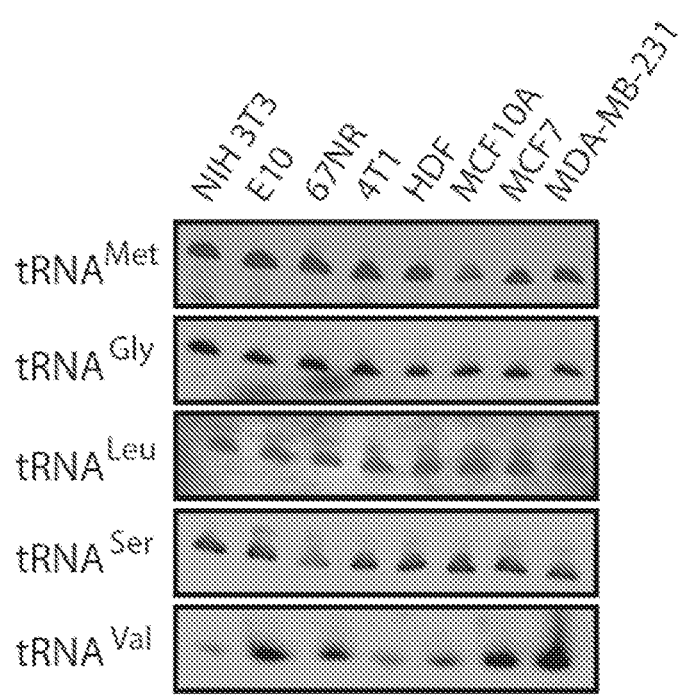
FIGS. 5A-E.
Figure 5B:
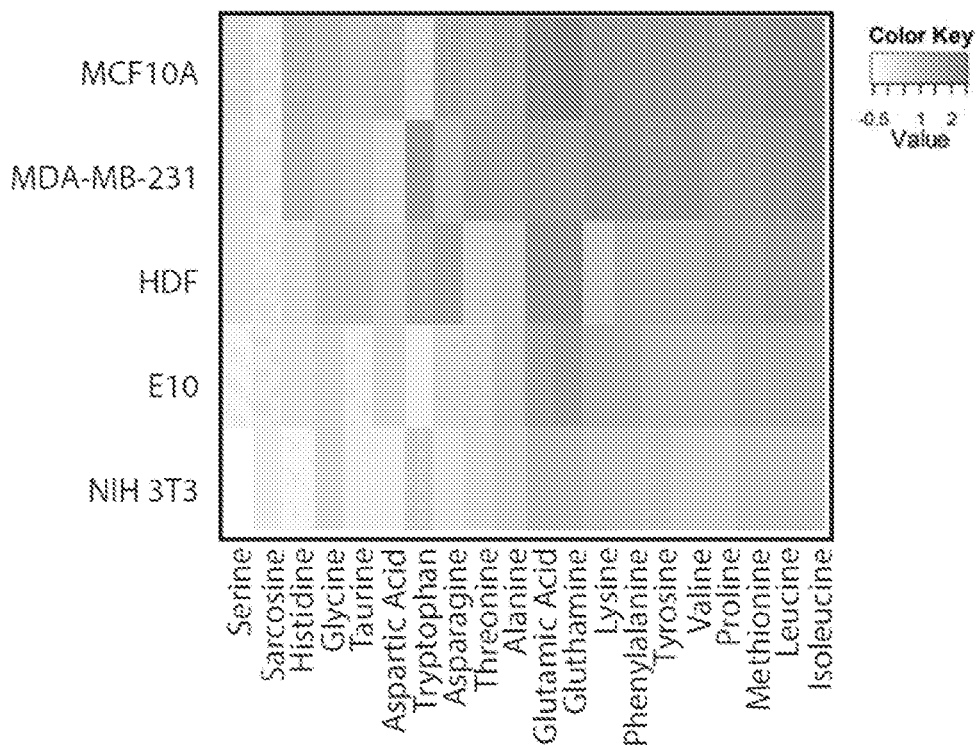
Figure 5C:
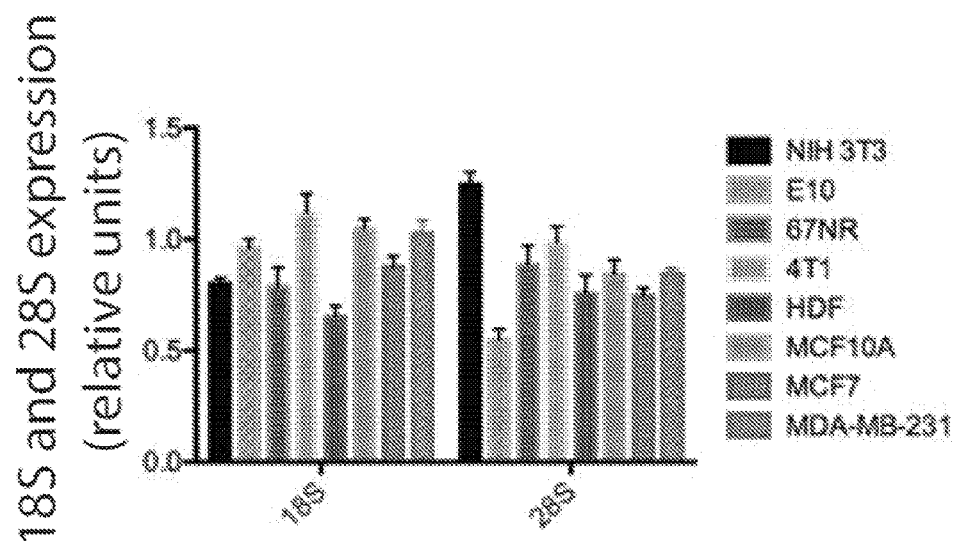
Figure 5D:
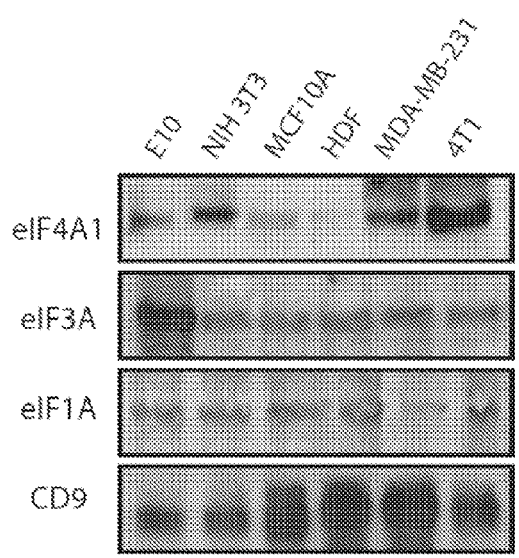
Figure 5E:
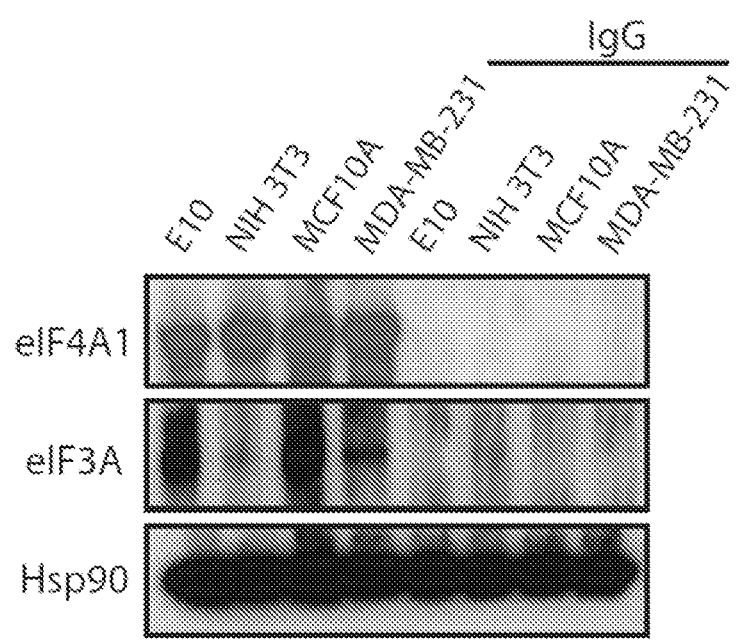

Having confirmed the identity and purity of harvested exosomes from the selected cell lines, the presence of components of the protein translation machinery within exosomes was determined. Exosomes are enriched not only in mRNAs but also in small non-coding RNAs, including miRNAs and tRNA fragments (Nolte-'t Hoen et al., 2012). Through Northern Blot analysis, the presence of tRNAs for methionine, serine, glycine, valine, and leucine were identified in RNA extracts from exosomes harvested from a series of cell lines (FIG. 5A). Additionally, high-performance liquid chromatography (HPLC) analysis of protein extracts from exosomes showed they contain free amino acids (FIG. 5B). Previously, it had been shown that exosomes contain ribosomal RNA using high-throughput sequencing (RNA-Seq) techniques. The presence of ribosomal RNAs was confirmed using quantitative PCR analysis of exosomal RNA extracts, which showed the presence of rRNA fragments 18s and 28s in all exosomes (FIG. 5C). Together with previously published proteomic data that identified the presence of ribosomal proteins in exosomes, this suggested the existence of functional ribosomal subunits within exosomes. In order for translation to take place, eukaryotic initiation factors (eIF) needs to form a complex with the 40s ribosomal subunit and methionine-coupled tRNA in order to recognize the mRNA and initiate translation. An eIF4 complex containing eIF4A, eIF4E, and eIF4G is of particular importance as it recognizes the 5' cap structure existing in eukaryotic mRNAs. Previous mass spectrometry studies have identified the presence of different eIFs in exosomes (Valadi et al., 2007; Pisitkun et al., 2004). The expression of eIF4A1, eIF3A, and eIF1A in exosomes was confirmed using immunoblot analysis (FIG. 5D). Furthermore, initiation factors eIF4A and eIF3A were co-immunoprecipitated, suggesting the presence of an initiation complex within the exosomes (FIG. 5E). Taken together, these data provide the intriguing possibility that active protein translation could be taking place within exosomes.

Figure 6A:
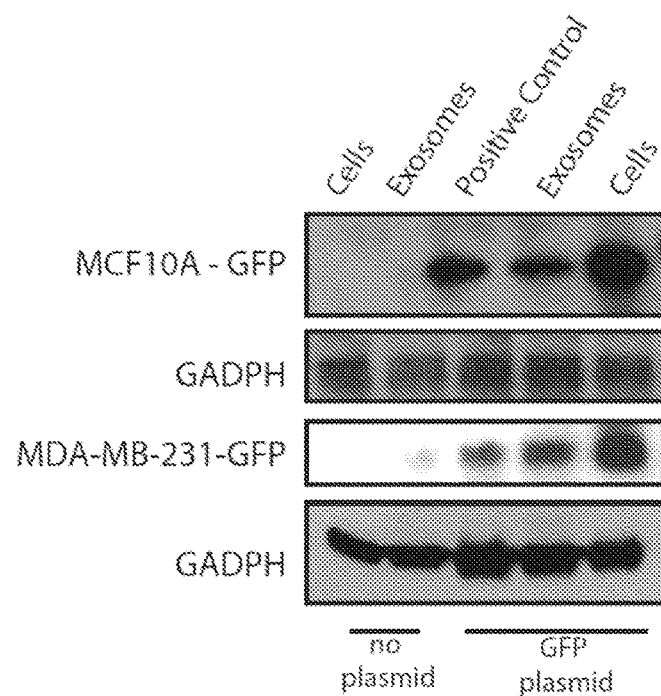
FIGS. 6A-C.
Figure 6B:
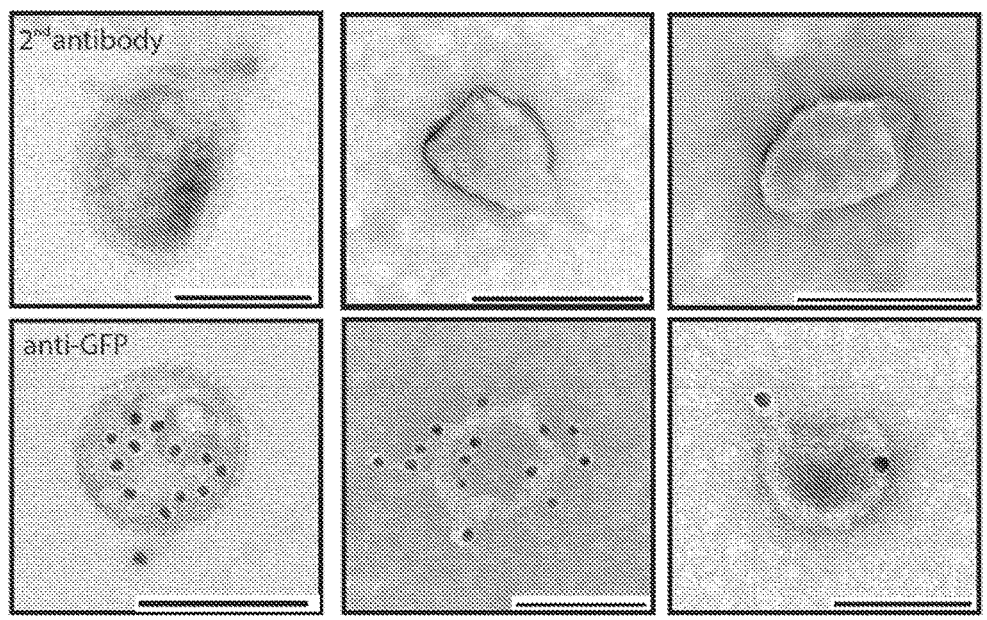
Figure 6C:
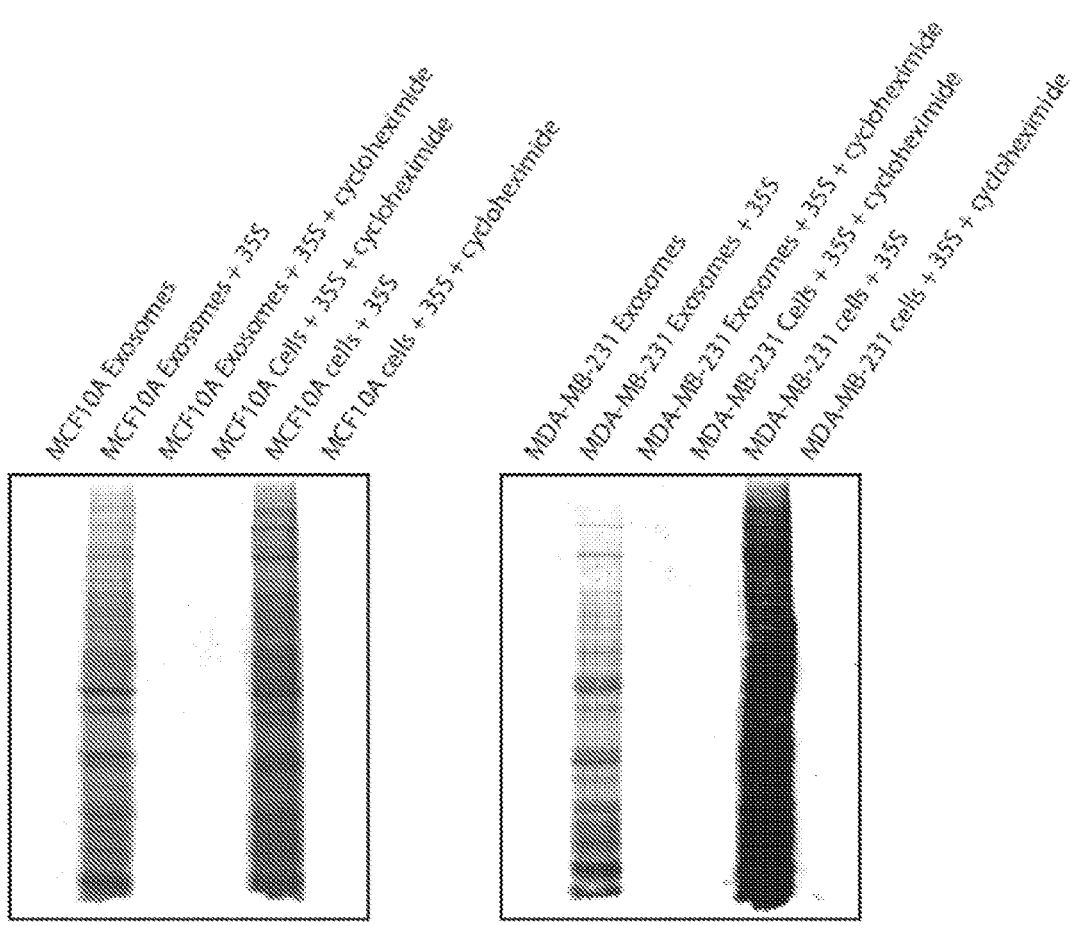

To determine the translational capability of exosomes, protein extracts of MCF10A and MDA-MB-231-derived exosomes were incubated with mRNA encoding green fluorescent protein (GFP), which is not expressed in mammalian cells, in an in vitro translation assay. Western blot analysis of the protein extracts showed expression of GFP after incubation with its mRNA, confirming protein formation (FIG. 6A). The same translational competency was investigated in intact exosomes by electroporating them with a plasmid coding for GFP, using previously published techniques (El-Andaloussi et al., 2012). Electroporated exosomes were incubated at 37° C. for 48 h to allow for protein synthesis to occur. NanoSight® particle tracking analysis of electroporated exosomes revealed the same previously described peak of 100 nm, demonstrating that exosomes integrity was not compromised with the electroporation process. However, only electroporated exosomes were detected using particle tracking analysis with a 488 nm laser, suggesting GFP protein expression. Electron microscopy analysis of exosomes with a gold-labeled antibody further showed GFP expression in electroporated exosomes (FIG. 6B). GFP expression in electroporated exosomes was confirmed by western blot analysis, and was not observed with the use of the protein translation inhibitor cycloheximide. Protein extracts from the donor cells were again used as positive controls, with a GFP band of equal size to that seen in exosomes observed in cells electroporated with the GFP plasmid. To probe the existence of de novo protein synthesis, MCF10A and MDA-MB-231-derived exosomes were incubated with [$^{35}$S] methionine. Autoradiography of protein extracts from exosomes cultured in the presence of [$^{35}$S] methionine, confirmed the incorporation of the amino acid into newly formed proteins (FIG. 6C). The incorporation of [$^{35}$S] methionine could be inhibited with the addition of cycloheximide, a known inhibitor of protein translation. The corresponding donor cells were also incubated with the [$^{35}$S] methionine and shown to incorporate it, as a positive control (FIG. 6C). Additionally, exosomes were electroporated with a bicistronic plasmid that expresses firefly luciferase in a 5' cap-dependent manner, and renilla luciferase in a cap-independent manner. Luminescence analysis demonstrated firefly luciferase activity in electroporated exosomes, demonstrating that they have the capability for classic eukaryotic cap-dependent translation.

Figure 7:
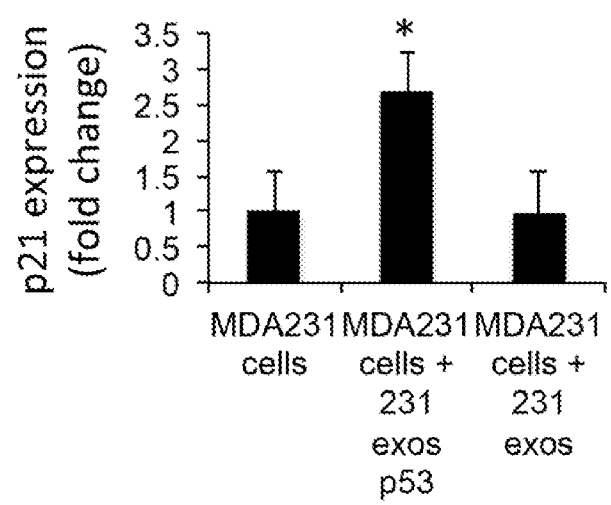
FIG. 7. A plasmid encoding a wild-type p53 protein was electroporated in MDA-MB-231-derived exosomes. After 48 h of cell-free culture, electroportaed exosomes were used to treat MDA-MB-231 cells pre-treated with cycloheximide, and p21 expression was evaluated as a downstream target of wild-type p53 function.

Having demonstrated the capacity of exosomes to synthesize proteins de novo, independently from their original cells, it was next determined if this could result in the delivery of newly formed functional proteins to recipient cells. Exosomes previously electroporated with a GFP plasmid were incubated with normal human fibroblasts treated with cycloheximide, and as such with their translation ability impaired. Observing exosomes-treated fibroblasts with confocal microscopy, green signal was detected when the cells were treated with exosomes electroporated with GFP but not with control exosomes. This confirmed that newly synthesized proteins in exosomes can be delivered to recipient cells. To further confirm that proteins translated in exosomes are functionally active when delivered to recipient cells, studies were performed with MDA-MB-231 cells. This cell line is known to express a mutant inactive form of the tumor suppressor gene p53 (Gartel et al., 2003). p53 can act in response to DNA damage to induce expression of p21, leading to cell cycle arrest (Zilfou and Lowe, 2009). Exosomes from MDA-MB-231 cells were electroporated with a plasmid encoding a wild-type form of p53 and incubated for 48 h to allow for translation to occur. Incubating electroporated exosomes back with the donor MDA-MB-231 cells led to an increase in p21 gene expression (FIG. 7). This suggests that a functional form of p53, newly translated in the exosomes, was delivered to the cells. Therefore, exosomes from mammalian cells have the capacity to translate functional proteins and deliver them to recipient cells.

Platelets have the ability to produce proteins from mRNAs left after megakaryocyte differentiation in response to stimuli (Weyrich et al., 2004). In neurobiology, small foci of translation, including polyribosomes and mRNA binding proteins, have been observed on the dendritic spines of large neurons, along the synaptic region (Steward and Levy, 1982; Wells, 2006). Some biological structures have, therefore, acquired biosynthetic capacity remotely from the genetic center of the cell in order to support their biological function. However, this is the first and only report of extracellular protein translation. It comes in the wake of other recent observations that suggest an unexpected level of biological activity within exosomes. Exosomes from bovine milk infected with bovine leukemia virus, for example, have recently been shown to have reverse transcriptase activity (Yamada et al., 2013). Recent data further show that exosomes derived from cancer cells can generate miRNAs from their precursors. The biological significance of the existence of protein translation within exosomes remains to be elucidated. It is known, however, that cells can selectively incorporate mRNAs into exosomes (Raposo and Stoorvogel, 2013). This raises the intriguing possibility that mRNAs selectively packaged into exosomes could be translated into proteins whose expression is repressed in their cell of origin. This could have potential implications in terms of biomarker evaluation as well as therapeutic harnessing of exosomes.

EXAMPLE 5

GPC1 is a Specific Surface Protein on Exosomes from Cancer Cells

Figure 8A:
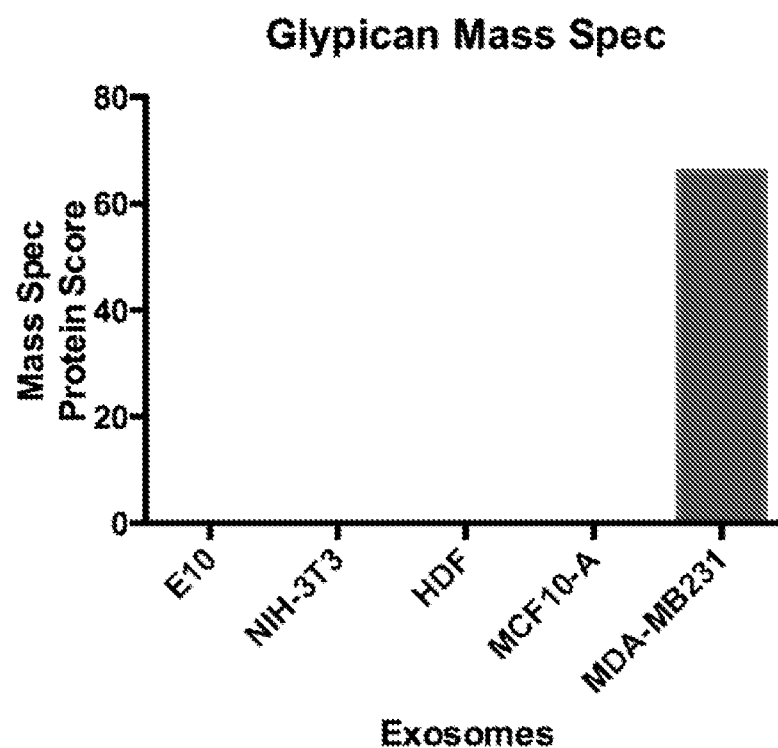
FIGS. 8A-C.
Figure 8B:
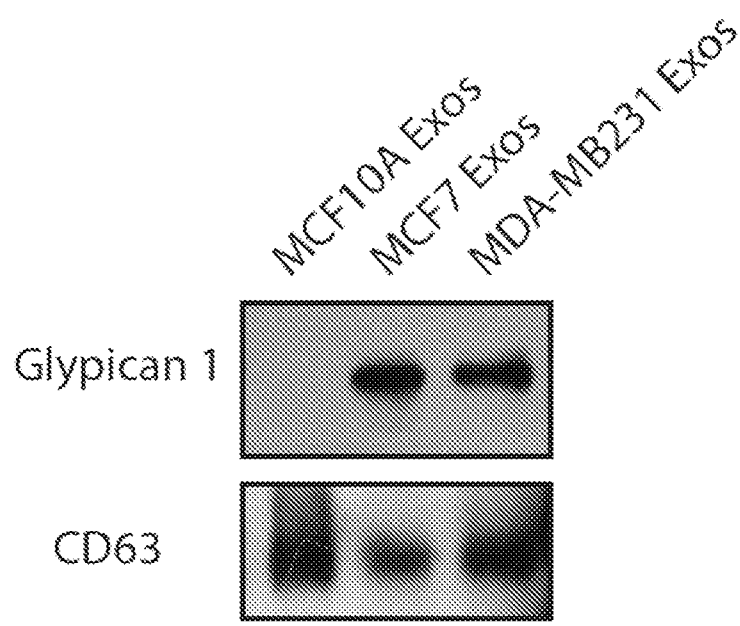
Figure 8C:
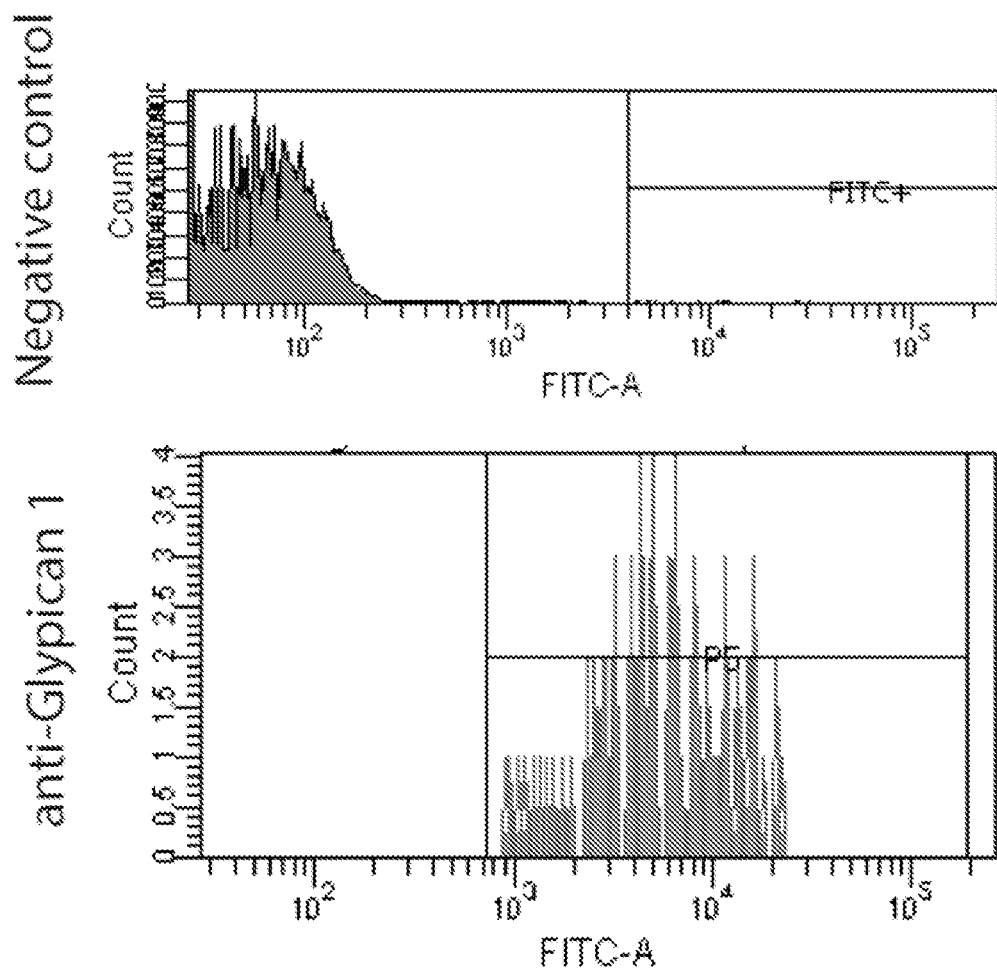

Cancer cell-derived exosomes were specifically identified using the protein marker glypican 1, which is a surface marker present on exosomes derived from cancer cells but not normal cells. Mass spectrometry was performed on exosomes derived from various cell lines, both cancerous and non-tumorigenic. The presence of glypican 1 protein was noted exclusively on cancer cell-derived exosomes and not on others (FIG. 8A). Immunoblot analysis was performed and showed glypican 1 protein expression in cancer-derived exosomes and not in non-tumorigenic cell-derived exosomes (FIG. 8B). Flow cytometry analysis was performed and showed glypican 1 expression at the surface of cancer-derived exosomes (FIG. 8C).

Figure 9A:
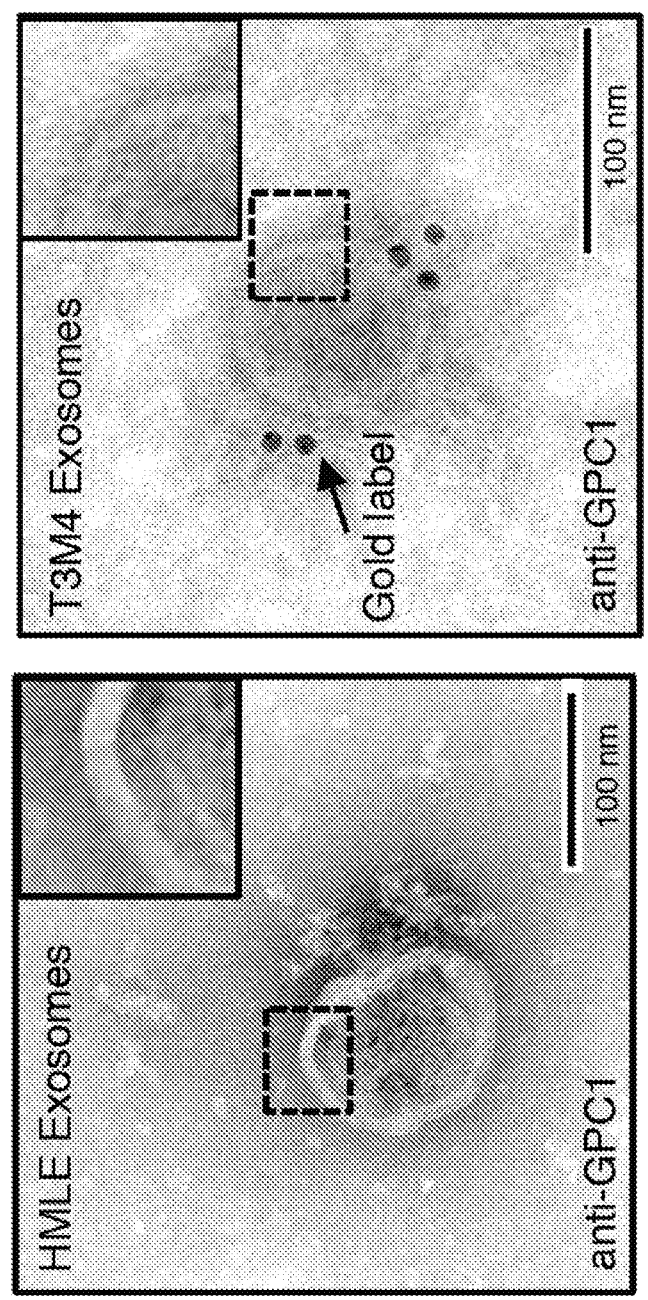
FIGS. 9A-E. GPC1 is present specifically on cancer exosomes.
Figure 9B:
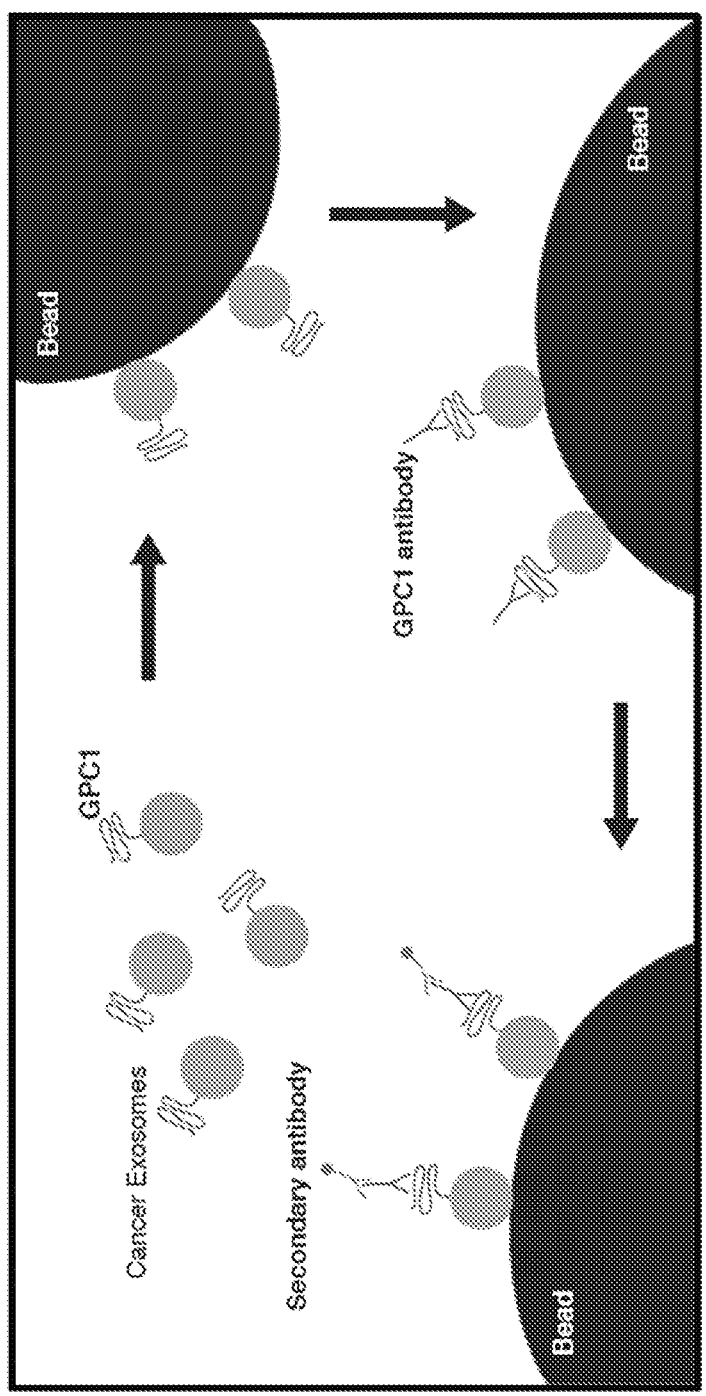
Figure 9C:
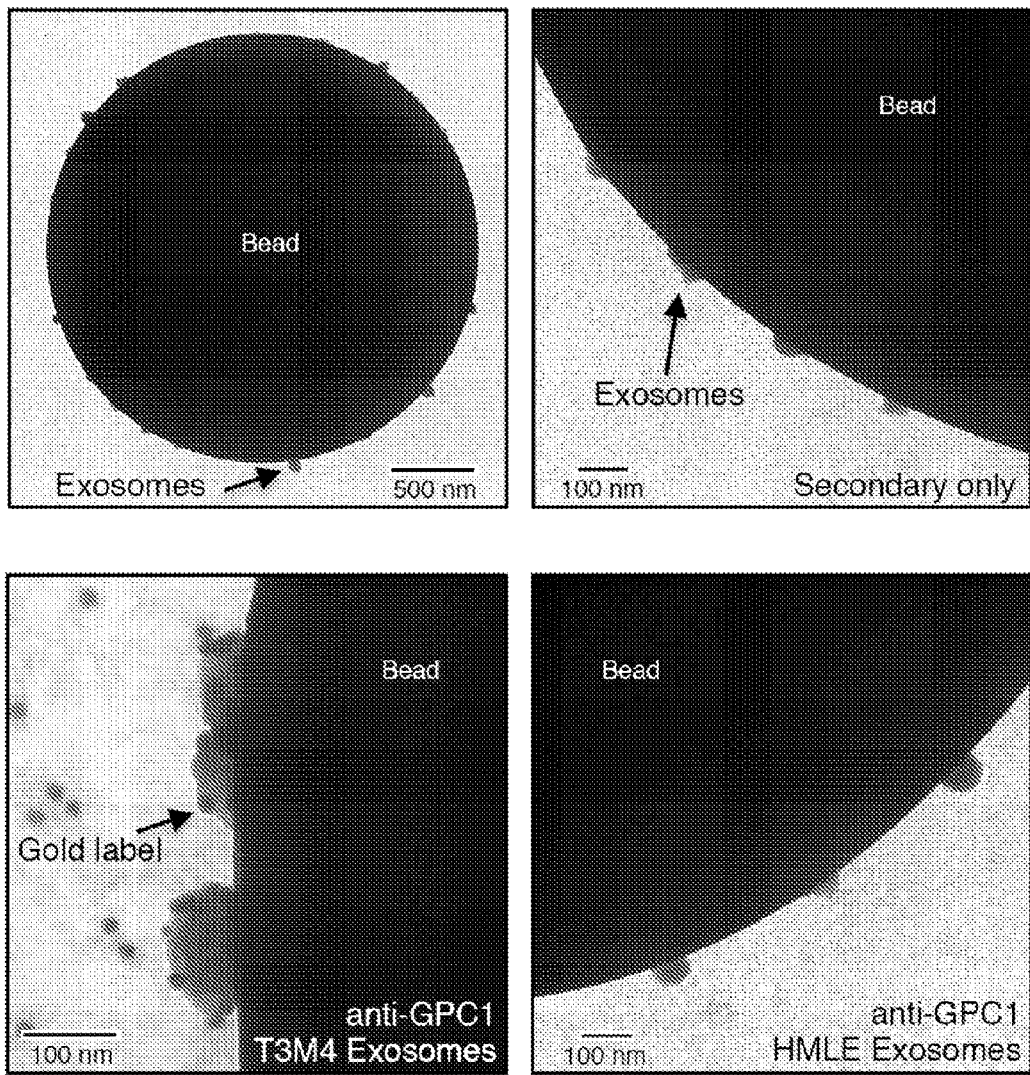
Figure 14D:
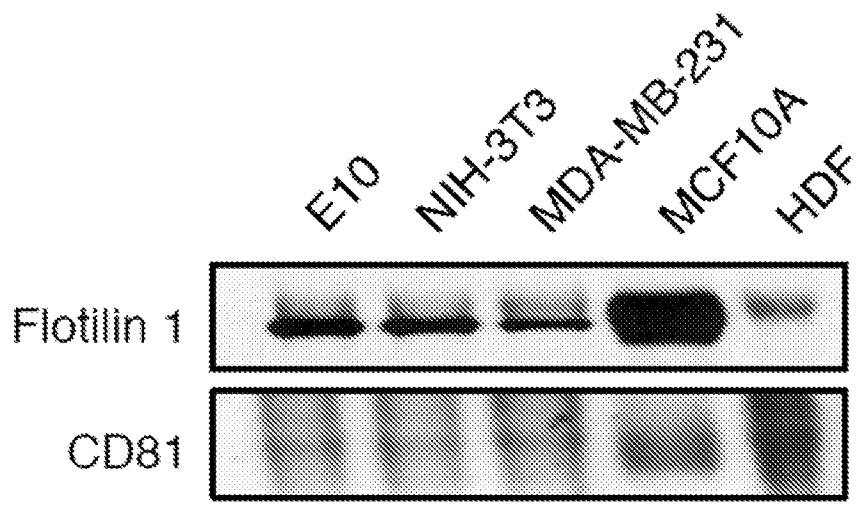

Exosomes from cancer cells (MDA-MB-231, triple negative human metastatic breast carcinoma), fibroblasts (HDF, human dermal fibroblasts; NIH/3T3, mouse embryonic fibroblasts), and non-tumorigenic epithelial cells (MCF 10A, human mammary epithelial cells; E10, mouse lung epithelial cells) were isolated using established ultracentrifugation methods (Luga et al., 2012; Thery et al., 2006). The harvested exosomes were analyzed by NanoSight® nanoparticle tracking analysis and transmission electron microscopy (TEM), which revealed a range of 105±5 nm and 112±4 nm in diameter, respectively (FIGS. 14A-B) (Thery et al., 2002). The exosomes purity was assessed using detection of CD9 by immunogold labeling and TEM (FIG. 14C) and western blot analysis for flotillin1 and CD81 (FIG. 14D) (Thery et al., 2002). The exosomes proteome was evaluated using ultra performance liquid chromatography-mass spectrometry (UPLC-MS) (Wilson et al., 2005). A total of 1120 proteins were found in all exosomes from all cell types (HDF, NIH/3T3, E10, MCF 10A, and MDA-MB-231), including the exosomes markers TSG101, CD9, and CD63 (total number of proteins in each exosomes type were: HDF=261, NIH/3T3=171, E10=232, MCF 10A=214, and MDA-MB-231=242). Bioinformatics analysis revealed 48 proteins (25 cytoplasmic, 7 nuclear, 5 transmembrane, 1 membrane-anchored, and 7 secreted) exclusively present in the cancer cell-derived exosomes (MDA-MB-231; Table 1). Among these, Glypican-1 (GPC1) emerged as the only membrane anchored protein that was also reported as over-cell lines (FIGS. 9B-D and FIG. 14H). Different exosomes purification methods confirmed the specific presence of GPC1 on cancer exosomes isolated from diverse cancer cell lines (FIG. 9E).

TABLE 1

Proteins exclusively present in MDA-MB-231 cancer cell-derived exosomes

Figure 10A:
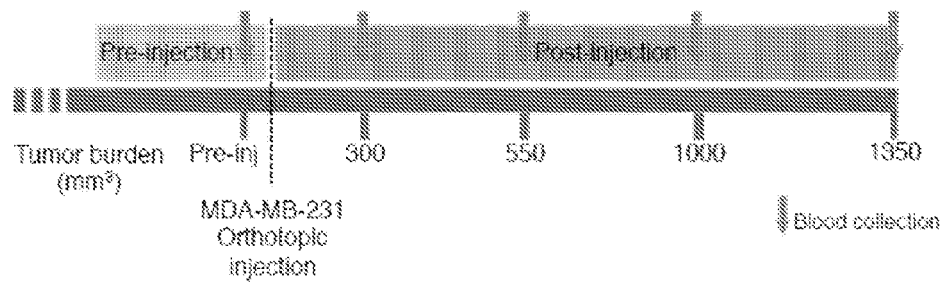
FIGS. 10A-F. GPC1$^+$ circulating exosomes (crExos) derived from cancer cells in tumor-bearing mice.
Figure 10B:
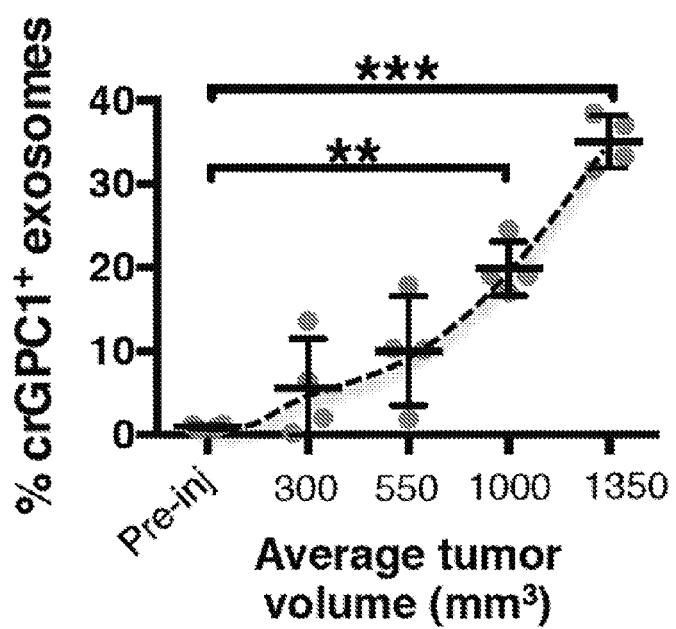
Figure 10C:
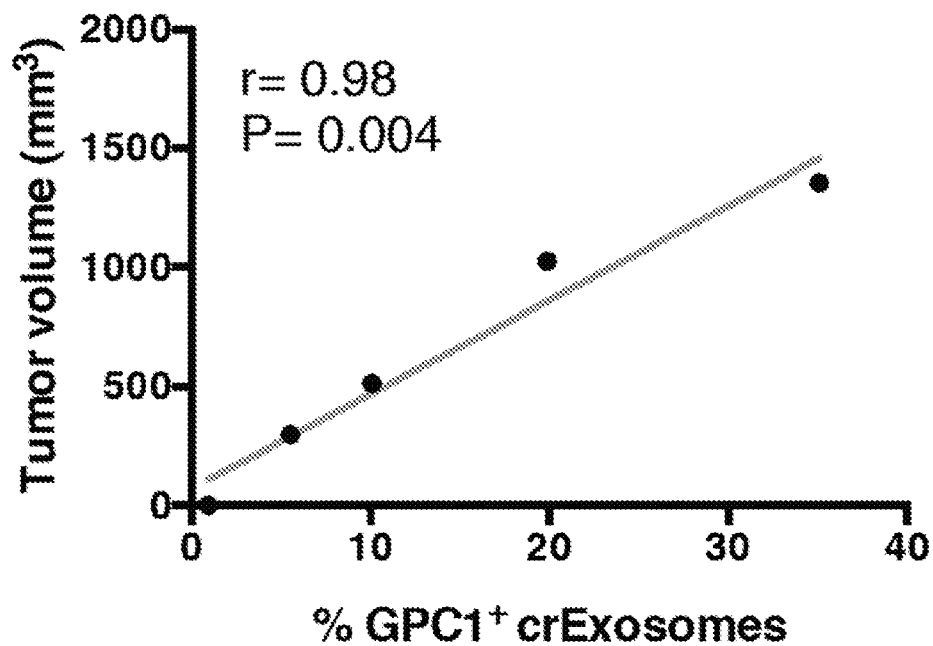
Figure 10D:
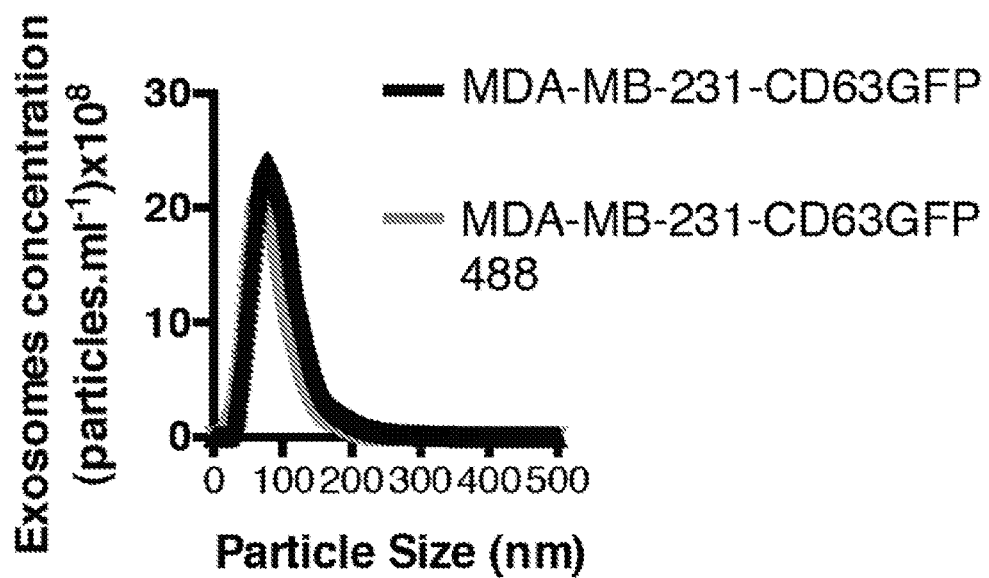
Figure 10E:
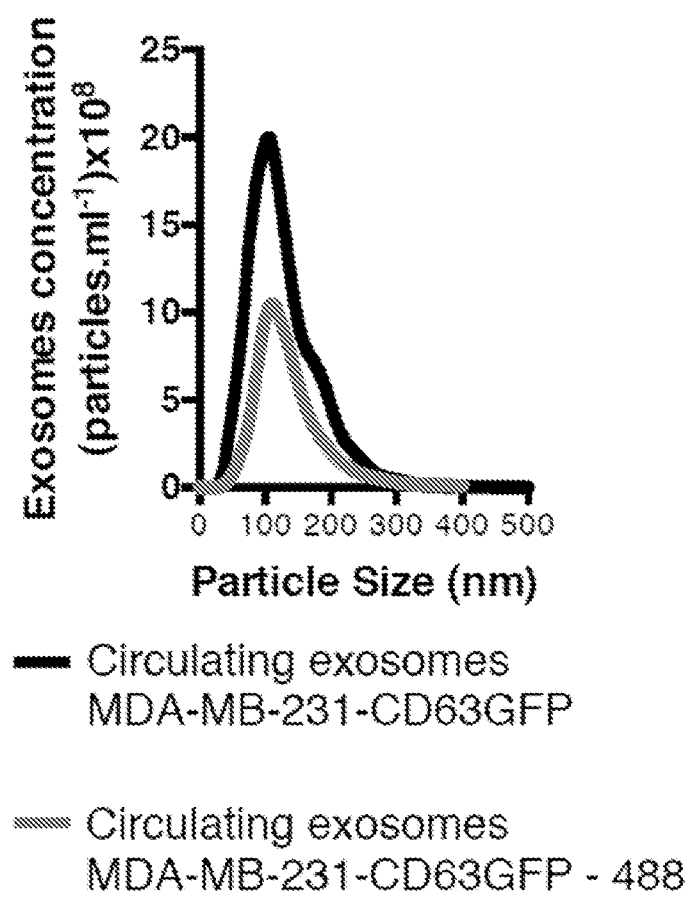
Figure 14E:
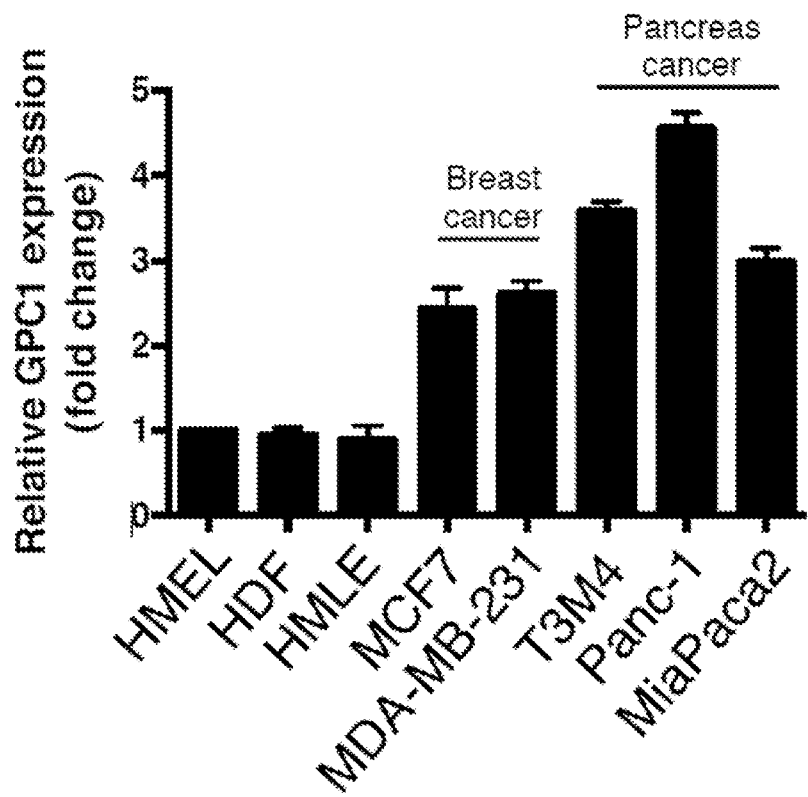
Figure 14F:
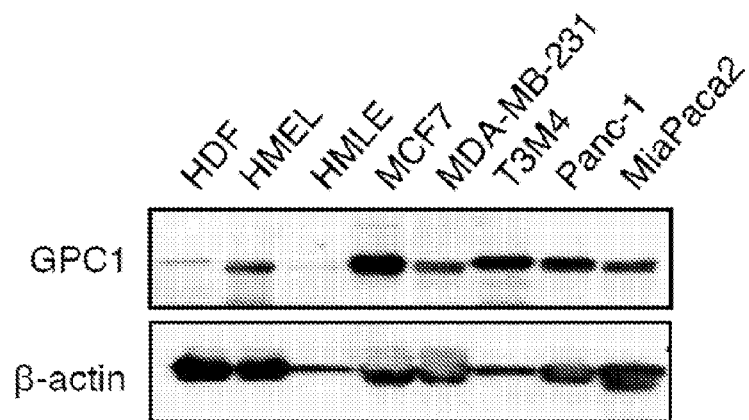
Figure 14G:
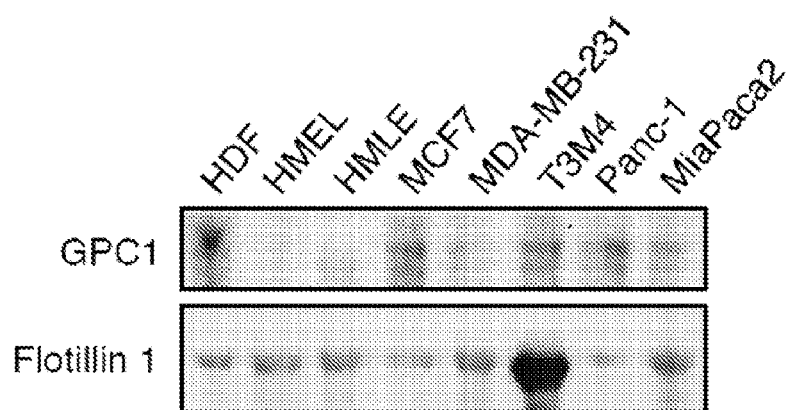
Figure 14H:
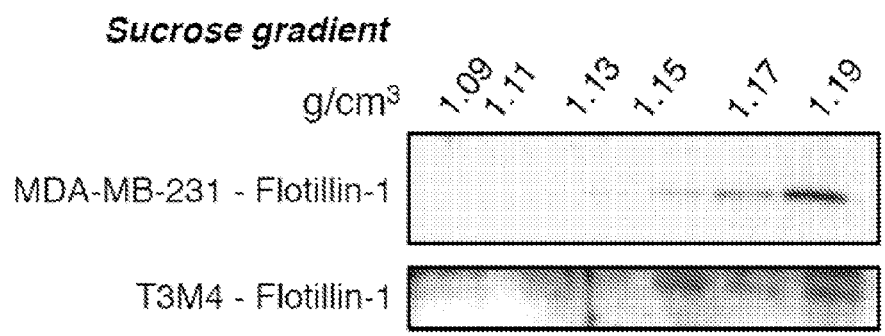

| Protein Name | Gene ID | Cellular Location |
|---|---|---|
| ATP-binding cassette sub-family A member 6 | ABCA6 | Transmembrane |
| Tetraspanin-4 | TSPAN4 | Transmembrane |
| SLIT and NTRK-like protein 4 | SLITRK4 | Transmembrane |
| Putative protocadherin beta-18 | PCDHB18 | Transmembrane |
| Myeloid cell surface antigen CD33 | CD33 | Transmembrane |
| Glypican-1 | GPC1 | Membrane anchored |
| Histone H2A type 2-A | HIST1H2AA | Nucleus |
| Histone H2A type 1-A | HIST1H1AA | Nucleus |
| Histone H3.3 | H3F3A | Nucleus |
| Histone H3.1 | HIST1H3A | Nucleus |
| Zinc finger protein 37 homolog | ZFP37 | Nucleus |
| Laminin subunit beta-1 | LAMB1 | Secreted |
| Tubulointerstitial nephritis antigen-like | TINAGL1 | Secreted |
| Peroxiredoxin04 | PRDX4 | Secreted |
| Collagen alpha-2(IV) chain | COL4A2 | Secreted |
| Putative protein C3P1 | C3P1 | Secreted |
| Hemicentin-1 | HMCN1 | Secreted |
| Putative rhophilin-2-like protein | RHPN2P1 | Not specified |
| Ankyrin repeat domain-containing protein 62 | ANKRD62 | Not specified |
| Tripartite motif-containing protein 42 | TRIM42 | Not specified |
| Junction plakoglobin | JUP | Cytoplasm |
| Tubulin beta-2B chain | TUBB2B | Cytoplasm |
| Endoribonuclease Dicer | DICER1 | Cytoplasm |
| E3 ubiquitin-protein ligase TRIM71 | TRIM71 | Cytoplasm |
| Katanin p60 ATPase-containing subunit A-like 2 | KATNAL2 | Cytoplasm |
| Protein S100-A6 | S100A6 | Cytoplasm |
| 5'-nucleotidase domain-containing protein 3 | NT5DC3 | Cytoplasm |
| Valine-tRNA ligase | VARS | Cytoplasm |
| Kazrin | KAZN | Cytoplasm |
| ELAV-like protein 4 | ELAVL4 | Cytoplasm |
| RING finger protein 166 | RNF166 | Cytoplasm |
| FERM and PDZ domain-containing protein 1 | FRMPD1 | Cytoplasm |
| 78 kDa glucose-regulated protein | HSPA5 | Cytoplasm |
| Trafficking protein particle complex subunit 6A | TRAPPC6A | Cytoplasm |
| Squalene monooxygenase | SQLE | Cytoplasm |
| Tumor susceptibility gene 101 protein | TSG101 | Cytoplasm |
| Vacuolar protein sorting 28 homolog | VPS28 | Cytoplasm |
| Prostaglandin F2 receptor negative regulator | PTGFRN | Cytoplasm |
| Isobutyryl-CoA dehydrogenase, mitochondrial | ACAD8 | Cytoplasm |
| 26S protease regulatory subunit 6B | PSMC4 | Cytoplasm |
| Elongation factor 1-gamma | EEF1G | Cytoplasm |
| Titin | TTN | Cytoplasm |
| Tyrosine-protein phosphatase type 13 | PTPN13 | Cytoplasm |
| Triosephosphate isomerase | TPI1 | Cytoplasm |
| Ccarboxypeptidase E | CPE | Cytoplasm | expressed in a variety of cancers, including breast and pancreas cancer (Table 1) (Matsuda et al., 2001; Kleeff et al., 1998; Su et al., 2006). GPC1 expression was elevated in several breast and pancreas cancer cell lines compared to non-tumorigenic cells (FIGS. 14E-F). In contrast to exosomes derived from non-tumorigenic cell lines, GPC1 protein was only detected in cancer cell-derived exosomes by immunoblotting analysis (FIG. 14G). Additionally, GPC1$^+$ exosomes were detected by immunogold TEM in cancer exosomes (T3M4 pancreas cancer line) but not in non-cancer exosomes (HMLE; FIG. 9A). FACS analysis of exosomes coupled to aldehyde/sulphate beads was used to detect GPC1 protein at the surface of exosomes (FIG. 9B) Immunogold and TEM showed cancer exosomes at the surface of beads with GPC1 expression while non-tumorigenic exosomes did not show GPC1 expression (FIG. 9C). Additionally, exosomes derived using sucrose gradients from cell lines identified GPC1 expression in cancer exosomes but not on exosomes derived from non-tumorigenic To determine whether GPC1$^+$ exosomes could be isolated from systemic circulation of tumor-bearing mice, MDA-MB-231 human breast cancer cells were implanted in the mammary fat pads of nude mice. The mice were bled prior to cancer cell inoculation, and repeatedly again when tumors reached an average volume of 300, 550, 1000, and 1350 mm$^3$, and circulating exosomes (crExos) were assessed for the presence of GPC1 (FIG. 10A). The relative percentage of GPC1$^+$ crExos increased proportionally with tumor growth and correlated with tumor burden (FIGS. 10B-C; r=0.98, P=0.004). To further confirm the cancer cell origin of GPC1$^+$ crExos, MDA-MB-231 cells were engineered to stably express GFP under the promoter of CD63, an established exosomal marker (Thery et al., 2006). Cancer exosomes secreted by these cells (MDA-MB-231-CD63GFP) in culture were positive for GFP (FIG. 10D). Following orthotopic implantation of MDA-MB-231-CD63GFP cells in nude mice, crExos were collected from mice with tumors with a size of ~1500 mm$^3$. A select population of crExos was found to be GFP+ (FIG. 10E), and only cancer-cell specific GFP+ crExos were positive for GPC1 as it was not detected in GFP− crExos (FIG. 10F).

EXAMPLE 6

GPC1+ Exosomes are a Biomarker for the Presence of Cancer

Figure 9D:
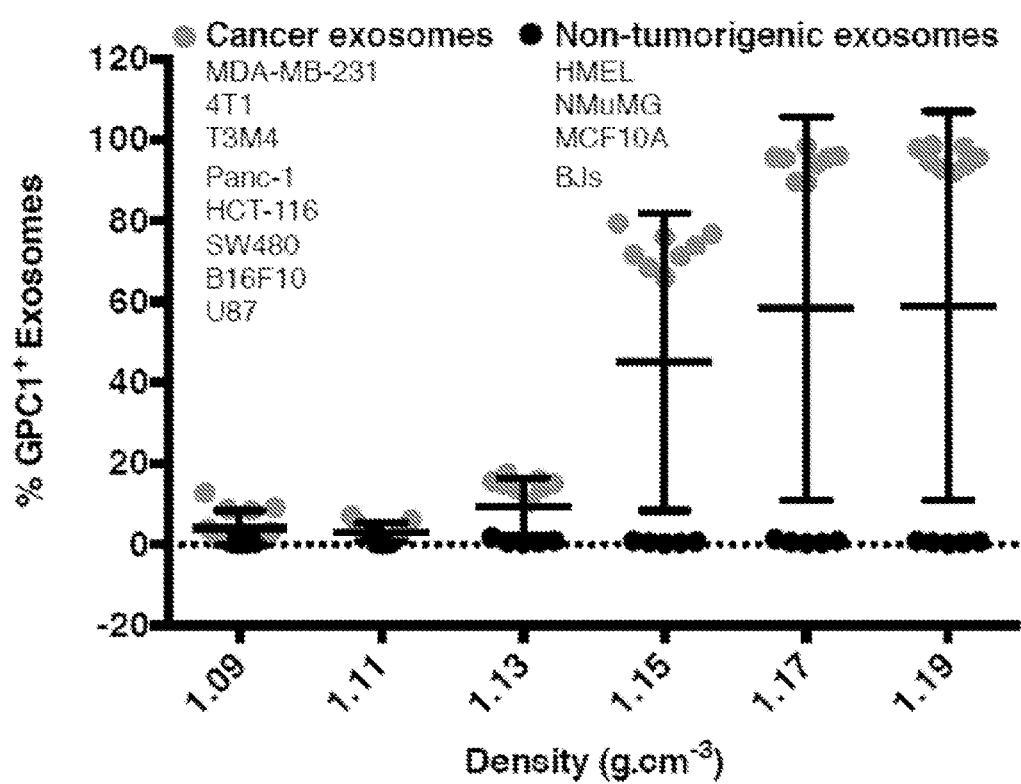
Figure 9E:
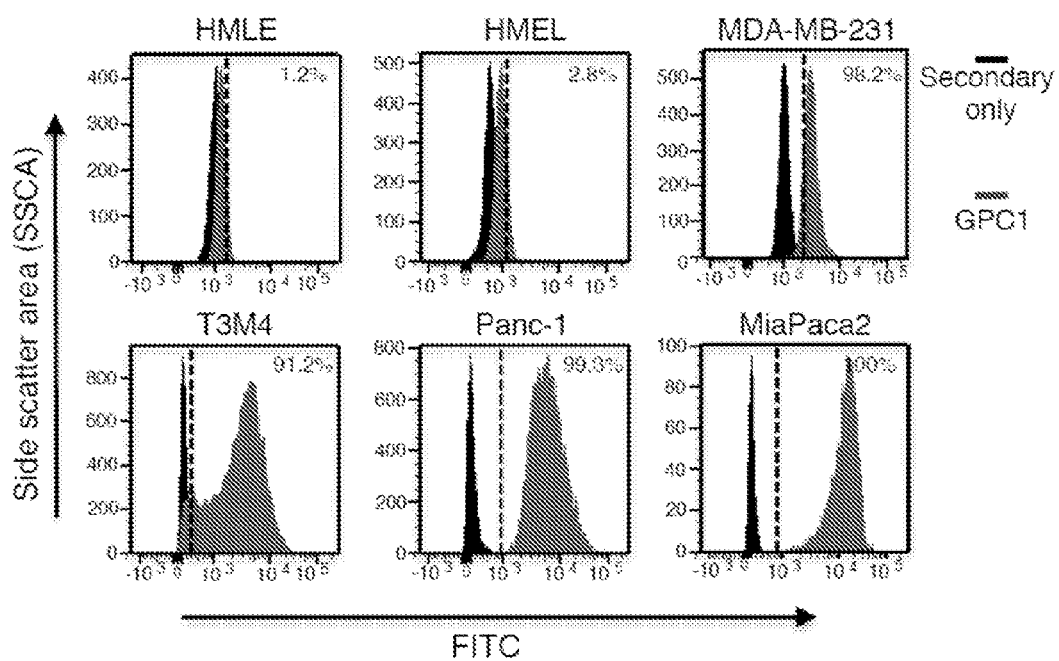
Figure 10F:
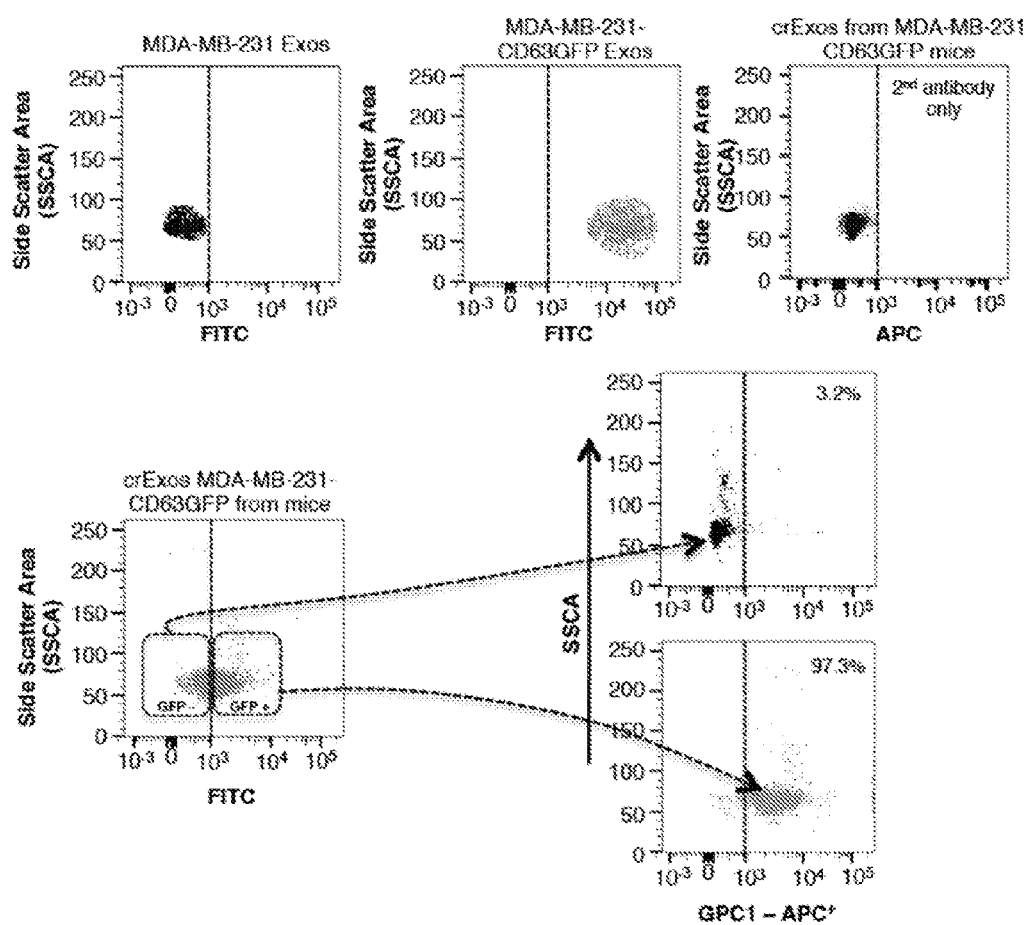
Figure 11C:
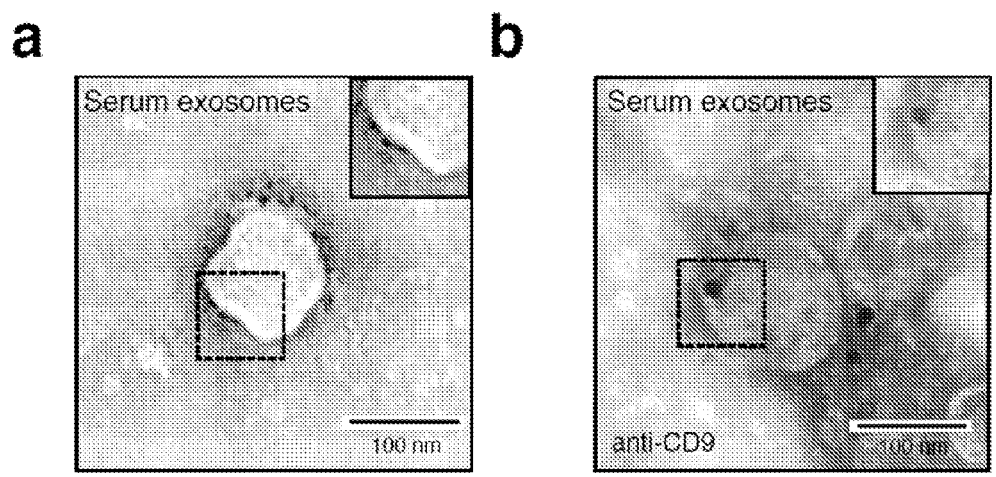
Figure 11C:
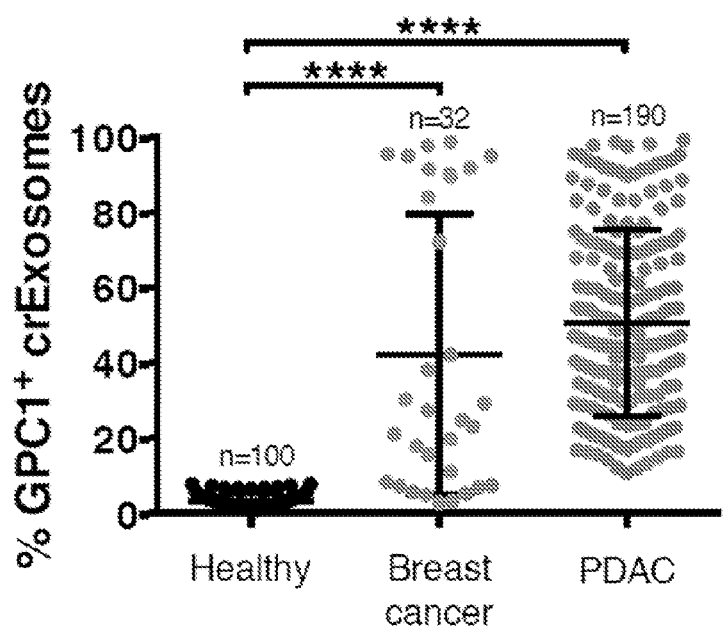
Figure 15A:
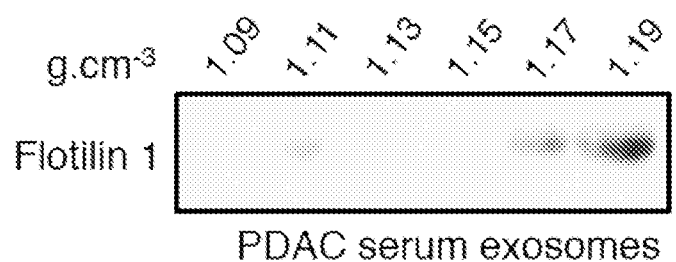
FIGS. 15A-C. NanoSight® analysis in human serum samples.
Figure 15B:
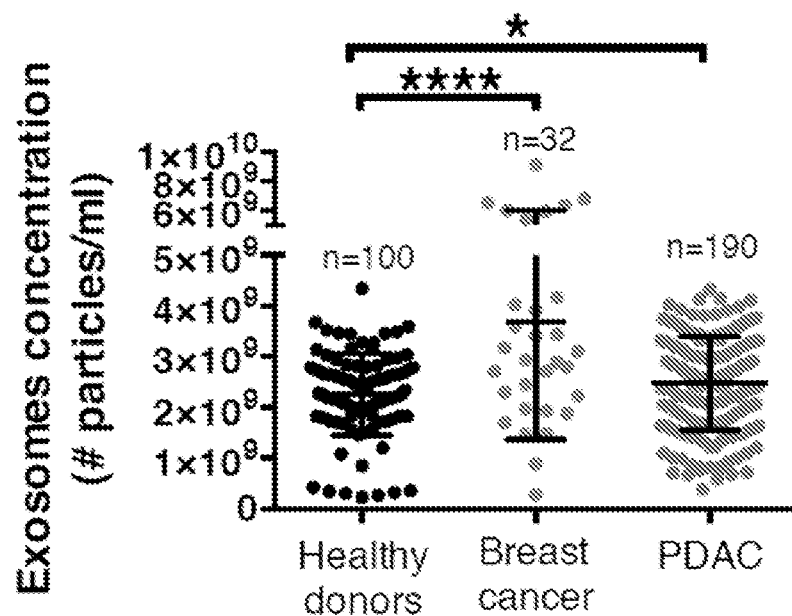
Figure 15C:
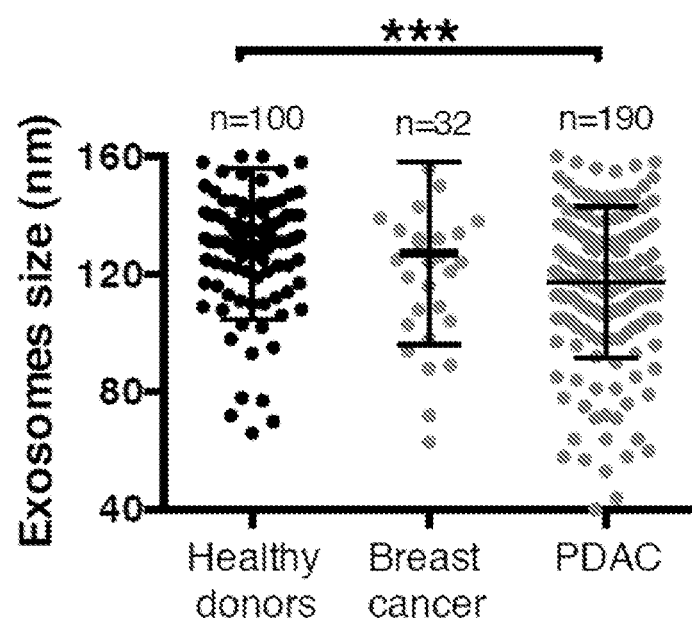

Exosomes derived from cancer cell lines and circulating exosomes from tumor-bearing mice were 100% positive for GPC1 (FIG. 9D and FIG. 10F). Next, crExos were isolated from patients with breast cancer (n=32), pancreatic ductal adenocarcinoma (PDAC, n=190), and healthy donors (n=100) (patient data are shown in Table 2). TEM analyses of crExos purified from serum by ultracentrifugation revealed a lipid bilayer as well as CD9 positivity (FIGS. 11A-B). crExos purified by sucrose gradient isolation also showed expression of exosomes marker flotillin1 (FIG. 15A) (Thery et al., 2002; Thery et al., 2006). Interestingly, the relative concentration of crExos was significantly higher in the sera of cancer patients compared to healthy individuals (FIG. 15B), and the average size of PDAC crExos was significantly smaller compared to all other crExos (breast cancer patients and healthy donors, FIG. 15C). Analyses of sera from healthy individuals revealed baseline positivity for GPC1 in crExos, ranging from 0.3% to 4.7% (average of 2.3%). Twenty-four out of 32 (75%) breast cancer patients demonstrated a level of crExos GPC1+ surpassing baseline levels noted in healthy individuals (P<0.0001; FIG. 15C). In contrast, all 190 PDAC crExos showed levels of GPC1+ crExos surpassing levels in healthy individuals (P<0.0001; FIG. 15C). These results indicate a strong correlation between GPC1+ crExos and cancer, particularly for PDAC.

TABLE 2

Demographics of patients and healthy participants

|  | No. of participants (n = 323) | % of participants | No. of participants (n = 32) | % of participants |
|---|---|---|---|---|
|  | Pancreatic Cancer | | Breast cancer | |
| Total | 190 | 58.82% | 32 | 100% |
| Sex | | | | |
| Men | 104 | 54.74% | 0 | 0% |
| Women | 86 | 45.26% | 32 | 100% |
| Median Age (range) | 66 (37-86) | | 57 (30-85) | |
| AJCC stage | | | | |
| 0 | n.a. | — | 2 | 6% |
| I | 2 | 1.05% | 12 | 38% |
| II | n.a | — | 17 | 53% |
| IIa | 19 | 10.00% | n.a. | — |
| IIb | 117 | 61.58% | n.a. | — |
| III | 11 | 5.79% | 1 | 3% |
| IV | 41 | 21.58% | n.a. | — |
| Tumor grade | | | | |
| 1 | 1 | 0.53% | 8 | 25% |
| 2 | 91 | 47.89% | 13 | 41% |
| 3 | 49 | 25.79% | 10 | 31% |
| 4 | 1 | 0.53% | n.a. | — |
| Unknown | 48 | 25.26% | 1 | 3% |
| Tumor resected | | | | |
| Yes | 152 | 80.00% | 32 | 100% |
| No | 38 | 20.00% | 0 | 0% |
| Neoadjuvant Radio-/Chemotherapy | | | | |
| Received | 10 | 5.26% | 0 | 0% |
| Not received | 180 | 94.74% | 32 | 100% |
| Benign Pancreatic disease (BPD) | | | | |
| Total | 26 | 8.05% | | |
| Sex | | | | |
| Men | 18 | 69.23% | | |
| Women | 8 | 30.77% | | |
| Median Age (range) | 58.5 (31-77) | | | |
| Diagnosis | | | | |
| Chronic pancreatits | 15 | 57.69% | | |
| Autoimmune pancreatitis | 3 | 11.54% | | |
| Serous cystadenoma | 8 | 30.77% | | |
| Pancreatic cancer precursor lesion (PCPL) | | | | |
| Total | 7 | 2.17% | | |

TABLE 2-continued

Demographics of patients and healthy participants

|  | No. of participants (n = 323) | % of participants | No. of participants (n = 32) | % of participants |
|---|---|---|---|---|
| Sex |  |  |  |  |
| Men |  |  | 3 | 42.86% |
| Women |  |  | 4 | 57.14% |
| Median Age (range) | 65 (46-74) |  |  |  |
| Neoplasms |  |  |  |  |
| IPMN |  |  | 5 | 71.43% |
| PanIN |  |  | 2 | 28.57% |
| Healthy donors |  |  |  |  |
| Total |  | 100 | 30.96% |  |

Abbreviations: American Joint Committee on Cancer (AJCC), Intraductal papillary mucinous neoplasm (IPMN), Pancreatic Intraepithelial Neoplasia (PanIN), not applicable (n.a.).

EXAMPLE 7

GPC1+ crExos Specifically Contain mRNA Encoding Oncogenic KRAS$^{G12D}$

Figure 11D:
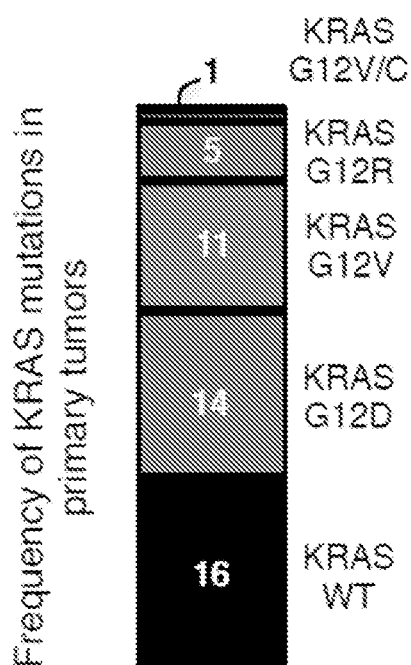
Figure 11E:
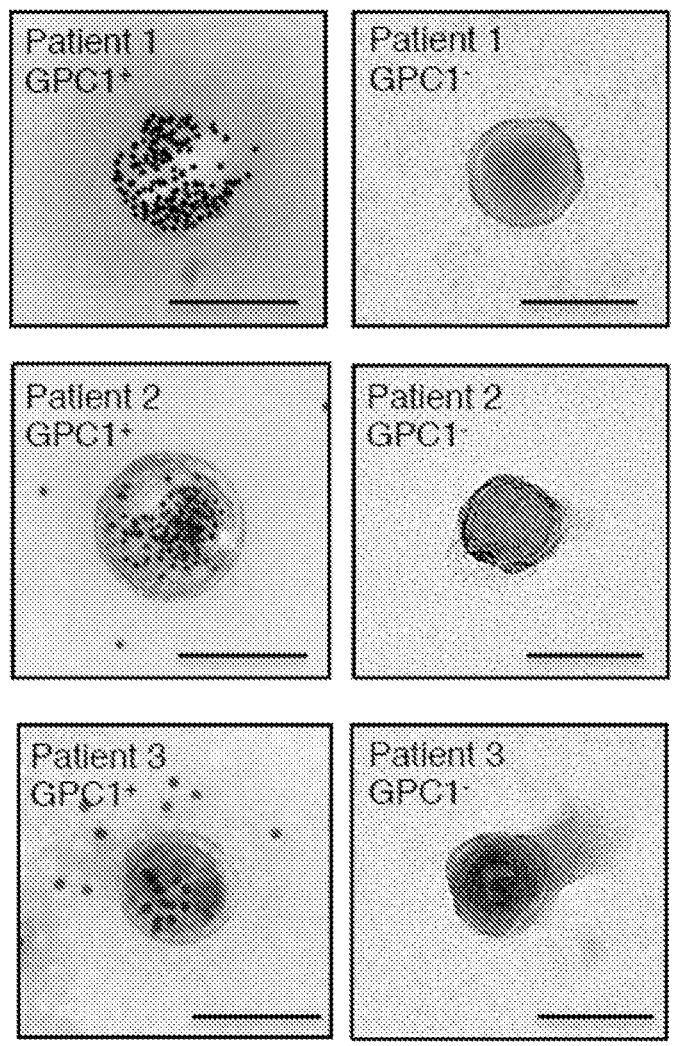
Figure 11F:
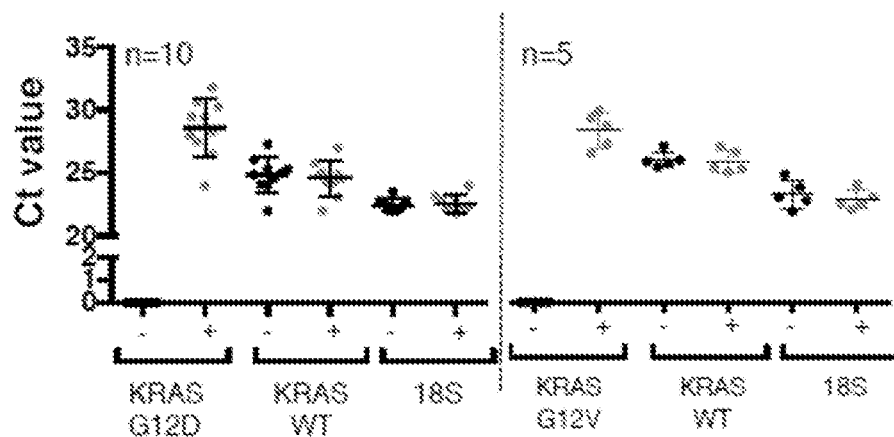

Exosomes can contain DNA and RNA (Kahlert and Kalluri, 2013). KRAS is a frequently mutated gene in pancreatic cancer and mutated transcripts have been found in circulation (Skog et al., 2008; Morris et al., 2010; Chen et al., 2013). Primary tumor samples from 47 patients with PDAC were sequenced to assess oncogenic KRAS status. Sixteen PDAC tumors contained only the wild-type KRAS allele, 14 had a G12D mutated allele, 11 had a G12V mutated allele, five had a G12R mutated allele, and one contained a G12V/C mutation (FIG. 11D). Sufficient amounts of corresponding serum were available from 10 patients with KRAS$^{G12D}$ mutations and five with KRAS$^{G12V}$ mutations. GPC1+ crExos and GPC1− crExos from these patients were subjected to immunogold TEM to confirm specific GPC1 expression (FIG. 11E). All 15 GPC1+ crExos with tumor validated oncogenic KRAS mutation revealed identical mutation by qPCR analysis of exosomal mRNA using specific primers (FIG. 11F). Wild-type KRAS mRNA was found both in GPC1+ and GPC1− crExos (FIG. 11F).

EXAMPLE 8

GPC1+ Circulating Exosomes Detect Early Stage Pancreas Cancer

Figure 11G:
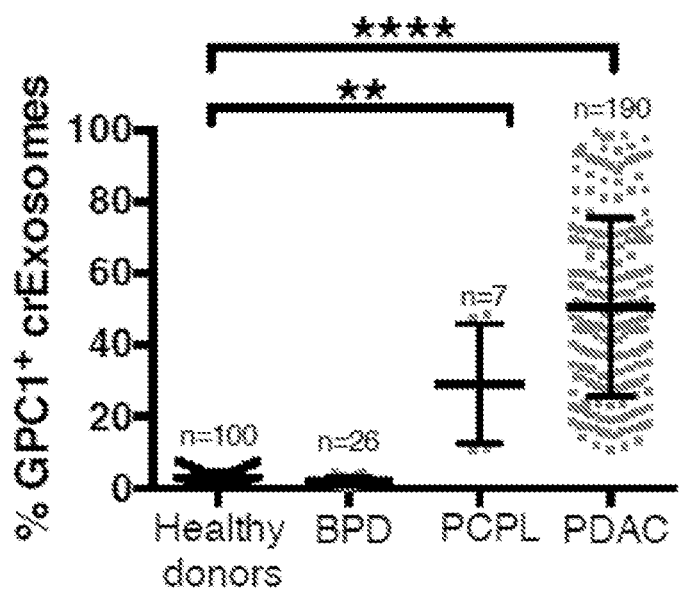

Further analysis of sera from seven patients with histologically-validated pancreatic cancer precursor lesions (PCPL) and sera from 26 patients with histologically-validated benign pancreatic disease (BPD) indicated that levels of GPC1+ crExos could distinguish patients with PCPL from healthy individuals and patients with BPD (FIG. 11G). Specifically, GPC1+ crExos in the PCPL group (PaNIN, n=2; IPMN, n=5) was always greater than the healthy donor group (P=0.0061) and also significantly higher than GPC1+ crExos in the BPD group (which includes 18 patients with chronic pancreatitis and eight with cystic adenomas; FIG. 11G). The BPD group exhibited similar GPC1+ crExos levels (average 2.1% GPC1+ crExos) compared to healthy donors (FIG. 11G).

Figure 11H:
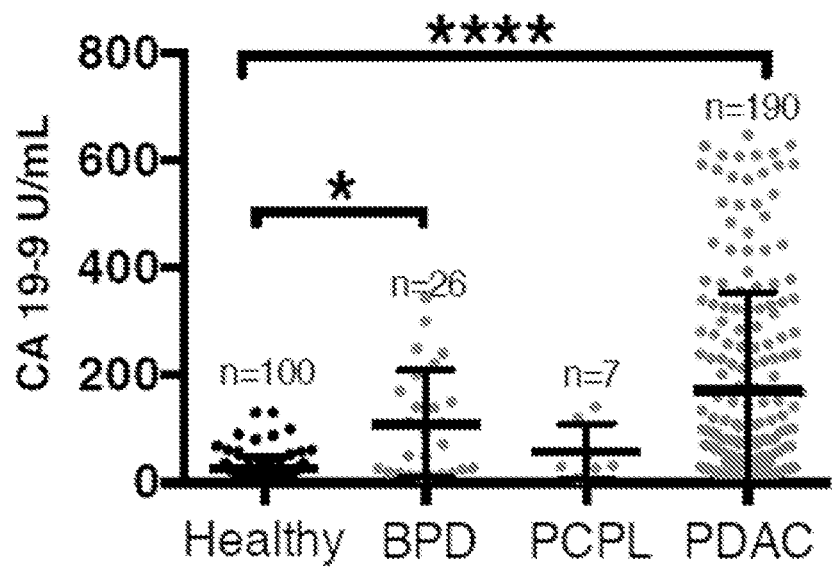
Figure 11I:
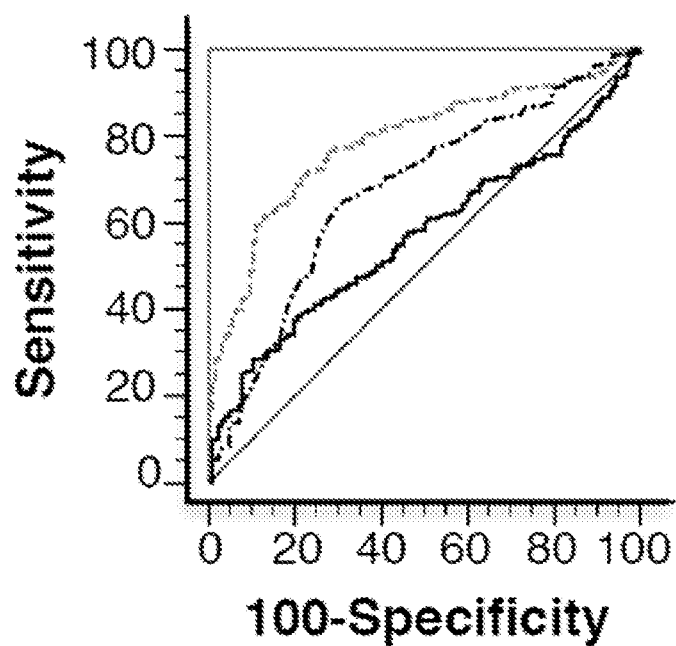

The specificity and sensitivity of GPC1+ crExos was compared with CA 19-9, a circulating protein currently used as a tumor marker for patients with pancreatic adenocarcinoma (Del Villano et al., 1983). CA 19-9 levels were elevated in the serum of patients with PDAC when compared to healthy donors, but CA19-9 levels were also significantly elevated in the serum of patients with benign pancreatic diseases (P<0.0001; FIG. 11H). Importantly, CA 19-9 serum levels failed to distinguish patients with PCPL from healthy donors (FIG. 11H). Receiver operating characteristic (ROC) curves indicated that GPC1+ crExos revealed a near perfect classifier with an AUC of 1.0 (95% CI: 0.988-1.0), a sensitivity of 100% (95% CI: 98.1-100%), a specificity of 100% (95% CI: 97.1-100%), a positive predictive value of 100% (95% CI: 98.1-100%), and a negative predictive value of 100% (95%: 86.8-100%; FIG. 11I), when comparing patients with pancreatic cancer stage I to IV with healthy donors and patients with benign pancreatic disease (FIGS. 11I and 16A-E; Tables 3-8). In contrast, CA 19-9 was inferior in distinguishing between patients with pancreatic cancer and healthy controls (AUC of 0.739, 95% CI: 70.2-82.6%, P<0.001; FIGS. 11I and 16A-E; Tables 3-8). Of note, neither the concentration of exosomes nor the size of exosomes was a valid parameter to stratify patients with pancreatic cancer versus controls (FIGS. 11G, 11I, and 16A-E; Tables 3-8). GPC1+ crExos showed a sensitivity and specificity of 100% in each stage of pancreatic cancer (carcinoma-in-situ, stage I as well as stages II-IV), supporting its utility at all stages of pancreatic cancer progression and emphasizing its potential role in early detection of pancreatic cancer.

TABLE 3

Receiver operating characteristic (ROC) curve analysis (corresponds to FIG. 11I)

| Parameter | AUC | CI | Cut-off value | Sensitivity | 95% CI | Specificity | 95% CI |
|---|---|---|---|---|---|---|---|
| GPC 1+ exosomes (%) | 1 | 0.998-1.00 | >7.6 | 100 | 98.1-100.0 | 100 | 97.1-100.0 |

TABLE 3-continued

Receiver operating characteristic (ROC) curve analysis (corresponds to FIG. 11I)

| Parameter | AUC | CI | Cut-off value | Sensitivity | 95% CI | Specificity | 95% CI |
|---|---|---|---|---|---|---|---|
| CA 19-9 (U/mL) | 0.739 | 0.687-0.787 | >26.3063 | 76.84 | 70.2-82.6 | 64.29 | 55.3-72.6 |
| Exosomes Concentration (^10E09) | 0.57 | 0.513-0.625 | >32.8 | 25.79 | 19.7-32.6 | 92.06 | 85.9-96.1 |
| Exosomes Size (nm) | 0.676 | 0.621-0.727 | ≤122 | 63.16 | 55.9-70.0 | 70.63 | 61.9-78.4 |

TABLE 4

Figure 16A:
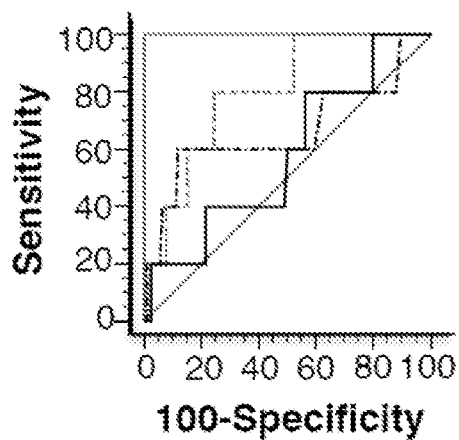
FIGS. 16A-E. Tumor stage-specific analysis.

Receiver operating characteristic (ROC) curve analysis (corresponds to FIG. 16A)

| Parameter | AUC | CI | Cut-off value | Sensitivity | 95% CI | Specificity | 95% CI |
|---|---|---|---|---|---|---|---|
| GPC 1+ exosomes (%) | 1 | 0.972-1.00 | >7.6 | 100 | 47.8-100.0 | 100 | 97.1-100.0 |
| CA 19-9 (U/mL) | 0.735 | 0.651-0.808 | >30.8435 | 80 | 28.4-99.5 | 66.67 | 57.7-74.8 |
| Exosomes Concentration (^10E09) | 0.581 | 0.492-0.667 | ≤23.75E08 | 60 | 14.7-94.7 | 43.65 | 34.8-52.8 |
| Exosomes Size (nm) | 0.663 | 0.576-0.744 | ≤107 | 60 | 14.7-94.7 | 88.1 | 81.1-93.2 |

TABLE 5

Figure 16B:
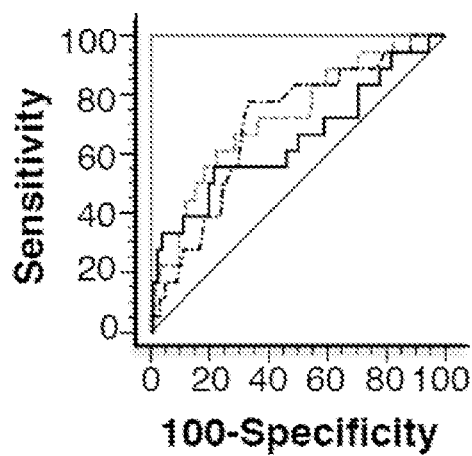

Receiver operating characteristic (ROC) curve analysis (corresponds to FIG. 16B)

| Parameter | AUC | CI | Cut-off value | Sensitivity | 95% CI | Specificity | 95% CI |
|---|---|---|---|---|---|---|---|
| GPC 1+ exosomes (%) | 1 | 0.975-1.00 | >7.6 | 100 | 81.5-100.0 | 100 | 97.1-100.0 |
| CA 19-9 (U/mL) | 0.668 | 0.585-0.744 | >26.3063 | 66.67 | 41.0-86.7 | 64.29 | 55.3-72.6 |
| Exosomes Concentration (^10E09) | 0.648 | 0.564-0.726 | >28.1E08 | 55.56 | 30.8-78.5 | 78.57 | 70.4-85.4 |
| Exosomes Size (nm) | 0.7 | 0.619-0.774 | ≤124 | 77.78 | 52.4-93.6 | 66.67 | 57.7-74.8 |

TABLE 6

Figure 16C:
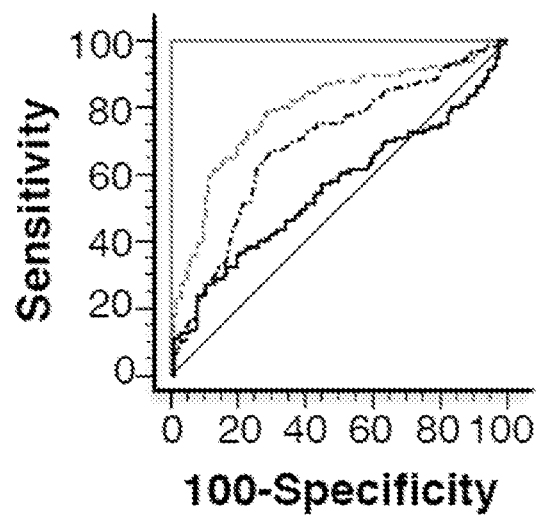

Receiver operating characteristic (ROC) curve analysis (corresponds to FIG. 16C)

| Parameter | AUC | CI | Cut-off value | Sensitivity | 95% CI | Specificity | 95% CI |
|---|---|---|---|---|---|---|---|
| GPC 1+ exosomes (%) | 1 | 0.985-1.00 | >7.6 | 100 | 96.9-100.0 | 100 | 97.1-100.0 |
| CA 19-9 (U/mL) | 0.74 | 0.680-0.794 | >25.3562 | 79.49 | 71.0-86.4 | 63.49 | 54.4-71.9 |
| Exosomes Concentration (^10E09) | 0.559 | 0.494-0.622 | >31.7E08 | 27.35 | 19.5-36.4 | 89.68 | 83.0-94.4 |
| Exosomes Size (nm) | 0.692 | 0.630-0.749 | ≤122 | 66.67 | 57.4-75.1 | 70.63 | 61.9-78.4 |

TABLE 7

Figure 16D:
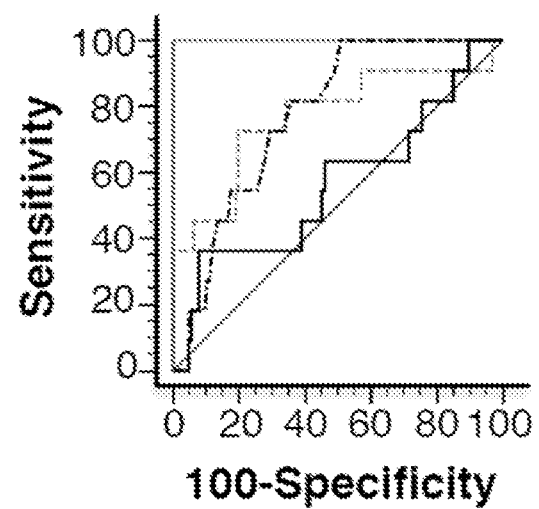

Receiver operating characteristic (ROC) curve analysis (corresponds to FIG. 16D)

| Parameter | AUC | CI | Cut-off value | Sensitivity | 95% CI | Specificity | 95% CI |
|---|---|---|---|---|---|---|---|
| GPC 1+ exosomes (%) | 1 | 0.973-1.00 | >7.6 | 100 | 71.5-100.0 | 100 | 97.1-100.0 |
| CA 19-9 (U/mL) | 0.729 | 0.646-0.801 | >36.1015 | 72.73 | 39.0-94.0 | 71.43 | 62.7-79.1 |

TABLE 7-continued

Receiver operating characteristic (ROC) curve analysis (corresponds to FIG. 16D)

| Parameter | AUC | CI | Cut-off value | Sensitivity | 95% CI | Specificity | 95% CI |
|---|---|---|---|---|---|---|---|
| Exosomes Concentration (^10E09) | 0.566 | 0.478-0.650 | >32.8E08 | 36.36 | 10.9-69.2 | 92.06 | 85.9-96.1 |
| Exosomes Size (nm) | 0.776 | 0.697-0.842 | ≤132 | 100 | 71.5-100.0 | 49.21 | 40.2-58.3 |

TABLE 8

Figure 16E:
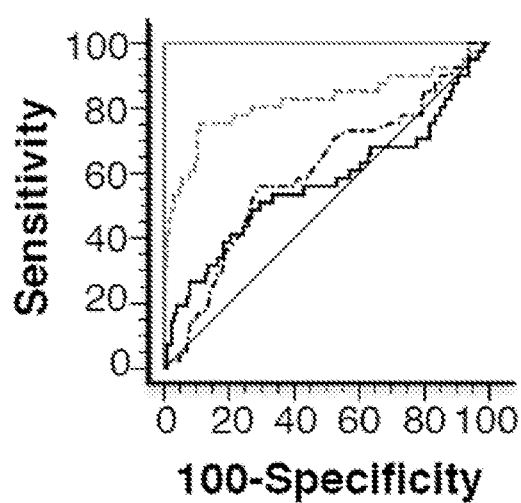

Receiver operating characteristic (ROC) curve analysis (corresponds to FIG. 16E)

| Parameter | AUC | CI | Cut-off value | Sensitivity | 95% CI | Specificity | 95% CI |
|---|---|---|---|---|---|---|---|
| GPC 1+ exosomes (%) | 1 | 0.978-1.00 | >7.6 | 100 | 91.4-100.0 | 100 | 97.1-100.0 |
| CA 19-9 (U/mL) | 0.788 | 0.718-0.848 | >61.2284 | 75.61 | 59.7-87.6 | 78.57 | 70.4-85.4 |
| Exosomes Concentration (^10E09) | 0.569 | 0.490-0.645 | >26.5E08 | 51.22 | 35.1-67.1 | 70.63 | 61.9-78.4 |
| Exosomes Size (nm) | 0.604 | 0.525-0.678 | ≤122 | 56.1 | 39.7-71.5 | 70.63 | 61.9-78.4 |

EXAMPLE 9

GPC1$^+$ Circulating Exosomes Inform Pancreatic Cancer Burden

Figure 12A:
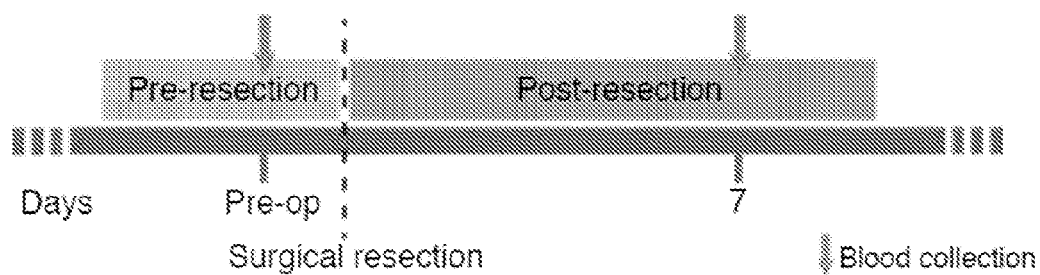
FIGS. 12A-F. GPC1+ crExos specifically carry KRAS G12D mRNA.
Figure 12B:
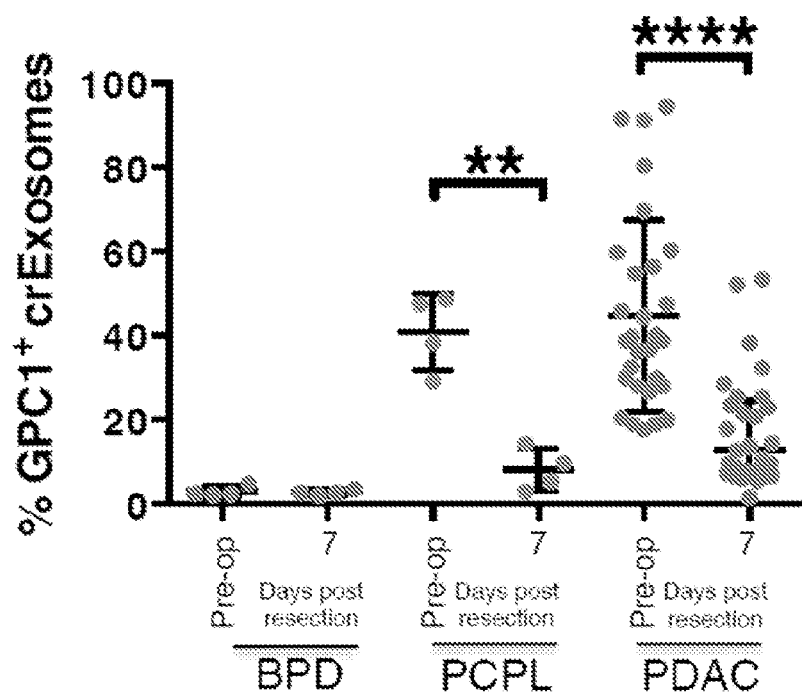
Figure 17A:
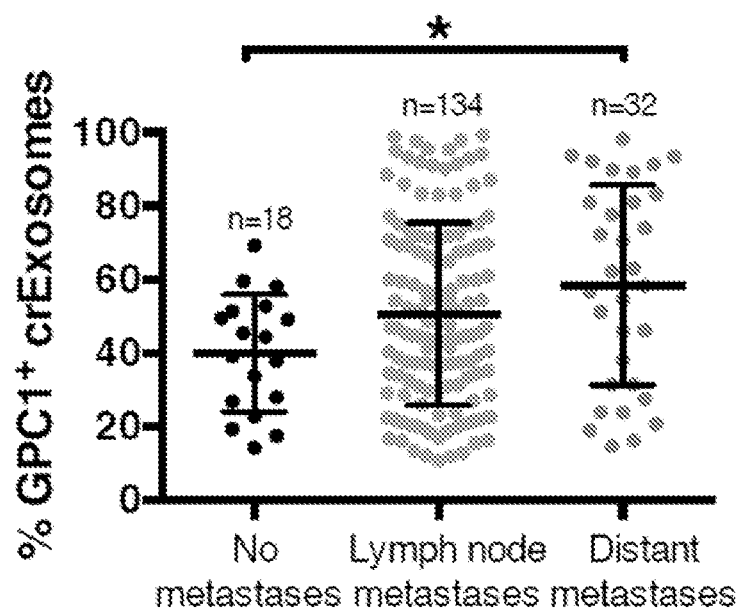
FIGS. 17A-B. Longitudinal human study.
Figure 17B:
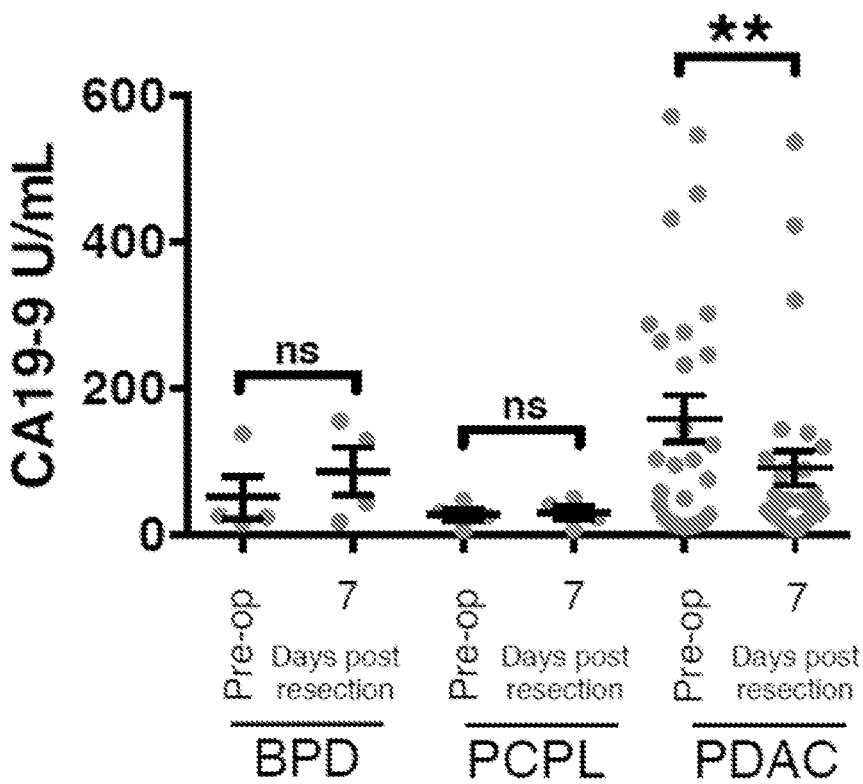

GPC1$^+$ crExos levels correlated with tumor burden in mice (FIGS. 10B-C). Therefore, whether GPC1$^+$ crExos levels could inform on metastatic disease burden of patients with PDAC was evaluated. GPC1$^+$ crExos of PDAC patients with distant metastatic disease showed significantly higher percentages of GPC1$^+$ crExos (average 58.5%) when compared to patients with metastatic disease restricted to lymph nodes (average 50.5%) or no known metastases (average 39.9%; FIG. 17A). Furthermore, GPC1$^+$ crExos were evaluated in serum of PDAC patients at pre-surgery and post-surgery stages (post operative day 7; PDAC n=29, PCPL n=4, and BPD n=4; FIG. 12A). Twenty-eight out of 29 PDAC patients and all PCPL patients with longitudinal blood collections showed a significant decrease in GPC1$^+$ crExos levels following surgical resection (PDAC: P<0.0001; PCPL: P<0.001; FIG. 12B). In contrast, CA 19-9 levels decreased in only 19 out of 29 PDAC patients and in none of the PCPL patients (PDAC: P=0.003; PCPL: P=0.81; FIG. 17B). In BPD patients, neither GPC1$^+$ crExos nor CA 19-9 showed a difference in pre- vs. post-resection (FIGS. 12B and 17B).

Figure 12C:
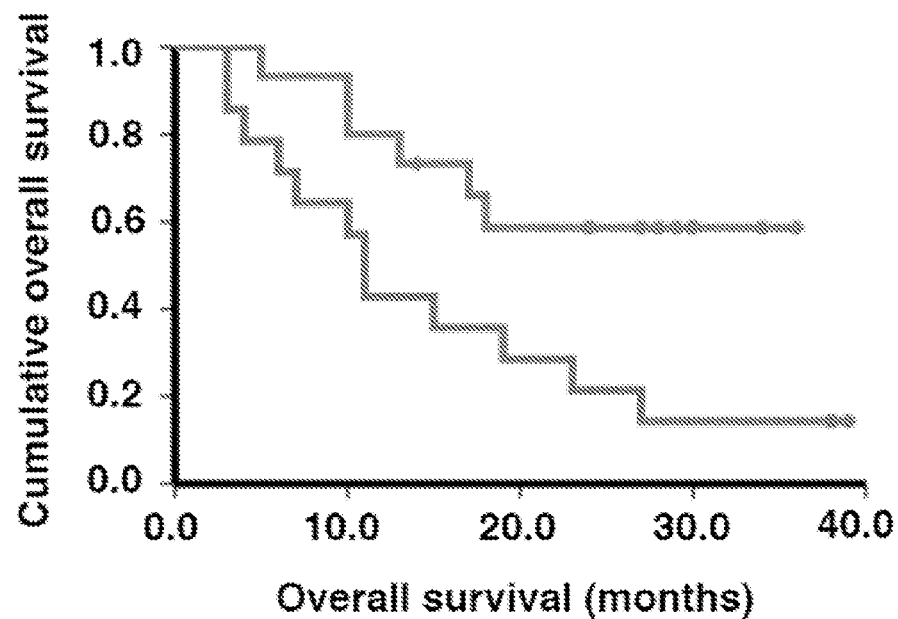
Figure 12D:
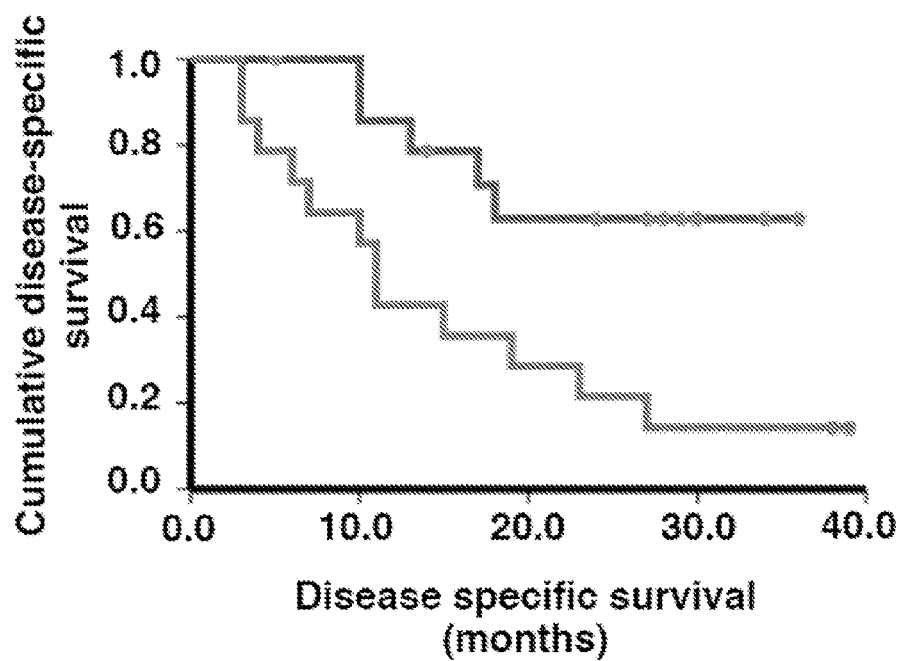
Figure 12E:
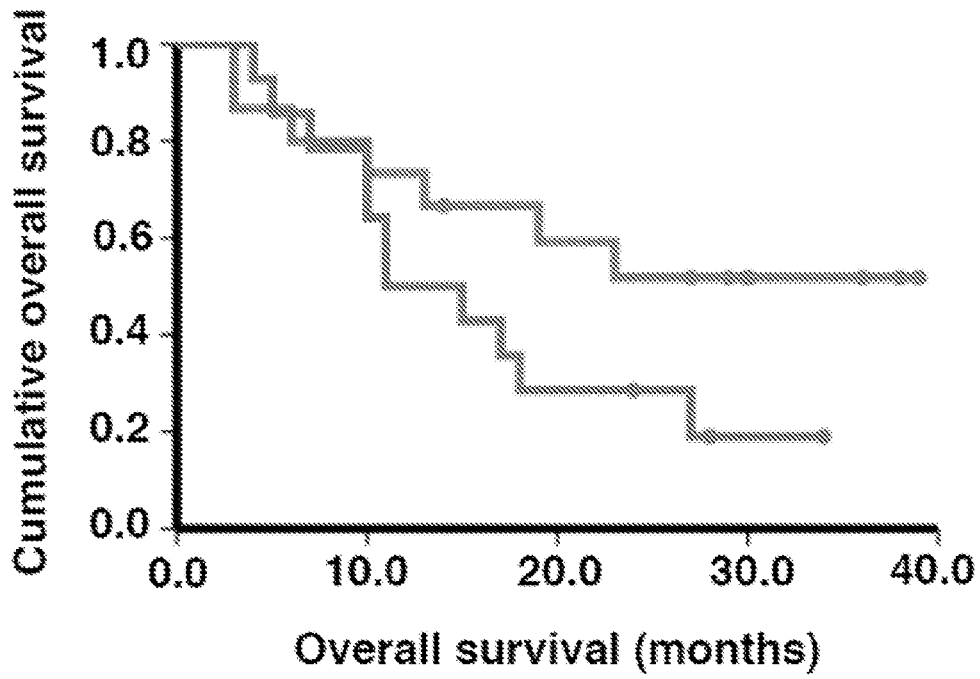
Figure 12F:
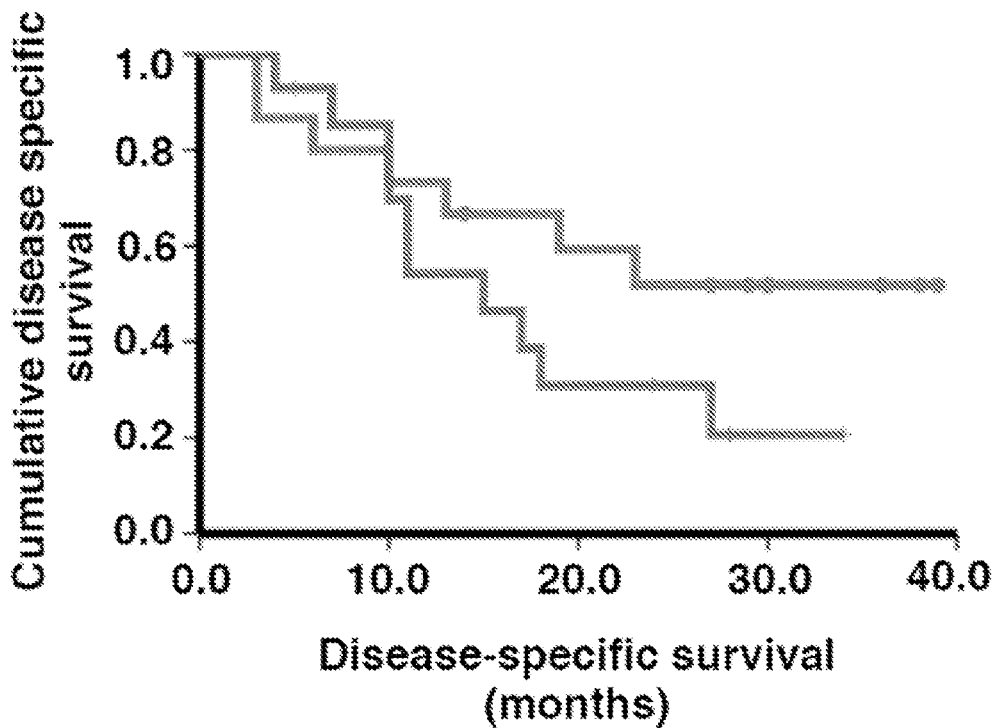

To determine the prognostic relevance of GPC1$^+$ crExos in the longitudinal study cohort, patients were dichotomized into two groups. Group 1 was defined by a decrease of GPC1$^+$ crExos greater than or equal to (≥) the median decrease in GPC1$^+$ crExos, and group 2 was defined by a decrease of GPC1$^+$ crExos less than (<) the median decrease of GPC1$^+$ crExos. Group 1 presented with improved overall (26.2 months) and disease-specific (27.7 months) survival compared to group 2 (15.5 months for both overall and disease specific), indicating that a greater decrease in GPC1$^+$ crExos after surgery is associated with increased survival (FIGS. 12C-D). While a decrease in CA 19-9 levels is noted when comparing between pre- and post-resection blood draws, this decrease did not significantly associate with overall and disease-specific survival (FIGS. 12E-F and 17B). Using a Cox regression model for a multivariate test to include the drop of GPC1$^+$ crExos, median age, AJCC stage, tumor grade, and CA 19-9 levels, only GPC1$^+$ crExos was revealed to be an independent prognostic and predictive marker for disease-specific survival (hazard ratio: 8.23, CI: 2.37-28.54, P=0.001; Tables 9 and 10).

TABLE 9

Multivariate analysis (Cox proportional hazards regression model) of prognostic parameters for overall survival in patients of the longitudinal cohort (n = 29) with pancreatic cancer

| Parameter | Hazard Ratio | 95% CI | P-value |
|---|---|---|---|
| GPC1 drop between day 0 and day 7 | 5.511 | 1.697-17.892 | 0.005 |
| Age | 0.96 | 0.898-1.026 | 0.227 |
| AJCC stage | 1.203 | 0.429-3.374 | 0.726 |
| Tumor grade | 1.024 | 1.004-1.044 | 0.018 |
| CA 19-9 drop between day 0 and day 7 | 2.453 | 0.885-6.796 | 0.084 |

Abbreviations: benign pancreatic disease (BPD), pancreatic cancer precursor lesion (PCPL), pancreatic ductal adenocarcinoma (PDAC), confidence interval (CI).

TABLE 10

Multivariate analysis (Cox proportional hazards regression model) of disease-specific survival in patients of the longitudinal cohort (n = 29) with pancreatic cancer

| Parameter | Hazard Ratio | 95% CI | P-value |
|---|---|---|---|
| GPC1 drop between day 0 and day 7 | 5.353 | 1.651-17.358 | 0.005 |
| Age | 0.962 | 0.899-1.028 | 0.254 |
| AJCC stage | 1.177 | 0.428-3.237 | 0.752 |
| Tumor grade | 1.016 | 0.992-1.041 | 0.197 |
| CA 19-9 drop between day 0 and day 7 | 2.138 | 0.762-5.993 | 0.149 |

Abbreviations: benign pancreatic disease (BPD), pancreatic cancer precursor lesion (PCPL), pancreatic ductal adenocarcinoma (PDAC), confidence interval (CI).

EXAMPLE 10

GPC1+ crExos can be Used to Detect Early PanIN Lesions

Figure 13A:
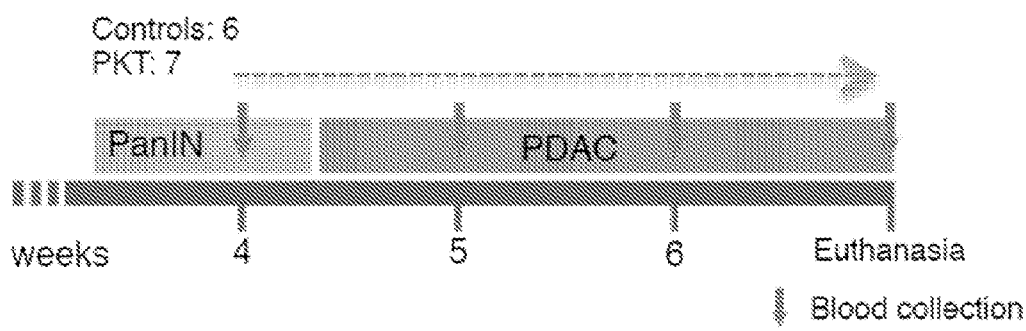
FIGS. 13A-G. GPC1+ crExos predict pancreas cancer in GEMM.
Figure 13B:
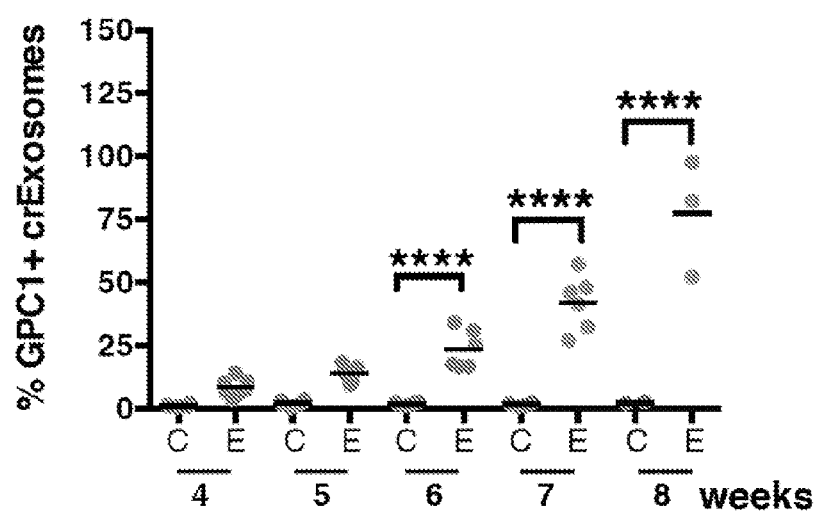
Figure 13C:
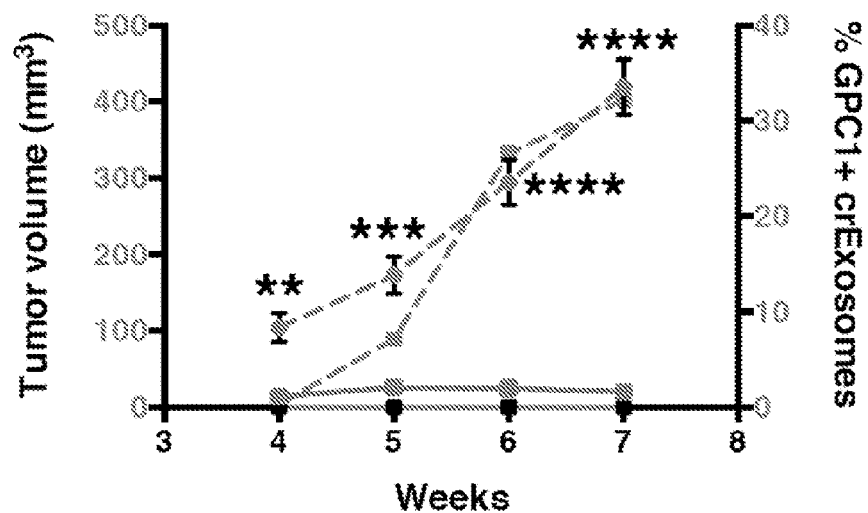
Figure 13D:
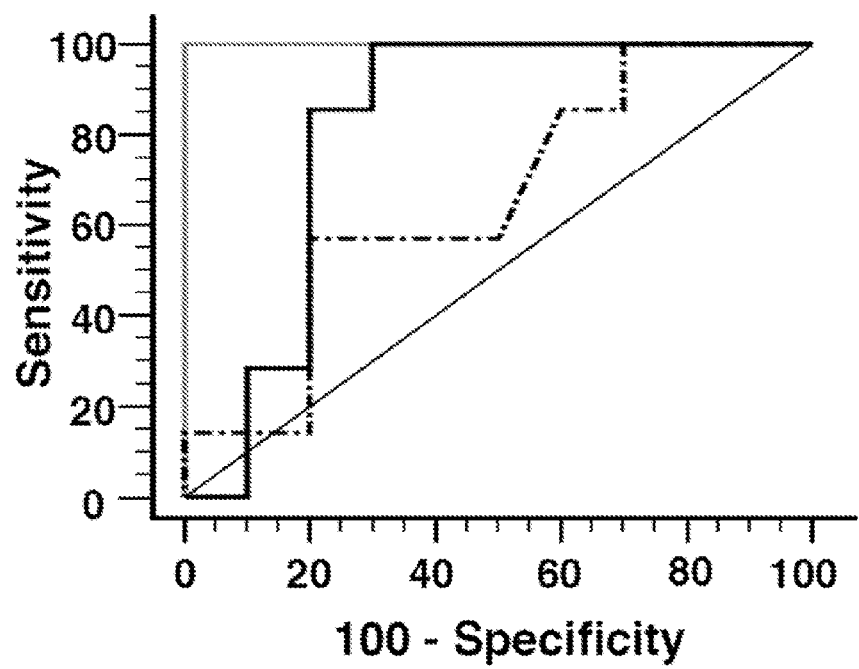
Figure 18A:
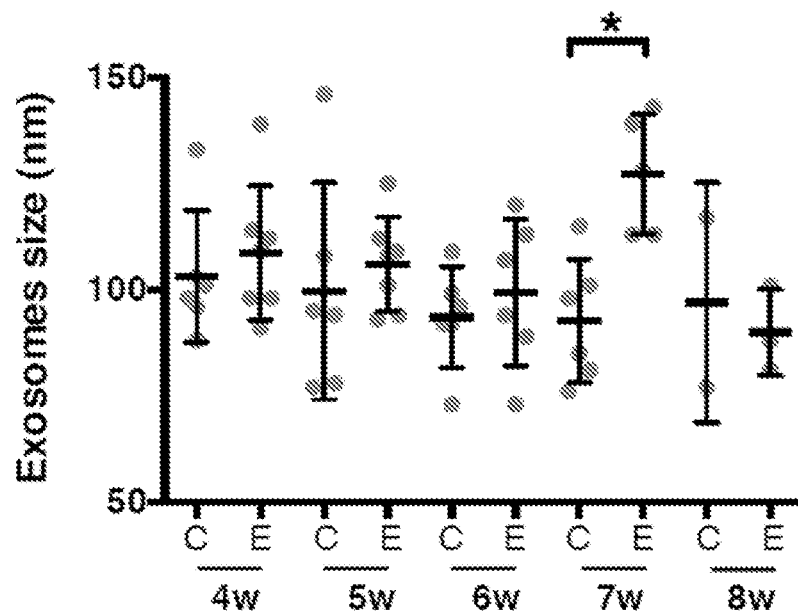
FIGS. 18A-D. PDAC GEMM longitudinal study.
Figure 18B:
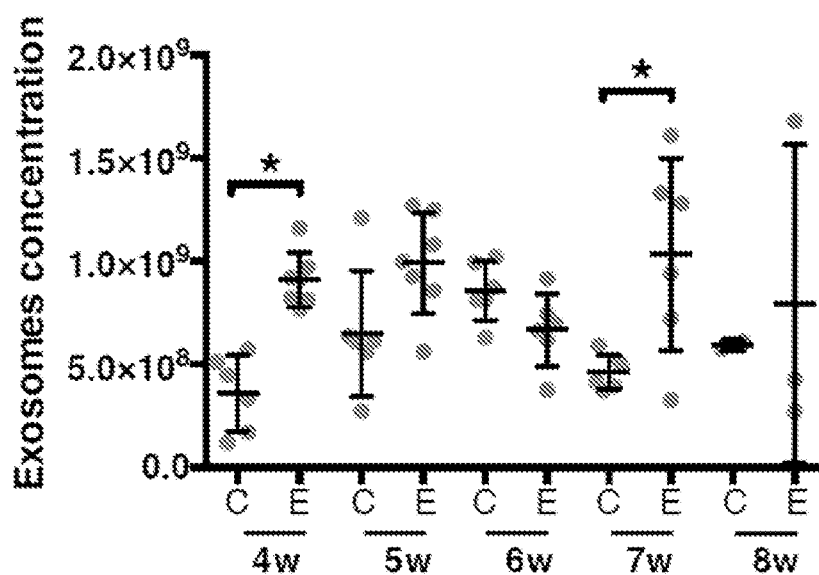
Figure 18C:
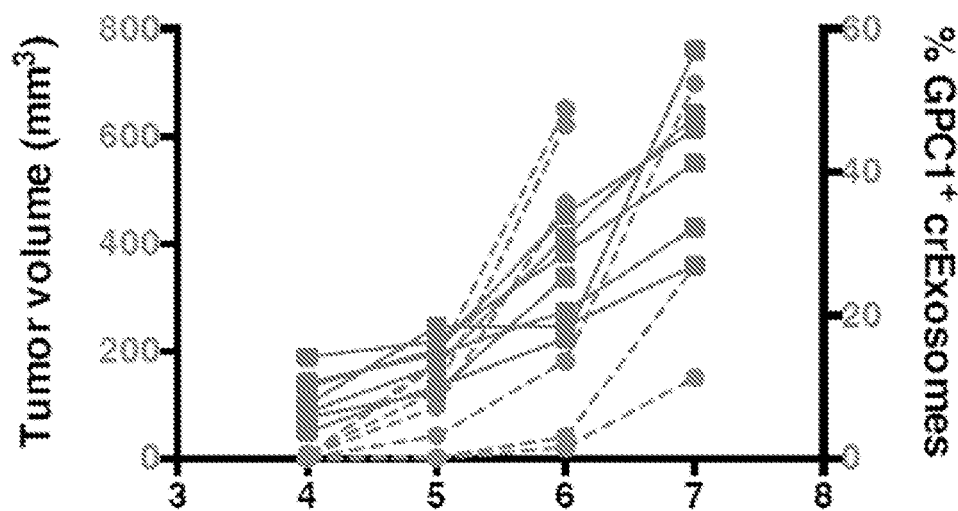
Figure 18D:
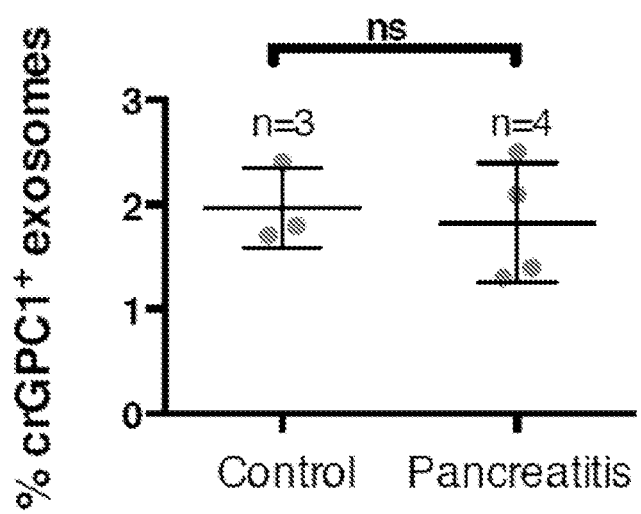

In light of the highly specific and sensitive detection of GPC1+ crExos in pancreatic cancer, the time course of GPC1+ crExos appearance was evaluated in the serum relative to pancreatic tumor burden. To this end, a genetically engineered mouse model (GEMM) for PDAC was used. Ptf1a$^{cre/+}$; LSL-Kras$^{G121/+}$; Tgfbr2$^{flox/flox}$ mice (PKT mice) (Ozdemir et al., 2014) develop PDAC with full penetrance that reliably recapitulates the clinical and histopathological features of the human disease (Odemir et al., 2014; Ijichi et al., 2006). The mice consistently progress from pancreatic intraepithelial neoplasia (PanIN) at 4.5 weeks of age and die at 8 weeks of age due to PDAC (Odemir et al., 2014; Ijichi et al., 2006). In a longitudinal study, PKT and littermate control mice were bled repeatedly at 4, 5, 6, 7, and 8 weeks of age (n=7 PKT mice and n=6 control mice; FIG. 13A). Three out of seven PKT mice were euthanized by week seven along with four out of six controls, while three PKT mice and two controls were euthanized at week eight. At 4 weeks of age PKT mice showed an average of 8.4% GPC1+ crExos, and this increased proportionally with time (and tumor burden), whereas control mice showed an average of 1.2% GPC1+ crExos and this level remained constant with time (FIGS. 13B and 18A-B). Magnetic resonance imaging (MRI), an established imaging modality used for the evaluation of PDAC (Lee and Lee, 2014), was performed at the same time points when mice were bled to measure GPC1+ crExos (e.g., at 4, 5, 6, and 7 weeks). When evaluated as a group, GPC1+ crExos levels appeared prior to MRI detectable pancreatic masses (FIGS. 13C and 18C). GPC1+ crExos size and concentration minimally correlated with pancreatic cancer (FIGS. 18A-B), whereas GPC1+ crExos levels correlated with tumor volume determined by MRI, and appeared to lead the growth of the tumor (Pearson correlation test, r=0.67, P=0.0005, 95% CI: 0.3504-0.8462; FIGS. 13C and 18C). Importantly, no elevation of GPC1+ crExos was noted in mice with Cerulein-induced acute pancreatitis, supporting GPC1+ crExos elevation as being pancreatic cancer-specific (FIG. 18D). ROC curve analysis for GPC1+ crExos showed an AUC of 1.0 (95% CI: 0.75-1.0) in PKT mice compared to healthy littermate control mice at all ages evaluated (FIG. 13D and Tables 11-12).

TABLE 11

Receiver operating characteristic (ROC) curve analysis for crGPC1+ exosomes, exosomes concentration, and exosomes size in PKT mice (n = 7) at 4 weeks of age vs. control (control littermate (n = 6) and mice with induced acute pancreatitis (n = 4), total n = 10)

| Parameter | AUC | CI | Cut-off value | Sensitivity | 95% CI | Specificity | 95% CI |
|---|---|---|---|---|---|---|---|
| GPC 1+ exosomes (%) | 1 | 0.805-1.00 | >2.5 | 100 | 59.0-100.0 | 100 | 69.2-100.0 |
| Exosomes Concentration (^10E08) | 0.814 | 0.555-0.958 | >5.76 | 100 | 59.0-100.0 | 70 | 34.8-93.3 |
| Exosomes Size (nm) | 0.657 | 0.393-0.865 | >104 | 57.14 | 18.4-90.1 | 80 | 44.4-97.5 |

TABLE 12

Receiver operating characteristic (ROC) curve analysis for GPC1-positive exosomes, exosomes concentration, and exosomes size in PKT mice (n = 7) at 5 (upper table), 6 (middle table) and 7 (lower table) weeks of age vs. control (control littermate n = 6 and mice with induced acute pancreatitis n = 4, total n = 10)

| Parameter | AUC | CI | Cut-off value | Sensitivity | 95% CI | Specificity | 95% CI |
|---|---|---|---|---|---|---|---|
| 5 weeks | | | | | | | |
| GPC 1+ exosomes (%) | 1 | 0.794-1.000 | >3.6 | 100 | 59.0-100.0 | 100 | 66.4-100.0 |
| Exosomes Concentration (^10E08) | 0.714 | 0.440-0.906 | >8.02 | 85.71 | 42.1-99.6 | 60 | 26.2-87.8 |
| Exosomes Size (nm) | 0.746 | 0.472-0.925 | >82 | 100 | 59.0-100.0 | 40 | 12.2-73.8 |
| 6 weeks | | | | | | | |
| GPC 1+ exosomes (%) | 1 | 0.794-1.000 | >2.6 | 100 | 54.1-100.0 | 100 | 69.2-100.0 |
| Exosomes Concentration (^10E08) | 0.783 | 0.512-0.945 | ≤743000000 | 83.33 | 35.9-99.6 | 80 | 44.4-97.5 |
| Exosomes Size (nm) | 0.592 | 0.324-0.824 | >104 | 50 | 11.8-88.2 | 80 | 44.4-97.5 |

TABLE 12-continued

Receiver operating characteristic (ROC) curve analysis for GPC1-positive exosomes, exosomes concentration, and exosomes size in PKT mice (n = 7) at 5 (upper table), 6 (middle table) and 7 (lower table) weeks of age vs. control (control littermate n = 6 and mice with induced acute pancreatitis n = 4, total n = 10)

| Parameter | AUC | CI | Cut-off value | Sensitivity | 95% CI | Specificity | 95% CI |
|---|---|---|---|---|---|---|---|
| 7 weeks | | | | | | | |
| GPC 1+ exosomes (%) | 1 | 0.794-1.000 | >2.5 | 100 | 54.1-100.0 | 100 | 69.2-100.0 |
| Exosomes Concentration (^10E08) | 0.725 | 0.451-0.913 | >11.64 | 50 | 11.8-88.2 | 100 | 69.2-100.0 |
| Exosomes Size (nm) | 0.933 | 0.692-0.998 | >104 | 100 | 54.1-100.0 | 80 | 44.4-97.5 |

Figure 13E:
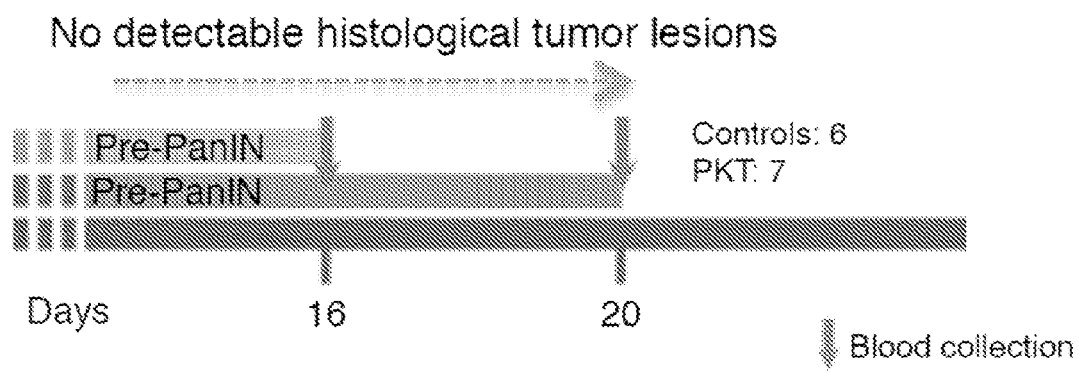
Figure 13F:
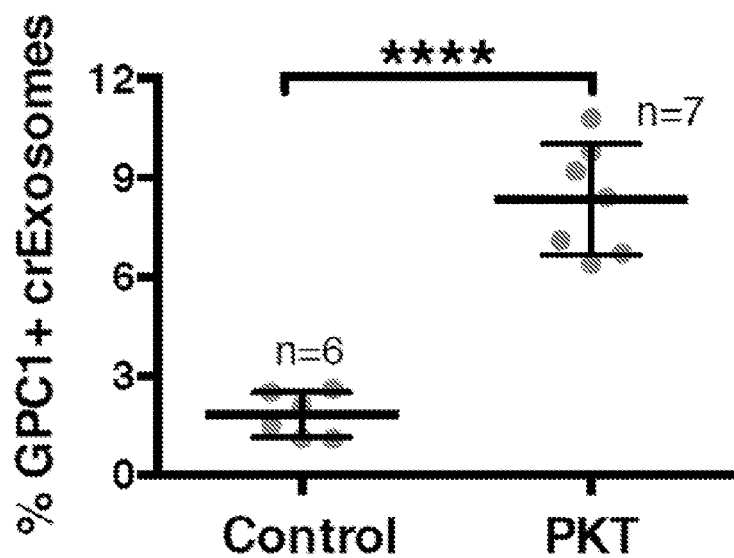
Figure 13G:
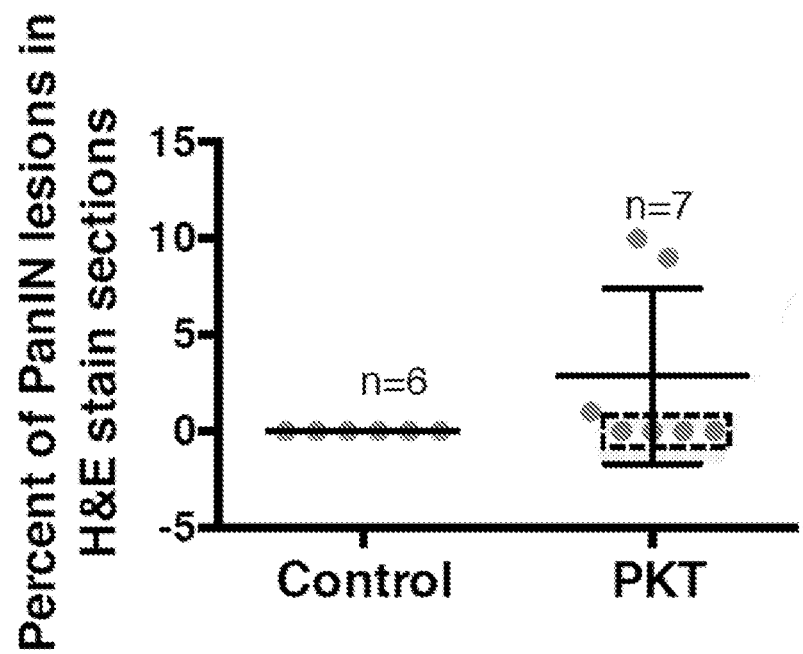
Figure 19:
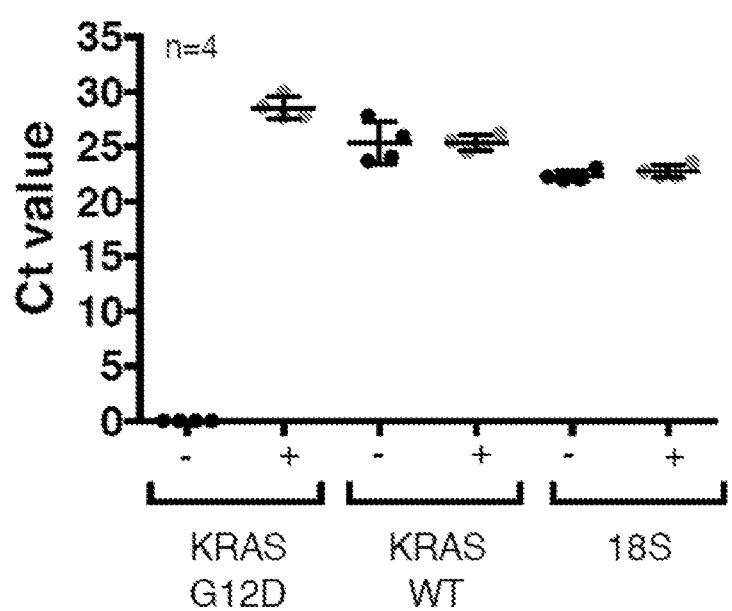
FIG. 19. PDAC GEMM cross-sectional study. Scatter plots representative for KRAS G12D, KRAS wild-type and 18s mRNA expression in exosomes that were separated by FACS sorting into GPC1$^+$ (+; gray) and GPC1$^-$ (−; black) populations.

A cross-sectional study was also initiated to assay tumor burden and GPC1+ crExos in PKT mice, as early as 16 and 20 days of age (FIG. 13E). Mice were imaged by MRI, bled, and euthanized at these early time points, when mice present with pre-PanINs to early PanIN lesions (FIG. 13E). GPC1+ crExos were detected in all PKT mice (PKT: 8.3% average, control: 1.8% average; FIG. 13F). Histological analysis of PKT mice confirmed pre-PanIN lesions in three out of seven PKT mice, and despite no observed histological lesions in four out of seven PKT mice, GPC1+ crExos predicted future pancreatic cancer emergence (FIG. 13G). Moreover, pancreas-associated masses were not observed by MRI in 16 and 20 days old PKT mice. Of note, in four out of seven PKT mice with no observed histological lesions, downstream signals for Kras activation, such as phosphorylated ERK (pERK), were detected in the pancreas tissue (FIG. 13G). Exclusive detection of mutant $KRAS^{G12D}$ mRNA in GPC1+ crExos compared to GPC1− crExos was also observed (FIG. 19).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945

Adamczyk et al., Characterization of soluble and exosomal forms of the EGFR released from pancreatic cancer cells. *Life Sciences*, 89:304-312, 2011.
Al-Nedawi et al., Intercellular transfer of the oncogenic receptor EGFRvIII by microvesicles derived from tumour cells. *Nature Cell Biology*, 10:619-624, 2008.
Andre et al., Malignant effusions and immunogenic tumour-derived exosomes. *Lancet*, 360:295-305, 2002.
Austin-Ward and Villaseca, Gene therapy and its applications. *Rev. Med. Chil.*, 126:838-845, 1998.
Balaj et al., Tumour microvesicles contain retrotransposon elements and amplified oncogene sequences. *Nature Communications*, 2:180, 2011.
Ballehaninna and Chamberlain, Biomarkers for pancreatic cancer: promising new markers and options beyond CA 19-9. *Tumour Biology: The Journal of the International Society for Oncodevelopmental Biology and Medicine*, 34:3279-3292, 2013.
Baran et al., Circulating tumour-derived microvesicles in plasma of gastric cancer patients. *Cancer Immunology, Immunotherapy: CII*, 59:841-850, 2010.
Bardeesy and DePinho, Pancreatic cancer biology and genetics. *Nature Reviews, Cancer*, 2:897-909, 2002.
Biankin et al., Pancreatic cancer genomes reveal aberrations in axon guidance pathway genes. *Nature*, 491:399-405, 2012.
Bilimoria et al., National failure to operate on early stage pancreatic cancer. *Annals of Surgery*, 246:173-180, 2007.
Borges et al., TGF-beta1-containing exosomes from injured epithelial cells activate fibroblasts to initiate tissue regenerative responses and fibrosis. *Journal of the American Society of Nephrology*, 24:385-392, 2013.
Bukowski et al., Signal transduction abnormalities in T lymphocytes from patients with advanced renal carcinoma: clinical relevance and effects of cytokine therapy. *Clin. Cancer Res.*, 4:2337-2347, 1998.
Chen et al., BEAMing and Droplet Digital PCR Analysis of Mutant IDH1 mRNA in Glioma Patient Serum and Cerebrospinal Fluid Extracellular Vesicles. *Molecular Therapy. Nucleic Acids*, 2:e109, 2013.
Choi et al., Proteomic analysis of microvesicles derived from human colorectal cancer ascites. *Proteomics*, 11:2745-2751, 2011.
Choi et al., The protein interaction network of extracellular vesicles derived from human colorectal cancer cells. *Journal of Proteome Research*, 11:1144-1151, 2012.
Christodoulides et al., Immunization with recombinant class 1 outer-membrane protein from *Neisseria meningitidis*: influence of liposomes and adjuvants on antibody avidity, recognition of native protein and the induction of a bactericidal immune response against meningococci. *Microbiology*, 144:3027-3037, 1998.

Ciravolo et al., Potential role of HER2-overexpressing exosomes in countering trastuzumab-based therapy. *Journal of Cellular Physiology*, 227:658-667, 2012.

Combes et al., A new flow cytometry method of platelet-derived microvesicle quantitation in plasma, *Thromb. Haemost.*, 77:220, 1997.

Conlon et al., Long-term survival after curative resection for pancreatic ductal adenocarcinoma. Clinicopathologic analysis of 5-year survivors. *Annals of Surgery*, 223:273-279, 1996.

Crowley et al., Liquid biopsy: monitoring cancer-genetics in the blood. *Nature Reviews, Clinical Oncology*, 10:472-484, 2013.

David et al., Molecular cloning of a phosphatidylinositol-anchored membrane heparan sulfate proteoglycan from human lung fibroblasts. *The Journal of Cell Biology*, 111:3165-3176, 1990.

Davidson et al., Intralesional cytokine therapy in cancer: a pilot study of GM-CSF infusion in mesothelioma. *J. Immunother.*, 21:389-398, 1998.

DeLong et al., Comparing the areas under two or more correlated receiver operating characteristic curves: a nonparametric approach. *Biometrics*, 44:837-845, 1988.

Del Villano et al., Radioimmunometric assay for a monoclonal antibody-defined tumor marker, CA 19-9. *Clinical Chemistry*, 29:549-552, 1983.

Demory Beckler et al., Proteomic analysis of exosomes from mutant KRAS colon cancer cells identifies intercellular transfer of mutant KRAS. *Molecular & Cellular Proteomics: MCP*, 12:343-355, 2013.

El-Andaloussi et al., Exosome-mediated delivery of siRNA in vitro and in vivo. *Nature Protocols*, 7:2112-2126, 2012.

El-Andaloussi et al., Extracellular vesicles: biology and emerging therapeutic opportunities. Nature reviews. *Drug Discovery*, 12:347-357, 2013.

Gartel, A new method for determining the status of p53 in tumor cell lines of different origin. *Oncology Research*, 13:405-408, 2003.

Grange et al., Microvesicles released from human renal cancer stem cells stimulate angiogenesis and formation of lung premetastatic niche. *Cancer Research*, 71:5346-5356, 2011.

Guescini et al., C2C12 myoblasts release micro-vesicles containing mtDNA and proteins involved in signal transduction. *Experimental Cell Research*, 316:1977-1984, 2010.

Hanibuchi et al., Therapeutic efficacy of mouse-human chimeric anti-ganglioside GM2 monoclonal antibody against multiple organ micrometastases of human lung cancer in NK cell-depleted SCID mice. *Int. J Cancer*, 78:480-485, 1998.

Harding et al., Endocytosis and intracellular processing of transferrin and colloidal gold-transferrin in rat reticulocytes: demonstration of a pathway for receptor shedding. *European Journal of Cell Biology*, 35:256-263, 1984.

Heijnen et al., Activated platelets release two types of membrane vesicles: microvesicles by surface shedding and exosomes derived from exocytosis of multivesicular bodies and alpha-granules. *Blood*, 94:3791-3799, 1999.

Hellstrand et al., Histamine and cytokine therapy. *Acta Oncol.*, 37:347-353, 1998.

Hergenreider et al., Atheroprotective communication between endothelial cells and smooth muscle cells through miRNAs. *Nature Cell Biology*, 14:249-256, 2012.

Hidalgo, Pancreatic cancer. *The New England Journal of Medicine*, 362:1605-1617, 2010.

Hollander, Immunotherapy for B-cell lymphoma: current status and prospective advances. *Front Immunol.*, 3:3, 2013.

Hui and Hashimoto, Pathways for Potentiation of Immunogenicity during Adjuvant-Assisted Immunizations with *Plasmodium falciparum* Major Merozoite Surface Protein 1. *Infec. Immun.*, 66:5329-5336, 1998.

Ijichi et al., Aggressive pancreatic ductal adenocarcinoma in mice caused by pancreas-specific blockade of transforming growth factor-beta signaling in cooperation with active Kras expression. *Genes & Development*, 20:3147-3160, 2006.

Janowska-Wieczorek et al., Microvesicles derived from activated platelets induce metastasis and angiogenesis in lung cancer. *International Journal of Cancer*, 113:752-760, 2005.

Jazieh et al., The clinical utility of biomarkers in the management of pancreatic adenocarcinoma. *Seminars in Radiation Oncology*, 24:67-76, 2014.

Ji et al., Proteome profiling of exosomes derived from human primary and metastatic colorectal cancer cells reveal differential expression of key metastatic factors and signal transduction components. *Proteomics*, 13:1672-1686, 2013.

Kahlert and Kalluri, Exosomes in tumor microenvironment influence cancer progression and metastasis. *J. Mol. Med. (Berl.)*, 91:431-437, 2013.

Kahlert et al., Identification of double-stranded genomic DNA spanning all chromosomes with mutated KRAS and p53 DNA in the serum exosomes of patients with pancreatic cancer. *The Journal of Biological Chemistry*, 289: 3869-3875, 2014.

Kirk, Breast cancer: Circulating tumour DNA the better of the blood biomarkers. *Nature Reviews, Clinical Oncology*, 10:247, 2013.

Kleeff et al., The cell-surface heparan sulfate proteoglycan glypican-1 regulates growth factor action in pancreatic carcinoma cells and is overexpressed in human pancreatic cancer. *The Journal of Clinical Investigation*, 102:1662-1673, 1998.

Kosaka et al., Trash or Treasure: extracellular microRNAs and cell-to-cell communication. *Frontiers in Genetics*, 4:173, 2013.

Kucharzewska et al., Exosomes reflect the hypoxic status of glioma cells and mediate hypoxia-dependent activation of vascular cells during tumor development. *Proceedings of the National Academy of Sciences USA*, 110:7312-7317, 2013.

Lau et al., Role of Pancreatic Cancer-derived Exosomes in Salivary Biomarker Development. *The Journal of Biological Chemistry*, 288:26888-26897, 2013.

Lee and Lee, Imaging diagnosis of pancreatic cancer: A state-of-the-art review. *World Journal of Gastroenterology: WJG*, 20:7864-7877, 2014.

Lievre et al., KRAS mutation status is predictive of response to cetuximab therapy in colorectal cancer. *Cancer Res.*, 66:3992-3995, 2006.

Livak and Schmittgen, Analysis of relative gene expression data using real-time quantitative PCR and the 2(-Delta Delta C(T)) method. *Methods*, 25:402-408, 2001.

Locker et al., ASCO 2006 update of recommendations for the use of tumor markers in gastrointestinal cancer. *Journal of Clinical Oncology: Official Journal of the American Society of Clinical Oncology*, 24:5313-5327, 2006.

Losche et al., Platelet-derived microvesicles transfer tissue factor to monocytes but not to neutrophils, *Platelets*, 15:109-115, 2004.

Luga et al., Exosomes mediate stromal mobilization of autocrine Wnt-PCP signaling in breast cancer cell migration. *Cell*, 151:1542-1556, 2012.

Matsuda et al., Glypican-1 is overexpressed in human breast cancer and modulates the mitogenic effects of multiple heparin-binding growth factors in breast cancer cells. *Cancer Research*, 61:5562-5569, 2001.

Mears et al., Proteomic analysis of melanoma-derived exosomes by two-dimensional polyacrylamide gel electrophoresis and mass spectrometry. *Proteomics*, 4:4019-4031, 2004.

Mesri and Altieri, Endothelial cell activation by leukocyte microparticles, *J. Immunol.*, 161:4382-4387, 1998.

Moore et al., Genetic profile of 22 pancreatic carcinoma cell lines. Analysis of K-ras, p53, p16 and DPC4/Smad4. *Virchows Arch.*, 439:798-802, 2001.

Morel et al., Cellular microparticles: a disseminated storage pool of bioactive vascular effectors, *Curr. Opin. Hematol.*, 11:156-164, 2004.

Morris et al., KRAS, Hedgehog, Wnt and the twisted developmental biology of pancreatic ductal adenocarcinoma. *Nature Reviews, Cancer*, 10:683-695, 2010.

Mouliere and Thierry, The importance of examining the proportion of circulating DNA originating from tumor, microenvironment and normal cells in colorectal cancer patients. *Expert Opinion on Biological Therapy*, 12(Suppl. 1):S209-215, 2012.

Murphy et al., Genetic alterations associated with progression from pancreatic intraepithelial neoplasia to invasive pancreatic tumor. *Gastroenterology*, 145:1098-1109 e1091, 2013.

Murtaza et al., Non-invasive analysis of acquired resistance to cancer therapy by sequencing of plasma DNA. *Nature*, 497; 108-112, 2013.

Nolte-'t Hoen et al., Deep sequencing of RNA from immune cell-derived vesicles uncovers the selective incorporation of small non-coding RNA biotypes with potential regulatory functions. *Nucleic Acids Research*, 40:9272-9285, 2012.

Ostrowski et al., Rab27a and Rab27b control different steps of the exosome secretion pathway. *Nature Cell Biology*, 12:19-30; S11-S13, 2010.

Ozdemir et al., Depletion of carcinoma-associated fibroblasts and fibrosis induces immunosuppression and accelerates pancreas cancer with reduced survival. *Cancer Cell*, 25:719-734, 2014.

Pan et al., Electron microscopic evidence for externalization of the transferrin receptor in vesicular form in sheep reticulocytes. *The Journal of Cell Biology*, 101:942-948, 1985.

Peinado et al., Melanoma exosomes educate bone marrow progenitor cells toward a pro-metastatic phenotype through MET. *Nature Medicine*, 18:883-891, 2012.

Pinzani et al., Circulating nucleic acids in cancer and pregnancy. *Methods*, 50:302-307, 2010.

Pisitkun et al., Identification and proteomic profiling of exosomes in human urine. *Proceedings of the National Academy of Sciences USA*, 101:13368-13373, 2004.

Qin et al., Interferon-beta gene therapy inhibits tumor formation and causes regression of established tumors in immune-deficient mice. *Proc. Natl. Acad. Sci. U.S.A.*, 95:14411-14416, 1998.

Rachagani et al., Activated KrasG(1)(2)D is associated with invasion and metastasis of pancreatic cancer cells through inhibition of E-cadherin. *British Journal of Cancer*, 104: 1038-1048, 2011.

Raposo et al., B lymphocytes secrete antigen-presenting vesicles. *The Journal of Experimental Medicine*, 183: 1161-1172, 1996.

Raposo and Stoorvogel, Extracellular vesicles: exosomes, microvesicles, and friends. *The Journal of Cell Biology*, 200:373-383, 2013.

Regev-Rudzki et al., Cell-cell communication between malaria-infected red blood cells via exosome-like vesicles. *Cell*, 153:1120-1133, 2013.

Remington's Pharmaceutical Sciences, 18th Ed., A. R. Gennaro et al. (eds.), Mack Publishing Co., Easton, Pa., 1990.

Rickes et al., Differentiation of pancreatic tumours by conventional ultrasound, unenhanced and echo-enhanced power Doppler sonography. *Scandinavian Journal of Gastroenterology*, 37:1313-1320, 2002.

Rothstein et al., Targeting signal 1 through CD45RB synergizes with CD40 ligand blockade and promotes long term engraftment and tolerance in stringent transplant models. *J. Immunol.*, 166:322-329, 2001.

Runz et al., Malignant ascites-derived exosomes of ovarian carcinoma patients contain CD24 and EpCAM. *Gynecologic Oncology*, 107:563-571, 2007.

Schellenberger et al., *Nature Biotech.*, 27:1186-1190, 2009.

Schmid et al., Non-invasive monitoring of pancreatic tumor progression in the RIP1-Tag2 mouse by magnetic resonance imaging. *Molecular Imaging and Biology: MIB: The Official Publication of the Academy of Molecular Imaging*, 15:186-193, 2013.

Silva et al., Analysis of exosome release and its prognostic value in human colorectal cancer. *Genes, Chromosomes & Cancer*, 51:409-418, 2012.

Skog et al., Glioblastoma microvesicles transport RNA and proteins that promote tumour growth and provide diagnostic biomarkers. *Nature Cell Biology*, 10:1470-1476, 2008.

Soo et al., Nanoparticle tracking analysis monitors microvesicle and exosome secretion from immune cells. *Immunology*, 136:192-197, 2012.

Steward and Levy, Preferential localization of polyribosomes under the base of dendritic spines in granule cells of the dentate gyrus. *The Journal of Neuroscience*, 2:284-291, 1982.

Su et al., Glypican-1 is frequently overexpressed in human gliomas and enhances FGF-2 signaling in glioma cells. *The American Journal of Pathology*, 168:2014-2026, 2006.

Taylor and Gercel-Taylor, MicroRNA signatures of tumor-derived exosomes as diagnostic biomarkers of ovarian cancer. *Gynecologic Oncology*, 110:13-21, 2008.

Taylor and Gercel-Taylor, Exosomes/microvesicles: mediators of cancer-associated immunosuppressive microenvironments. *Seminars in Immunopathology*, 33:441-454, 2011.

Thery et al., Exosomes: composition, biogenesis and function. *Nat. Rev. Immunol.*, 2:569-579, 2002.

Thery et al., Isolation and characterization of exosomes from cell culture supernatants and biological fluids. *Current Protocols in Cell Biology*, Ed., Juan S. Bonifacino et al., Chapter 3, Unit 3.22, 2006.

Thery et al., Membrane vesicles as conveyors of immune responses. *Nature Reviews, Immunology*, 9:581-593, 2009.

Trajkovic et al., Ceramide triggers budding of exosome vesicles into multivesicular endosomes. *Science*, 319:1244-1247, 2008.

Trams et al., Exfoliation of membrane ecto-enzymes in the form of micro-vesicles. *Biochimica et Biophysica Acta*, 645:63-70, 1981.

Valadi et al., Exosome-mediated transfer of mRNAs and microRNAs is a novel mechanism of genetic exchange between cells. *Nature Cell Biology*, 9:654-659, 2007.

Wells, RNA-binding proteins: a lesson in repression. *The Journal of Neuroscience*, 26:7135-7138, 2006.

Weyrich et al., Change in protein phenotype without a nucleus: translational control in platelets. *Seminars in Thrombosis and Hemostasis*, 30:491-498, 2004.

Whipple et al., Discovery of a novel molecule that regulates tumor growth and metastasis. *The Scientific World Journal*, 8:1250-1253, 2008.

Whipple et al., KrasG12D-driven genetic mouse model of pancreatic cancer requires glypican-1 for efficient proliferation and angiogenesis. *Oncogene*, 31:2535-2544, 2012.

Wiley and Gummuluru, Immature dendritic cell-derived exosomes can mediate HIV-1 trans infection. *Proceedings of the National Academy of Sciences USA*, 103:738-743, 2006.

Wilson et al., High resolution "ultra performance" liquid chromatography coupled to oa-TOF mass spectrometry as a tool for differential metabolic pathway profiling in functional genomic studies. *Journal of Proteome Research*, 4:591-598, 2005.

Xi et al., Copy number variation detection in whole-genome sequencing data using the Bayesian information criterion. *Proceedings of the National Academy of Sciences USA*, 108:E1128-1136, 2011.

Yachida et al., Distant metastasis occurs late during the genetic evolution of pancreatic cancer. *Nature*, 467:1114-1117, 2010.

Yamada et al., Cell Infectivity in Relation to Bovine Leukemia Virus gp51 and p24 in Bovine Milk Exosomes. *PLoS One*, 8:e77359, 2013.

Yong, Cancer biomarkers: Written in blood. *Nature*, 511:524-526, 2014.

Zeelenberg et al., Targeting tumor antigens to secreted membrane vesicles in vivo induces efficient antitumor immune responses. *Cancer Research*, 68:1228-1235, 2008.

Zilfou and Lowe, Tumor suppressive functions of p53. *Cold Spring Harbor Perspectives in Biology*, 1:a001883, 2009.

The invention claimed is:

1. A method of isolating cancer cell-derived exosomes comprising:
   (a) obtaining a body fluid sample from a cancer patient;
   (b) isolating an exosomes fraction of the body fluid sample; and
   (c) isolating exosomes from the exosomes fraction based on surface expression of glypican 1, thereby isolating cancer cell-derived exosomes.

2. The method of claim 1, further comprising isolating genomic double-stranded DNA, RNA, or proteins from the cancer cell-derived exosomes.

3. The method of claim 2, further comprising detecting a DNA, RNA, or protein isolated from the cancer cell-derived exosomes.

4. The method of claim 1, wherein the isolating of step (b) or (c) comprises immunomagnetic capture, adhesion-based sorting, magnetic-activated sorting, or fluorescence-activated sorting (FACS).

5. The method of claim 1, further comprising quantifying the number of cancer cell-derived exosomes in the patient.

6. The method of claim 1, further comprising genotyping the cancer cell-derived exosomes.

7. The method of claim 1, wherein the body fluid sample is lymph, saliva, urine, cerebrospinal fluid, bone marrow aspirates, eye exudate/tears, or serum.

8. The method of claim 1, wherein the cancer is a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer.

9. The method of claim 1, wherein isolating exosomes from the exosomes fraction based on surface expression of glypican 1, comprises isolating the exosomes using a glypican 1-binding antibody.

10. The method of claim 3, comprising isolating dsDNA from the cancer cell derived exosomes.

11. The method of claim 3, comprising sequencing DNA from the cancer cell derived exosomes.

12. The method of claim 10, comprising determining a mutation in at least one gene encoded by the dsDNA.

* * * * *